United States Patent
Bae et al.

(10) Patent No.: US 10,350,169 B2
(45) Date of Patent: Jul. 16, 2019

(54) COMPOSITIONS AND METHODS FOR BILE ACID PARTICLES

(71) Applicant: UNIVERSITY OF UTAH RESEARCH FOUNDATION, Salt Lake City, UT (US)

(72) Inventors: You Han Bae, Salt Lake City, UT (US); Yong-Kyu Lee, Chngbuk (KR); Md Nurunnabi, Chungbuk (KR); Hee Sook Hwang, Salt Lake City, UT (US); Dongsub Kwag, Seoul (KR)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/523,634

(22) PCT Filed: Oct. 30, 2015

(86) PCT No.: PCT/US2015/058375
§ 371 (c)(1),
(2) Date: May 1, 2017

(87) PCT Pub. No.: WO2016/070082
PCT Pub. Date: May 6, 2016

(65) Prior Publication Data
US 2017/0296481 A1    Oct. 19, 2017

Related U.S. Application Data

(60) Provisional application No. 62/073,588, filed on Oct. 31, 2014.

(51) Int. Cl.
*A61K 9/51* (2006.01)
*A61K 9/16* (2006.01)
(Continued)

(52) U.S. Cl.
CPC .......... *A61K 9/1652* (2013.01); *A61K 9/5036* (2013.01); *A61K 9/5123* (2013.01);
(Continued)

(58) Field of Classification Search
CPC .. A61K 9/1652; A61K 9/5036; A61K 9/5169; A61K 38/26; A61K 38/28;
(Continued)

(56) References Cited

U.S. PATENT DOCUMENTS 5,942,248 A    8/1999    Barnwell
6,245,753 B1   6/2001    Byun et al.
(Continued)

FOREIGN PATENT DOCUMENTS

CN    100594929    3/2010
EP    0127535      12/1984
(Continued)

OTHER PUBLICATIONS

Nan Zhang, et al, Polysaccharide-Based Micelles for Drug Delivery, 5 Pharmaceutics 329 (Year: 2013).*

(Continued)

*Primary Examiner* — Sean M Basquill
(74) *Attorney, Agent, or Firm* — Michael Best & Friedrich LLP

(57) ABSTRACT

Therapeutic compositions are disclosed which contain a therapeutic agent and a bile acid or bile acid conjugate. The compositions can be absorbed via enterohepatic circulation. The compositions include a cationic moiety and an anionic polymer, which are coupled through electrostatic interactions. The therapeutic compositions can be used for the treatment of diseases or disorders.

19 Claims, 59 Drawing Sheets

(51) Int. Cl.

| | | |
|---|---|---|
| A61K 9/50 | (2006.01) | |
| A61K 38/26 | (2006.01) | |
| A61K 38/28 | (2006.01) | |
| A61K 31/704 | (2006.01) | |
| A61K 47/54 | (2017.01) | |
| A61K 47/59 | (2017.01) | |
| A61K 47/61 | (2017.01) | |
| A61K 47/64 | (2017.01) | |
| A61K 47/18 | (2017.01) | |
| A61K 47/34 | (2017.01) | |
| A61K 47/46 | (2006.01) | |
| A61K 31/00 | (2006.01) | |
| A61K 9/127 | (2006.01) | |
| A61K 9/19 | (2006.01) | |

(52) U.S. Cl.
CPC .......... *A61K 9/5161* (2013.01); *A61K 9/5169* (2013.01); *A61K 31/00* (2013.01); *A61K 31/704* (2013.01); *A61K 38/26* (2013.01); *A61K 38/28* (2013.01); *A61K 47/18* (2013.01); *A61K 47/183* (2013.01); *A61K 47/34* (2013.01); *A61K 47/46* (2013.01); *A61K 47/554* (2017.08); *A61K 47/59* (2017.08); *A61K 47/61* (2017.08); *A61K 47/645* (2017.08); *A61K 47/6455* (2017.08); *A61K 9/1272* (2013.01); *A61K 9/1278* (2013.01); *A61K 9/19* (2013.01)

(58) Field of Classification Search
CPC .... A61K 31/704; A61K 47/554; A61K 47/59; A61K 47/61; A61K 47/645; A61K 47/6455; A61K 47/18; A61K 47/183; A61K 47/34; A61K 47/46; A61K 9/5123; A61K 9/5161; A61K 31/00; A61K 9/1272; A61K 9/1278; A61K 9/19
See application file for complete search history.

(56) References Cited

U.S. PATENT DOCUMENTS

| | | |
|---|---|---|
| 7,153,930 B1 | 12/2006 | Morrison et al. |
| 7,166,299 B2 | 1/2007 | Yoo |
| 7,303,768 B2 | 12/2007 | Yoo |
| 8,088,753 B2 | 1/2012 | Byun et al. |
| 2002/0098999 A1 | 7/2002 | Gallop et al. |
| 2002/0099041 A1 | 7/2002 | Gallop et al. |
| 2003/0012813 A1* | 1/2003 | Huang ............ A61K 9/1272 424/450 |
| 2005/0054559 A1 | 3/2005 | Gallop et al. |
| 2007/0087957 A1 | 4/2007 | Kidron |
| 2008/0026077 A1 | 1/2008 | Hilfinger et al. |
| 2009/0149424 A1 | 6/2009 | Byun et al. |
| 2010/0130426 A1* | 5/2010 | Young ............ A61K 9/0031 514/10.8 |
| 2013/0095187 A1 | 4/2013 | Hahn et al. |
| 2014/0120054 A1* | 5/2014 | Scheuing ............ A01N 25/02 424/78.27 |
| 2014/0249079 A1* | 9/2014 | Soula ............ A61K 47/34 514/5.9 |

FOREIGN PATENT DOCUMENTS

| | | |
|---|---|---|
| EP | 1720520 | 6/2010 |
| KR | 20110061881 | 6/2011 |
| WO | WO 2000/048636 | 8/2000 |
| WO | WO 2001/076531 | 10/2001 |
| WO | WO-02064115 A1 * 8/2002 ............ A61K 9/0095 |
| WO | WO 2011/097138 | 8/2011 |
| WO | 2014/084421 A1 | 6/2014 |

OTHER PUBLICATIONS

Khatun (Zehedina Khatun, et al, Oral Delivery of Taurocholic Acid Linked Heparin-Docetaxel Conjugates for Cancer Therapy, 170 J Control. Rel. 74, 75 (Sec. 2.2-2.3) (Year: 2013).*
European Patent Office Extended Search Report for Application No. 15854949.3 dated May 22, 2018 (7 pages).
Alam et al., "Oral delivery of a potent anti-angiogenic heparin conjugate by chemical conjugation and physical complexation using deoxycholic acid," Biomaterials, 2014, 35(24):6543-6552.
Al-Hilal et al., "Corrigendum: Functional transformations of bile acid transporters induced by high-affinity macromolecules," Scientific Reports, 2015, 5:09407.
Al-Hilal et al., "Oligomeric bile acid-mediated oral delivery of low molecular weight heparin," J Control Release, 2014, vol. 175, pp. 17-24.
Alrefai et al., "Bile acid transporters: structure, function, regulation and pathophysiological implications," Pharm. Res., 2007, 24(10):1803-1823.
Bowman et al., "Gene transfer to hemophilia A mice via oral delivery of FVIII-chitosan nanoparticles," J Control Release. 2008;132(3):252-259.
Chuang et al., "Combination therapy via oral co-administration of insulin- and exendin-4-loaded nanoparticles to treat type 2 diabetic rats undergoing OGTT," Biomaterials. 2013;34(32):7994-8001.
Da Rocha et al., "Natural products in anticancer therapy," Curr. Opin. Pharmacol., 2001, 1(4):364-369.
Dawson et al., "Bile acid transporters," J. Lipid Res., 2009, 50(12):2340-2357.
Dayton et al., "Amelioration of doxorubicin-induced cardiotoxicity by an anticancer-antioxidant dual-function compound, HO-3867," J. Pharm. Exp. Ther., 2011, 339(2):350-357.
Haisler et al., "Three-dimensional cell culturing by magnetic levitation," Nat. Protoc., 2013, 8(10):1940-1949.
He et al., "Size-dependent absorption mechanism of polymeric nanoparticles for oral delivery of protein drugs," Biomaterials, 2012, 33(33): 8569-8578.
Holm et al., "Bile salts and their importance for drug absorption," Int. J. Pharm., 2013, 453(1):44-55.
Hu et al., "pH-responsive and charge shielded cationic micelle of poly (l-histidine)-block-short branched PEI for acidic cancer treatment," J. Control. Release, 2013, 172(1):69-76.
Hwang et al., "Orally active desulfated low molecular weight heparin and deoxycholic acid conjugate, 6ODS-LHbD, suppresses neovascularization and bone destruction in arthritis," J Control Release. Nov. 10, 2012;163(3):374-84.
International Search Report and Written Opinion for Application No. PCT/US2015/058375 dated Jan. 21, 2016 (10 pages).
Iusuf et al., "Functions of OATP1A and 1B transporters in vivo: insights from mouse models," Trends in Pharmacological Science 2012, 33(2):100-108.
Jafari et al., "Ultrasound-assisted synthesis of colloidal nanosilica from silica fume: Effect of sonication time on the properties of product," Adv Power Technol., 2014, 25(5):1571-1577.
Kang et al., "A reducible polycationic gene vector derived from thiolated low molecular weight branched polyethyleneimine linked by 2-iminothiolane," Biomaterials, 2011, 32(4):1193-1203.
Kang et al., "Co-delivery of small interfering RNA and plasmid DNA using a polymeric vector incorporating endosomolytic oligomeric sulfonamide," Biomaterials, 2011, 32(21):4914-24.
Kang et al., "DNA Polyplexes as Combinatory Drug Carriers of Doxorubicin and Cisplatin: An in Vitro Study," Mol. Pharmaceutics, 2015, 12(8):2845-2857.
Kang et al., "The effect of environmental pH on polymeric transfection efficiency," Biomaterials, 2012, 33(5):1651-62.
Khatun et al., "Oral absorption mechanism and anti-angiogenesis effect of taurocholic acid-linked heparin-docetaxel conjugates," J. Control. Release, 2014, vol. 177, pp. 64-73.
Khatun et al., "Oral delivery of taurocholic acid linked heparin-docetaxel conjugates for cancer therapy," J. Control. Release, 2013, 170(1):74-82.

(56) References Cited

OTHER PUBLICATIONS

Kim et al., "In vivo evaluation of doxorubicin-loaded polymeric micelles targeting folate receptors and early endosomal pH in drug-resistant ovarian cancer," Mol. Pharm., 2009, 6(5):1353-1362.
Kim et al., "Oral delivery of chemical conjugates of heparin and deoxycholic acid in aqueous formulation," Thromb Res. 2006;117(4):419-27.
Kim et al., "The limited intestinal absorption via paracellular pathway is responsible for the low oral bioavailability of doxorubicin," Xenobiotica, 2012, 43(7):579-591.
Krylova et al., "Ionophoric activity of pluronic block copolymers," Biochemistry, 2004, 43:3696-3703.
Kwag et al., "Facile synthesis of multilayered polysaccharidic vesicles," J. Control. Release, 2014, vol. 187, pp. 83-90.
Kwag et al., "Facile synthesis of partially incapped liposomes," Colloids Suf B Biointerfaces, 2015, 135:143-149.
Lee et al., "A Virus-Mimetic Nanogel Vehicle," Angew. Chem. Int. Ed. Engl., 2008, 47(13):2418-2421.
Lee et al., "Conjugation of low-molecular-weight heparin and deoxycholic acid for the development of a new oral anticoagulant agent," Circulation. Dec. 18, 2001;104(25):3116-20.
Lee et al., "Facile Synthesis of Multimeric Micelles," Angew. Chem. Int. Ed., 2012, 51(29):7287-7291.
Lee et al., "Multimeric grain-marked micelles for highly efficient photodynamic therapy and magnetic resonance imaging of tumors," Int. J. Pharm., 2014, 471:166-172.
Lee et al., "Oral delivery of new heparin derivatives in rats," Pharm Res. Oct. 2000; 17(10):1259-64.
Li et al., "A co-delivery system based on paclitaxel grafted mpeg-b-plg loaded with doxorubicin: preparation, in vitro and in vivo evaluation," International Journal of Pharmaceutics, 2014, 471(1-2):412-420.
Lin et al., "Preparation and characterization of nanoparticles shelled with chitosan for oral insulin delivery," Biomacromolecules. 2007;8(1):146-52.
Mei et al., "Pharmaceutical nanotechnology for oral delivery of anticancer drugs," Adv. Drug Deliv. Rev., 2013, 65(6):880-890.
Mi et al., "Oral delivery of peptide drugs using nanoparticles self-assembled by poly(gamma-glutamic acid) and a chitosan derivative functionalized by trimethylation," Bioconjug Chem. 2008;19(6):1248-55.
Mohan et al., "Doxorubicin as a molecular nanotheranostic agent: effect of doxorubicin encapsulation in micelles or nanoemulsions on the ultrasound-mediated intracellular delivery and nuclear trafficking," Mol. Pharm., 2010, 7(6):1959-1973.
Motion et al., "Phosphatase-Triggered Fusogenic Liposomes for Cytoplasmic Delivery of Cell-Impermeable Compounds," Angew. Chem. Int. Ed., 2012, 51(36):9047-9051.
Napoli et al., "Oxidation-responsive polymeric vesicles," Nat. Mater., 2004, vol. 3, 183-189.
Oerlemans et al., "Evidence for a New Mechanism Behind HIFU-triggered Release From Liposomes," J. Control. Release, 2013, 168(3):327-333.
Oprea et al., "Synthesis and characterization of some cellulose/chondroitin sulphate hydrogels and their evaluation as carriers for drug delivery," Carbohydr Polym., 2012, 87(1):721-729.
Pridgen et al., "Transepithelial transport of Fc-targeted nanoparticles by the neonatal fc receptor for oral delivery," Sci Transl Med, 2013, 5(213):213ra167.
Przybylo et al., "The alteration of lipid bilayer dynamics by phloretin and 6-ketocholestanol," Chemistry and Physics of Lipids, 2014, 178:38-44.
Regulation of Bile Release, <http://courses.washington.edu/conj/bess/bile/bile.html> webpage available as early as May 23, 2009.
Roopenian et al., "FcRn: the neonatal Fc receptor comes of age," Nat Rev Immunol., 2007, 7(9):715-725.
Roy et al., "Oral gene delivery with chitosan—DNA nanoparticles generates immunologic protection in a murine model of peanut allergy," Nat Med., 1999, 5(4):387-391.
Safinya et al., "Materials chemistry: Liposomes derived from molecular vases," Nature, 2012, 489:372-374.
Saitoh et al., "Opening-up of liposomal membranes by talin," PNAS, 1998, 95:1026-1031.
Sonaje et al., "Biodistribution, pharmacodynamics and pharmacokinetics of insulin analogues in a rat model: Oral delivery using pH-Responsive nanoparticles vs. subcutaneous injection," Biomaterials, 2010, 31(26):6849-6858.
Sonaje et al., "Effects of chitosan-nanoparticle-mediated tight junction opening on the oral absorption of endotoxins," Biomaterials, 2011, 32(33):8712-21.
Sonaje et al., "In vivo evaluation of safety and efficacy of self-assembled nanoparticles for oral insulin delivery," Biomaterials, 2009, 30(12):2329-2339.
Sung et al., "pH-Responsive Nanoparticles Shelled with Chitosan for Oral Delivery of Insulin: From Mechanism to Therapeutic Applications," Accounts of Chemical Research, 2012, 45(4):619-629.
Swarnakar et al., "Bicontinuous cubic liquid crystalline nanoparticles for oral delivery of doxorubicin: implications on bioavailability, therapeutic efficacy, and cardiotoxicity," Pharm. Res., 2014, 31(5):1219-1238.
Talelli et al., "Core-crosslinked polymeric micelles with controlled release of covalently entrapped doxorubicin," Biomaterials, 2010, 31(30):7797-7804.
Taluja et al., "Role of a novel excipient poly(ethylene glycol)-b-poly(L-histidine) in retention of physical stability of insulin in aqueous solutions," Pharm. Res., 2007, 24(8):1517-1526.
Thanki et al., "Oral delivery of anticancer drugs: challenges and opportunities," J. Control. Release, 2013, 170(1):15-40.
Thomas et al., "Targeting bile-acid signalling for metabolic diseases," Nat. Rev. Drug Discov., 2008, 7(8):678-693.
Tran et al., "Microfluidic approach for highly efficient synthesis of heparin-based bioconjugates for drug delivery," Lab Chip, 2012, 12(3):589-594.
Wang et al., "Improved oral absorption of doxorubicin by amphiphilic copolymer of lysine-linked di-tocopherol polyethylene glycol 2000 succinate," Mol. Pharm., 2015, 12(2):463-473.
Yin Wim et al., "Effects of particle size and surface coating on cellular uptake of polymeric nanoparticles for oral delivery of anticancer drugs," Biomaterials, 2005, 26(15):2713-2722.
Yoshizaki et al., "Potentiation of pH-sensitive polymer-modified liposomes with cationic lipid inclusion as antigen delivery carriers for cancer immunotherapy," Biomaterials, 2014, 35(28):8186-8196.
Zhang et al., "Advanced materials and processing for drug delivery: the past and the future," Adv. Drug Deliv. Rev., 2013, 65(1):104-120.
Zhou et al., "Structural basis of the alternating-access mechanism in a bile acid transporter," Nature, 2014, 505(7484):569-73.
Kim et al., "Combinational chemoprevention effect of celecoxib and an oral antiangiogenic LHD4 on colorectal carcinogenesis in mice," Anticancer Drugs. Oct. 2014;25(9):1061-71.

* cited by examiner

COMPOSITIONS AND METHODS FOR BILE ACID PARTICLES

CROSS REFERENCE TO RELATED APPLICATIONS

This application is a U.S. national stage entry of International Patent Application No. PCT/US2015/058375, filed on Oct. 30, 2015, which claims priority to U.S. Provisional Patent Application No. 62/073,588, filed on Oct. 31, 2014, the entire contents of all of which are fully incorporated herein by reference.

FIELD OF INVENTION

The disclosure provided herein relates to therapeutic compositions which contain a bile acid, and which can be orally administered to a patient and absorbed via enterohepatic circulation. The compositions include a cationic moiety and an anionic moiety, which are coupled by electrostatic interactions. The compositions contain a therapeutic agent, such as a gene, a protein, or a small molecule.

BACKGROUND

The oral delivery of certain therapeutic agents is limited by many factors, including low bioavailability resulting from poor intestinal permeability, decomposition of the therapeutic agent due to pH or temperature instability, and proteolytic enzyme degradation. There is a need for compositions and delivery methods which can improve the bioavailability of therapeutic agents, which can result in higher patient compliance, more reproducibility between patient populations, lower doses, a wider therapeutic window, and a lower overall cost of treating a variety of diseases or disorders.

SUMMARY

The present disclosure provides a therapeutic composition which contains a core complex made with a therapeutic agent and which has an exterior surface with a net positive charge at a pH of 5, and which also contains a bile acid or a bile acid conjugate which is covalently bound to an anionic polymer. The anionic polymer has a net negative charge at neutral pH, and the anionic polymer is also electrostatically coupled to the exterior surface of the core complex.

The present disclosure also provides methods of delivering a therapeutic agent to a cell, through oral administration of a therapeutic composition which contains a core complex made with a therapeutic agent and which has an exterior surface with a net positive charge at a pH of 5, and which also contains a bile acid or a bile acid conjugate which is covalently bound to an anionic polymer. The anionic polymer has a net negative charge at neutral pH, and the anionic polymer is also electrostatically coupled to the exterior surface of the core complex.

The therapeutic agent may be absorbed by the subject or a patient through a bile acid transporter in the gastrointestinal tract, whereby it enters the enterohepatic circulatory system. The therapeutic compositions may include an anticancer agent, and may be used to treat cancer. The therapeutic compositions may also be used to treat a metabolic disease or disorder.

Other aspects of the disclosure will become apparent by consideration of the detailed description and accompanying drawings.

BRIEF DESCRIPTION OF THE DRAWINGS

This patent or patent application file contains at least one drawing executed in color. Copies of this patent or patent application publication with color drawings will be provided by the Office upon request with payment of the necessary fee.

The drawings below are supplied in order to facilitate understanding of the Description and Examples provided herein.

DETAILED DESCRIPTION

Figure 1A:
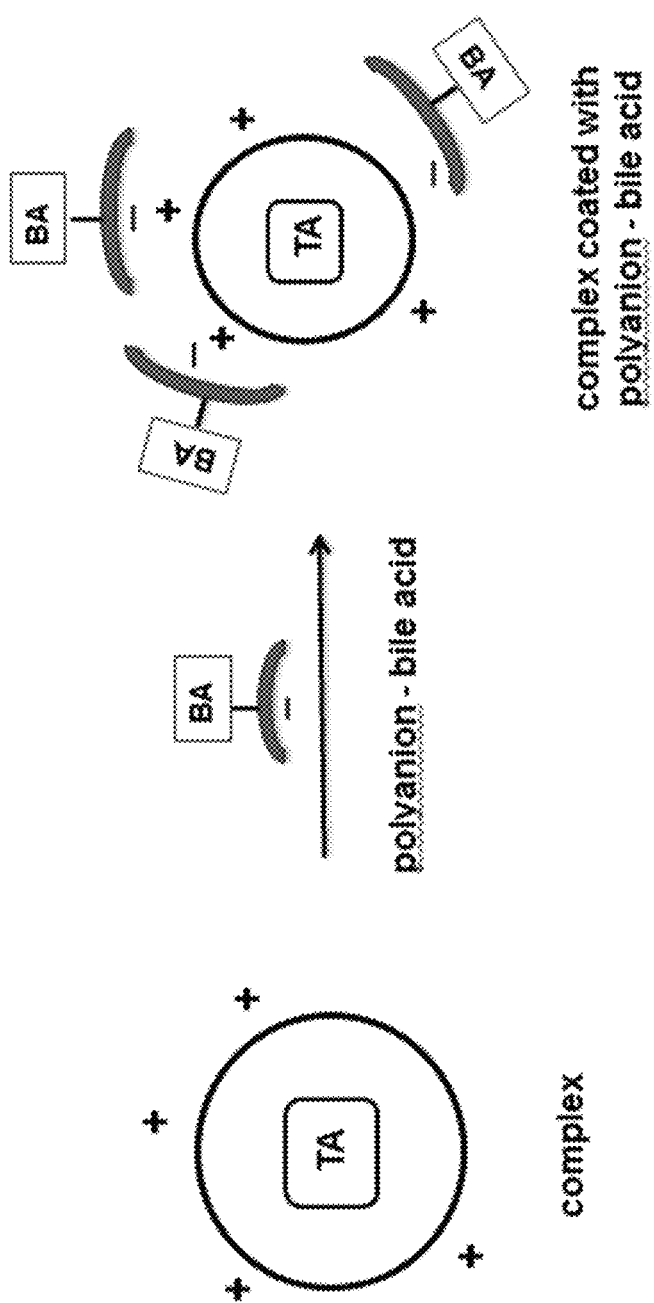
FIGS. 1A-1C are schematic illustrations of exemplary therapeutic compositions.

The oral delivery of therapeutic compositions must address numerous challenges that can limit their use, including poor intestinal permeability, decomposition of the therapeutic agent due to pH or temperature instability, and proteolytic enzyme degradation. The development of oral formulations takes into account multiple factors which affect the bioavailability of a therapeutic agent, including its solubility, stability, dissolution rate, and permeability of the in the gastrointestinal (GI) tract. Generally, oral dosage forms of therapeutic agents should have a rapid dissolution rate and a high absorption rate, to lower the half-life and metabolism of the therapeutic agent in the GI tract and thus maximize its bioavailability. A therapeutic agent with a high oral bioavailability can provide higher patient compliance, more reproducibility between patient populations, lower doses, and a wider therapeutic window than a therapeutic agent with a lower bioavailability, leading to a lower overall cost of treating a disease or disorder.

One aspect that hampers the efficacy of a therapeutic agent results from barriers that limit intestinal absorption from the epithelial lining of the walls of the gastrointestinal tract. Bile acid transporters are an attractive target for the delivery of therapeutic agents, because bile acids secreted from the liver are reabsorbed from the terminal ileum through intestinal epithelial cells and transported back to the liver via the portal vein. Thus, high bile acid recycling ratios make the enterohepatic circulation of bile acids a highly efficient process and benefit the bile acid transporters that are mainly expressed in the liver and the terminal ileum.

Taurocholic acid (TCA) is an abundant bile acid, estimated to account for approximately 45% of human intestinal fluid. TCA can be used as a carrier of therapeutic agents by maximizing the intestinal transcellular absorption via apical sodium bile acid transporters (ASBTs), which are present mainly in the terminal ileum. Thus, transport of the therapeutic agent from the terminal ileum to the portal vein and into the systemic circulation can be facilitated by a bile acid carrier such as TCA.

Disclosed herein are therapeutic compositions which contain a complex of a therapeutic agent and a cationic moiety, which are electrostatically connected to a bile acid which is covalently bound to an anionic moiety. The compositions form particles with diameters ranging from about 20 nm to about 5000 nm in size, and which are absorbed into the blood from the gastrointestinal tract (GIT), primarily from the ileum. In some embodiments, the diameters of the particles are between about 20 nm-5000 nm, between about 50 nm-1000 nm, are at least about 20 nm in size, at least about 50 nm, at least about 100 nm, nor more than about 5000 nm, or no more than about 1000 nm. The therapeutic compositions contain an anionic moiety that is covalently bonded to at least one bile acid, a cationic moiety which interacts electrostatically with the anionic moiety, and include at least one therapeutic agent. In certain embodiments, the compositions may include more than one therapeutic agent, or at least two therapeutic agents.

Without being bound by theory, it is believed that the primary mechanism of the absorption of the compositions by the GIT after oral administration is via the enterohepatic circulation system of bile acids, which recycles digestive bile acids from the GIT to the liver. The bile acid-decorated composition takes advantage of the bile acid recycling pathway and allows the therapeutic agent to be carried into the bloodstream. The anionic moiety provides biocompatibility and prevents the particles from both aggregation and nonspecific absorption from the GIT.

The therapeutic compositions described herein can provide a therapeutic agent to a subject with a higher oral bioavailability than if the agent was provided without a bile acid. Incorporation of the bile acid allows for the therapeutic agent to be orally administered to the patient. The compositions not only provide an improved bioavailability for therapeutic agents which are currently administered orally, such as anticancer agents including doxorubicin, but also allow for the administration of therapeutic agents which are not typically thought to be orally administered. Such agents include DNA, RNA, gene or oligonucleotide therapeutics, as well as proteins, antibodies, and polypeptides, vaccines, vectors or viruses. The inventive compositions provide a platform technology which can overcome the challenges of oral delivery due to poor intestinal permeability, decomposition of the therapeutic agent due to pH or temperature instability, and enzymatic degradation.

Specifically, therapeutic compositions are described which contain a core complex made with a therapeutic agent and which has an exterior surface with a net positive charge at a pH of 5. The composition also contains a bile acid or a bile acid conjugate which is covalently bound to an anionic polymer. The anionic polymer has a net negative charge at neutral pH, and the anionic polymer is also electrostatically coupled to the exterior surface of the core complex. An illustration of the design of these therapeutic compositions is shown in FIG. 1, where a complex which contains a therapeutic agent (TA) and which has a cationic surface is coupled with a moiety formed with a bile acid or bile acid conjugate (BA) which is covalently bound to an anionic polymer. The resultant composition has a core complex which is coated with the BA-polyanion moiety, in which the cationic surface of the core complex is electrostatically coupled with the anionic polymer to form a stable and discrete particulate composition.

The therapeutic agent can be of generally any type, including a nucleic acid, gene, protein, peptide, virus, vaccine or small molecule drug. In certain embodiments, the therapeutic agent is a gene, linear DNA, plasmid DNA, RNA, RNAi, or mRNA, such as a gene which encodes GLP-1 or Exendin-4. The therapeutic agent may be a protein, antibody or peptide such as insulin, growth hormone, or erythropoietin, or it may be a peptide such as calcitonin or LHRH. It may be a small molecule drug such as an anticancer drug, including doxorubicin, cisplatin or paclitaxel. It may also be a virus such as an influenza virus or an oncolytic adenovirus.

The core complex may comprise a single cationic therapeutic agent, or multiple cationic agents, or it may comprise two or more moieties which are associated such that the exterior surface has a net positive charge at a pH of 5. In certain embodiments, the exterior surface has a net positive charge at any pH between about 1 and about 8, or a net positive charge at neutral pH. The core complex may comprise a cationic polymer such as polyethylenimine, protamine or poly(lysine). The cationic polymer may be a nucleic acid or portion of DNA with a net positive charge at a pH of 5. In some embodiments, the core complex comprises a cationic liposome, or a cationic lipid or mixture of lipids.

The polyanion or anionic polymer is a polymer which has a net negative charge at neutral pH, such as polymers comprising at least one sulfonate, carboxylate, phosphate or sulfonamide group. The pKa of the polyanion may have a value below 10, or it may be below 8. The polyanion may be a natural polymer such as a polysaccharide including dextran sulfate, heparin, heparin sulfate, chondroitin sulfate, hyaluronic acid, or alginic acid; a nucleic acid or portion of DNA including RNA, siRNA, mRNA and ODN; or a protein such as albumin. It may be a synthetic polymer such as polyvinyl sulfone, poly(2-acylamido-2-methyl-1-propane sulfonic acid (polyAMPS), a poly(acrylic acid), a poly(methacrylic acid), a poly(ethylacrylic acid), a poly(propylacrylic acid), a poly(styrene sulfonate), a poly(sulfonamide), a poly(phosphate), poly(2-methacryloyloxyethyl phosphorylcholine), or any mixture or copolymers of any of the aforementioned polymers. The polymer may be a random, block, graft or alternating polymer. The polyanion may be a mixture of a natural or a synthetic polymer, or a mixture of two or more polymers of any type.

The BA moiety can be a bile acid or a bile acid conjugate, a primary bile acid such as cholic acid or chenocholic acid, a secondary bile acid such as deoxycholic acid, lithocholic acid, ursodeoxycholic acid, or chenodeoxycholic acid, or any type of bile acid salt. In certain embodiments, the bile acid or bile acid conjugate is taurocholic acid, glycocholic acid, taurodeoxycholic acid, glycodeoxycholic acid, taurochenodeoxycholic acid, glycochenodeoxycholic acid, or any modified bile acid which binds to a protein involved with bile acid transport, such as ASBT. The BA moiety may be a mixture of any of the exemplary components listed above, or it may be a single entity.

Figure 1B:
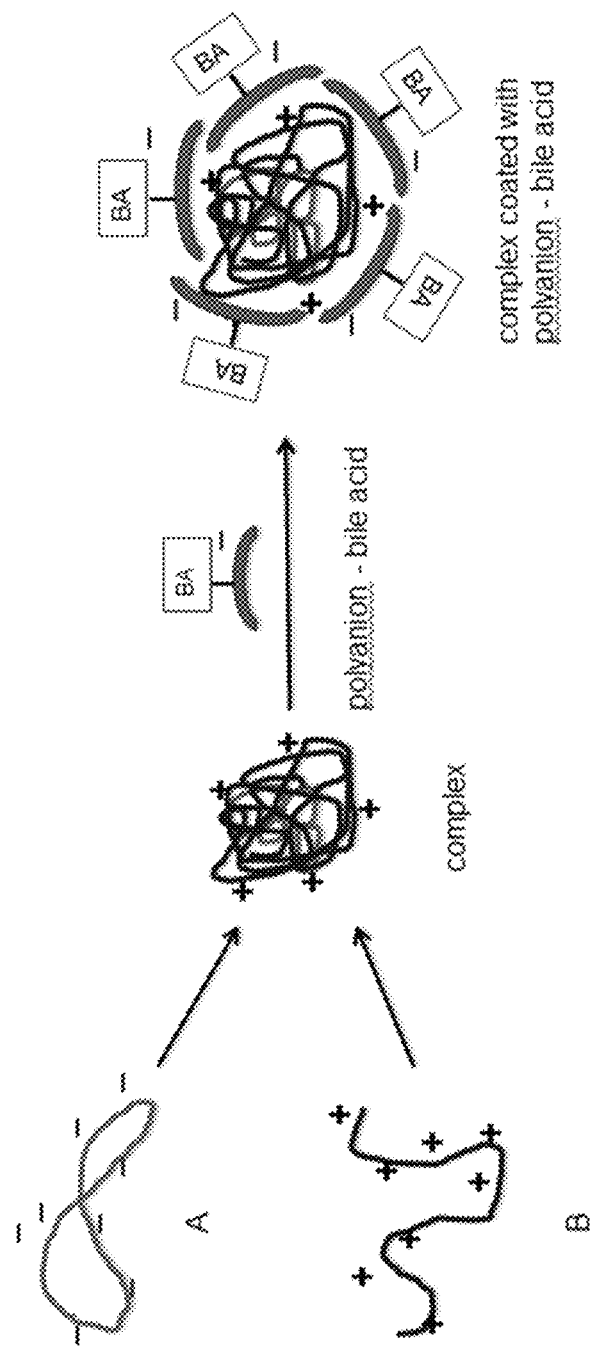
Figure 1C:
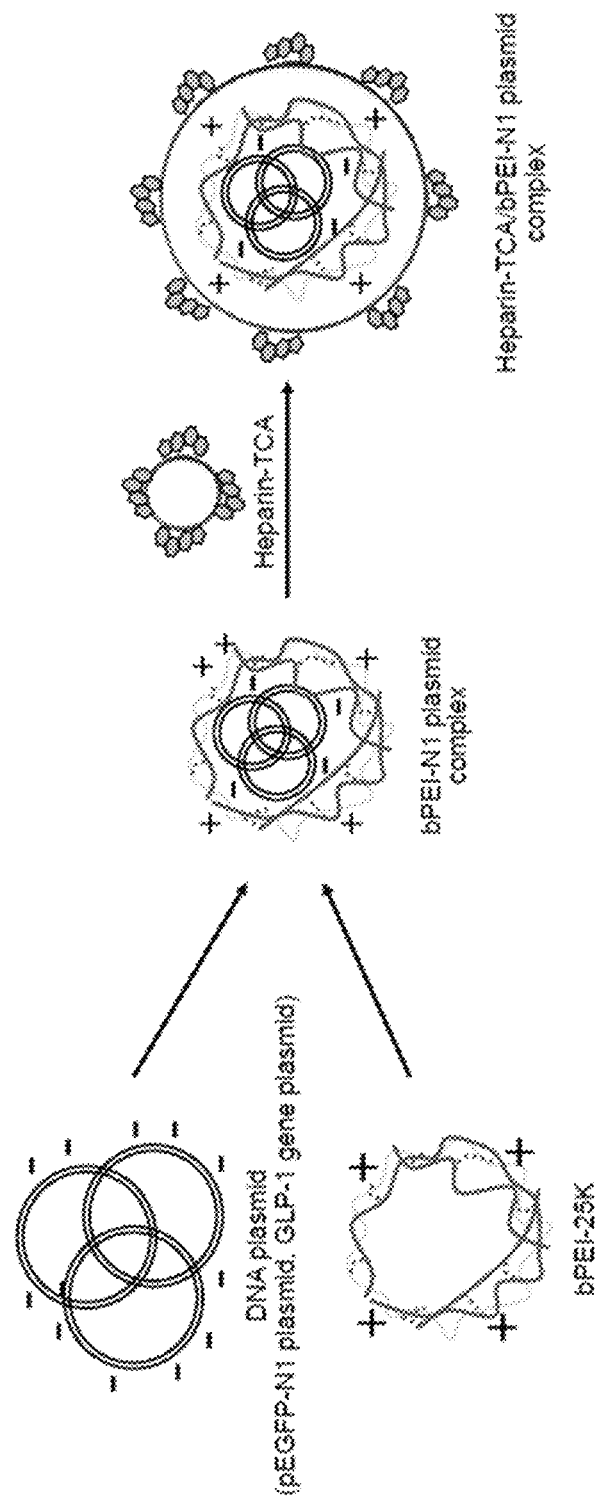

Other embodiments of the general scheme of FIG. 1A are shown in FIGS. 1B and 1C. FIG. 1B is a schematic representation of a moiety A, which can be a plasmid DNA, which associates with a moiety B, such as a cationic polymer, to form a core complex which has an exterior cationic surface. The core complex electrostatically binds with the anionic polymer which is covalently bound to the BA moiety, to form the therapeutic composition with the BA on the outer surface. In an embodiment, the B moiety is bPEI, the A moiety is a plasmid DNA such as pEeGFP-N1, pGLP-1, or pExendin-4, and the polyanion-bile acid conjugate moiety is heparin-TCA. In FIG. 1C, the various components of the formulation are described in detail, including the core complex which is wrapped with the bile acid or bile acid conjugate covalently bound to an anionic polymer.

The linkage between the bile acid or bile acid conjugate and the anionic polymer is via a covalent bond. An example of a bile acid and an anionic polymer used to form this linked product is chondroitin sulfate as the anionic polymer, and taurocholic acid as the bile acid. A general synthetic route which can be used to covalently link these compounds to form the anionic polymer-bile acid moiety used in the compositions disclosed herein, is shown below in Scheme 1 for the synthesis of CS-TCA:

Scheme 1

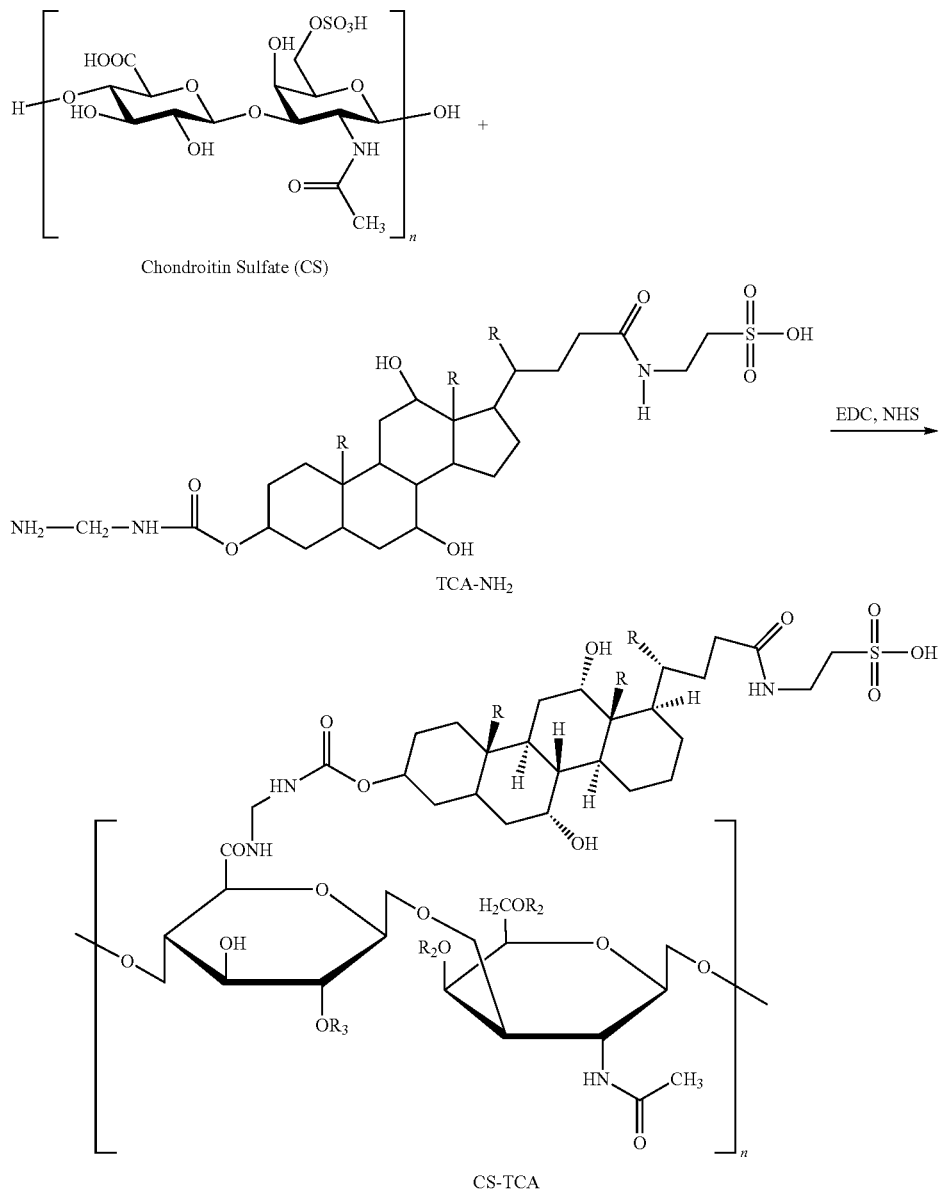

As used herein, the term "bile acid conjugate" refers to a bile acid salt, including bile acid salts comprising taurine or glycine. The term "bile acid" includes a bile acid conjugate, unless otherwise noted.

As used herein, the term "complex" refers to at least one moiety, and can include two or more moieties which are associated with each other. In embodiments in which the complex is made of two or more moieties, the moieties may be associated with each other through a covalent or a non-covalent bond, including an electrostatic interaction, ionic interaction, hydrogen-bonding, a pi bond, or any combination thereof.

As used herein, the terms "small molecule" or "small-molecule" mean a chemical compound that is not considered to be a biologic, which has a molecular weight of no more than about 1000 daltons. The terms are used generally to differentiate this type of therapeutic agent from protein or nucleic acid-containing agents.

The use of the disclosed compositions allows for the oral delivery of a wide range of therapeutic agents by improving their bioavailability, to treat multiple diseases and to potentially improve the safety of drug treatments through lower doses and a wider therapeutic window. These improvements can be beneficial to patients by improving treatment regimens and efficacy, and open up new avenues for delivering therapeutic agents traditionally thought not to be able to be administered orally.

Before any embodiments of the invention are explained in detail, it is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items.

It also should be understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

It should be understood that, as used herein, the term "about" is synonymous with the term "approximately." Illustratively, the use of the term "about" indicates that a value includes values slightly outside the cited values. Variation may be due to conditions such as experimental error, manufacturing tolerances, and variations in equilibrium conditions. In some embodiments, the term "about" includes the cited value plus or minus 10%. In all cases, where the term "about" has been used to describe a value, it should be appreciated that this disclosure also supports the exact value.

Reference throughout this specification to "one embodiment," "an embodiment," "an aspect," or similar language means that a particular feature, structure, or characteristic described in connection with the embodiment is included in at least one embodiment of the invention provided herein. Thus, appearances of the phrases "in one embodiment," "in an embodiment," "in an aspect" and similar language throughout this specification may, but do not necessarily, all refer to the same embodiment.

Furthermore, the described features, structures, or characteristics of the methods and compositions provided herein may be combined in any suitable manner in one or more embodiments. In the following description, numerous specific details are provided, to provide a thorough understanding of embodiments. One skilled in the relevant art will recognize, however, that the embodiments may be practiced without one or more of the specific details, or with other methods, components, or materials. In other instances, well-known structures, materials, or operations are not shown or described in detail to avoid obscuring aspects of the embodiments.

Exemplary embodiments of the present disclosure are provided in the following examples. The examples are presented to illustrate the inventions disclosed herein and to assist one of ordinary skill in making and using the same. These are examples and not intended in any way to otherwise limit the scope of the inventions disclosed herein.

Example 1. Gene Delivery

The delivery of therapeutic genes or a distinct nucleic acid such as plasmid DNA, mini circle DNA, antisense oligonucleotides, RNAi, siRNA, shRNA and miRNA has numerous advantageous over existing treatment approaches due to the potential for permanently or temporarily repairing or replacing the abnormal or disease-causing genes, or supplying genes which are down-regulated for targeting specific cells. The treatment of diseases such as AIDS, hepatitis, cancer, fibrosis and diabetes may be possible by delivering therapeutic nucleic acids that modifies protein expression or silences an abnormal gene, to prevent the disease or reduce its severity. Researchers have been able to optimize the use of non-viral vectors to carry nucleic acids to cells for treatment of diseases, but although evidence of activity was observed with several non-viral delivery strategies, progress in clinical trials has not been effective.

Oral gene delivery using a non-viral carrier which is stable under a variety of different physiological and biological conditions, and which has a high oral absorption profile, is a challenge. Such gene delivery would have numerous advantages such as noninvasive delivery and patient convenience. However, the highly acidic fluid in the stomach may degrade a gene, mucosal fluids may attach to the gene and inhibit direct interaction with the GI tract membrane, or the gene may pass through the GI tract without absorption. Therefore, an optimized design which is compatible with the human physiological system is required for getting efficacy via absorption in the GI tract. Additionally, a shielding or wrapping strategy could protect the gene and also enhance absorption through small intestinal membrane, as well as facilitate absorption through both bile acid transporters such as the apical sodium dependent bile acid transporter (ASBT) and Ost alpha/beta receptors.

Cationic complexes having a modified surface for target specific delivery in the GI tract and an optimized vector/carrier system, were designed in order to achieve efficacy with minimal toxicity. Thus, a complex of the anionic gene and a cationic polymer was prepared using charge-charge interactions, and the complex was wrapped with a biocompatible and biodegradable polysaccharide that shielded the complex to provide protection from the GI tract.

Herein is described a therapeutic composition which contains a gene complexed with polyethylenimine and heparin. The outer surface of the composition was decorated with taurocholic acid which was covalently linked with the heparin to enhance oral absorption through bile acid transporters including the ASBT and the Ost alpha/beta transporters of the ilium in the small intestine.

Materials. Low molecular weight heparin (LMWH, average MW 5,000 kDa) was obtained from Mediplex Co., Ltd (Seoul, Korea). Taurocholic acid sodium salt (TCA), branched polyethylenimine (25 kDa), 1-ethyl-3-(3-dimethylaminopropyl) carbodiimide hydrochloride (EDAC), 4-nitrophenyl chloroformate (4-NPC), triethylamine (TEA), N-hydroxysuccinimide (HOSu), 4-methylmorpholine (MMP), 1,4-dioxane, 2% ninhydrin reagent and trypsin-EDTA were obtained from Sigma Aldrich Co. (St. Louis, Mo.). N,N-dimethylformamide (DMF), ethylenediamine, formamide, HEPES buffer and acetone were purchased from Sigma Chemical Co. (St. Louis, Mo.).

The oral administration of three genes was studied; a reporter plasmid gene of eGFP for a proof of principle study, and two therapeutic genes, one encoding Exendin-4, which is a commercial therapeutic peptide for type 2 diabetes and an agonist of glucagon-like peptide 1 (GLP-1), and one encoding GLP-1. An additional study was conducted with the Exendin-4 gene to determine its plasma levels after tail vein and oral administration.

The genes were complexed with branched polyethylenimine (bPEI), which has a net positive charge at a pH of 5. In one study, the complex was coated with chitosan (as a control sample) or a heparin-taurocholic acid (TCA) moiety (H-TCA or HTCA). This general scheme is shown in FIGS. 1B and 1C, which are schematic representations of a heparin-TCA wrapped complex (cationic polymer and gene complex) showing that the TCA locates on the outer surface of the composition due to its hydrophilic properties. In FIG. 1B, the bPEI is the B moiety and the gene is the A moiety.

B can be a DNA condensing agent and can have a positive charge at pH 5. A can be a plasmid DNA such as pEeGFP-N1, pGLP-1, or pEx-4). The polyanion-bile acid conjugate moiety can be heparin-TCA, and the BA moiety can be, for example, a bile acid such as cholic acid or deoxycholic acid, or it may be a bile acid conjugate, such as taurocholic acid or glycocholic acid. In FIG. 1C, the various components of the formulation are described in detail, including the core complex which is wrapped with the bile acid or bile acid conjugate covalently bound to an anionic polymer (here, anionic polymer is heparin and the bile acid conjugate is taurocholic acid).

The green fluorescence protein plasmid (pAcGFP1-N1, 4.7 kb) vector was obtained from Clontech (CA, USA). The Exendin-4 gene was obtained from Clontech (CA, USA) and amplified according to the protocol provided by the vendor.

Figure 39:
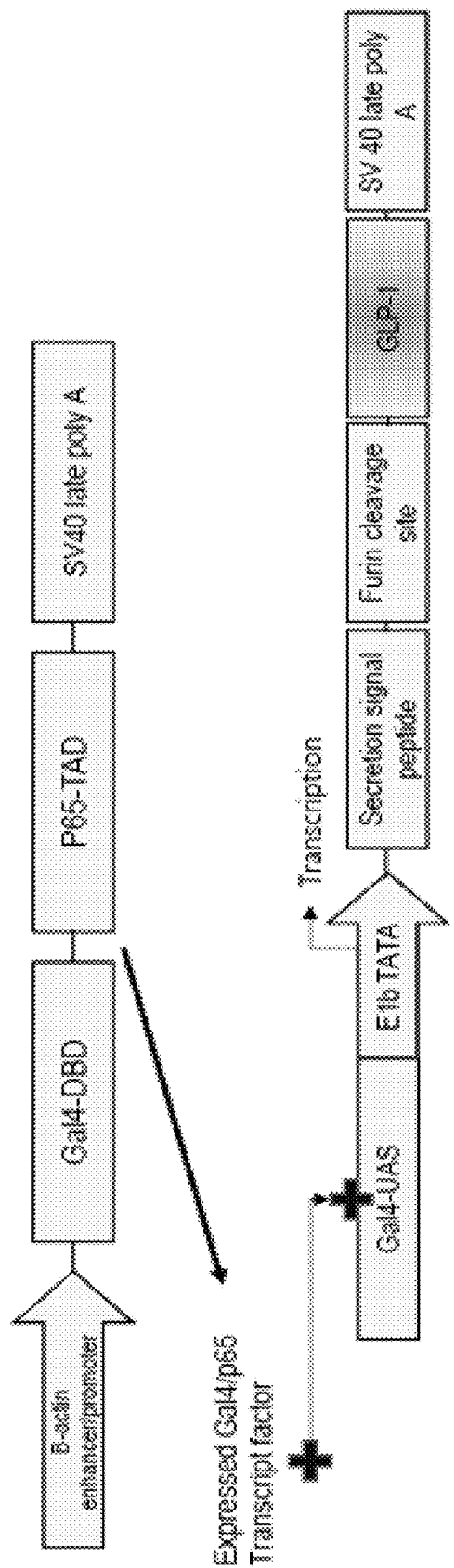
FIG. 39 shows a map of the glucagon like peptide-1 (GLP-1) gene structure used for the plasmid encoding GLP-1.

Glucagon like peptide-1 (GLP-1 cDNA) was synthesized chemically and inserted into the pβ vector at the KpnI and XbaI sites. The DNA fragment encoding the secretion SP was synthesized chemically and inserted into pβ-GLP-1 at the KpnI sites to create pβ-SP-GLP-1. The map of the GLP-1 gene structure used for the plasmid encoding GLP-1 is shown in FIG. 39.

To obtain activated TCA, 1 mol of taurocholic acid (TCA) sodium salt was dissolved in DMF (4.6 mL) at 0° C., and then TEA (6 mol) and 4-NPC (5 mol) were added to the flask. This solution was reacted for 1 hr under the same conditions, and was then stirred for 6 hr at room temperature. The solution was then centrifuged and extracted in a separatory funnel with absolute ethanol (EtOH) (20 mL) and DI water (20 mL), with the process repeated three times. The separated solution was placed in a rotary evaporator to evaporate organic solvent and was finally freeze dried for 48 hr to get a TCA-NPC powder. This TCA-NPC powder (1 mol) was dissolved in DMF (5 mL) and 4-MMP (2 mol) was added. This reaction was continued for 1 hr at 50° C. After 1 hr, EDA (100 mol) was added drop-by-drop to the solution and stirring was continued for 16 hr at room temperature. The crystallized part was filtered and was dried with a vacuum dryer. To synthesize the HTA conjugate, 1 mol of heparin was dissolved in distilled water with gentle heat and 0.1 M of HCl was added to maintain the pH in the range of 5.5-6. EDC (5 mol) was added to the heparin solution, which was stirred for 5 min, and then NHS (7 mol) was added, again stirring for 30 min.

In this manner, heparin and TCA were covalently coupled together by modification of the end hydroxyl group of TCA to introduce an amine group, which was conjugated with a carboxyl group of heparin through an amide bond. By optimizing and controlling the feed mole ratio and reaction conditions, the coupling ratio was optimized to 4 mole of TCA to each mole of heparin. The heparin-TCA moiety was purified by dialysis and characterized by H-NMR and FT-IR to confirm covalent bonding. The bonding between the TCA and heparin was confirmed by the observation of a new proton peak at 7.2 ppm by NMR analysis.

The (bPEI/pDNA) complex and the bile acid coating were prepared as follows. Branched polyethylenimine (bPEI, 25 K, 10 mM) was dissolved in 100 mL HEPES buffer and vortexed until the solution became clear and transparent. In a separate vial, the required amount of pDNA was mixed with HEPES buffer (10 mM) to provide a concentration of 1 mg/mL. The gene containing solution was drop-wise added to the bPEI solution in a ratio of N/P of 1/1, 2/1, 5/1 and 10/1 with gentle vortexing, where N represents the ionizable cationic groups in the polymer and P represents the phosphate group in the gene. The mixtures were kept at room temperature for 30 min allowing the complex to form through charge-charge interaction. At an N/P ratio of 5/1, the zeta potential value of the complex was measured at about +10 mV. The negatively charged heparin-TCA moiety was dissolved in HEPES (1 mg/mL) in a separate falcon tube. The previously prepared cationic (bPEI/pDNA) complex was drop-wise added to the heparin-TCA solution in a ratio of 1:1 (v/v). The final formulation was kept for 30 min at room temperature to form the heparin-TCA coated complex. The final composition was lyophilized by freeze drying over 2 days.

The morphology and size of the cationic (bPEI/pDNA) complexes and the heparin-TCA wrapped compositions were investigated by TEM and DLS, respectively. Zeta potential measurements were conducted to observe surface properties to optimize the ratio of cationic polymer, gene and heparin-TCA. The formulations were dissolved in distilled water (1 mg/mL) with vortexing before measuring by DLS and Zeta analyzer.

Figure 2:
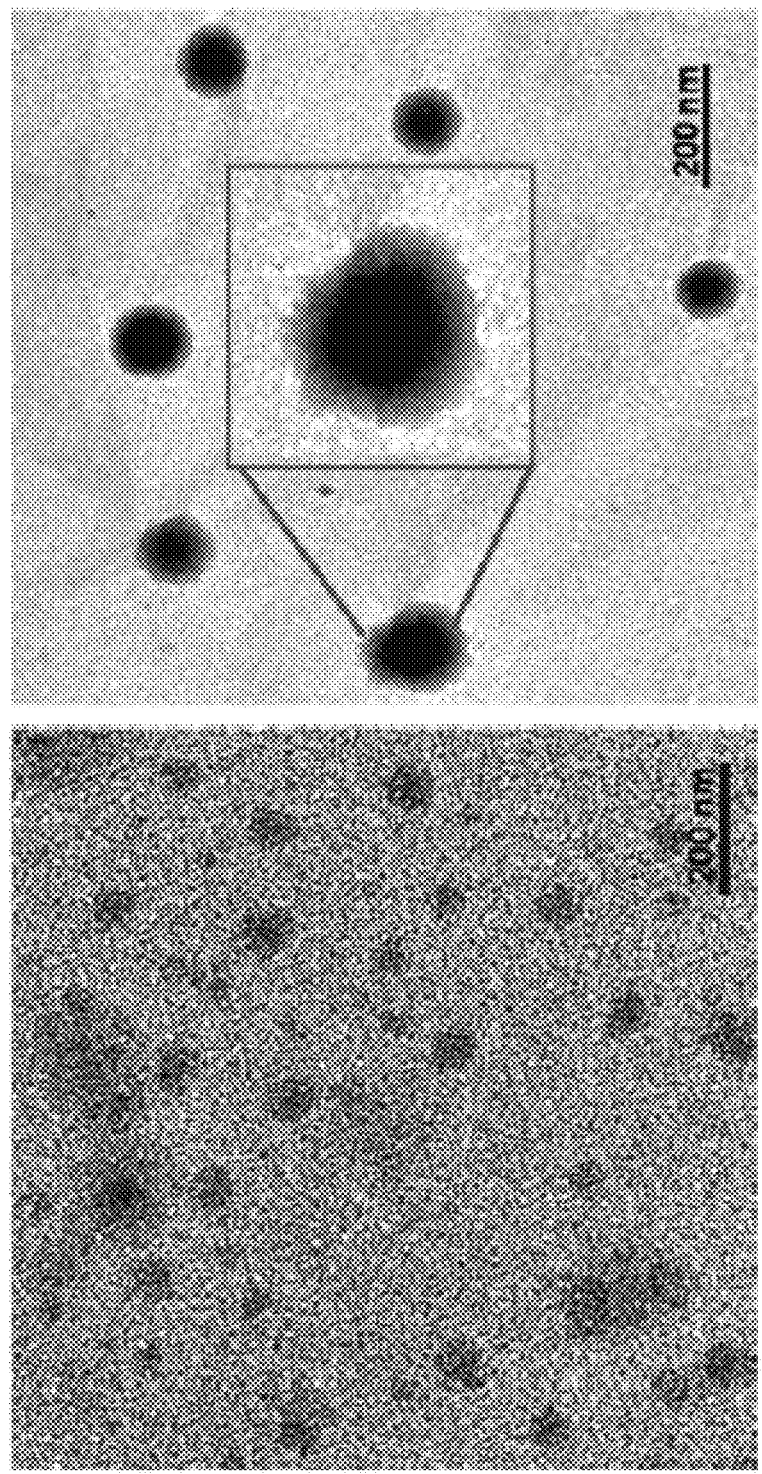
FIG. 2 shows transmission electron microscope (TEM) images of an exemplary complex (left) and an exemplary composition (right).

FIG. 2 is transmission electron microscope (TEM) images providing information on the size and morphology of two samples. A sample of a cationic (bPEI/pDNA-N1) complex is shown in the left image of FIG. 2, and a sample of a cationic (bPEI/pDNA-N1) complex wrapped with heparin-TCA is shown in the right image of FIG. 2, with the inset showing an enlarged nanoparticle with the HTCA coating. As can be seen, the size of the complex is approximately 100 nm, and the wrapped composition is approximately 200 nm.

The negatively charged eGFP gene and the positively charged bPEI contact each other when dissolved in HEPES buffer and form a complex through charge-charge interactions, due to the electrostatic attraction between the cationic polymer and the anionic gene. The size of the complex depends on the N/P ratio of gene (N) and bPEI (P). The formation of a complex between the gene and polymer was confirmed through size distribution analysis and gel electrophoresis.

The characterization of the cationic (bPEI/pDNA-N1) complexes show that those with an N/P ratio of 5/1 and 10/1 have a cationic surface with a similar zeta value and size, approximately +12 mV and approximately 100 nm in diameter, measured by DLS and TEM. The complex with an N/P ratio of 5/1 was chosen for coating with anionic heparin-TCA.

Five different weight ratios of cationic (bPEI/pDNA) complexes and heparin-TCA were studied to formulate the optimum composition in terms of neutral charge and minimum size. Branched polyethyleneimine (bPEI, 25 K, 10 mM) was dissolved in 100 mL HEPES buffer and vortexed until a clear solution was observed. In a separate vial, appropriate volumes of pDNA were diluted with 10 mM HEPES buffer to get a final concentration of 1 mg/mL. Gene formulations with the following different N/P ratios, 1:1, 1:2, 1:5, and 1:10, were synthesized by adding diluted gene formulations to bPEI under gentle vortex. The samples were slightly agitated at room temperature for 30 minutes to stabilize the electrostatically coupled bPEI-gene complex. The heparin-TCA conjugates (1 mg/mL) at a 1:1 volume ratio were drop-wise added to the initially formed complexes and kept at room temperature for 30 min to obtain a stable heparin-TCA coated composition. The composition was lyophilized for 2 days.

Figure 3:
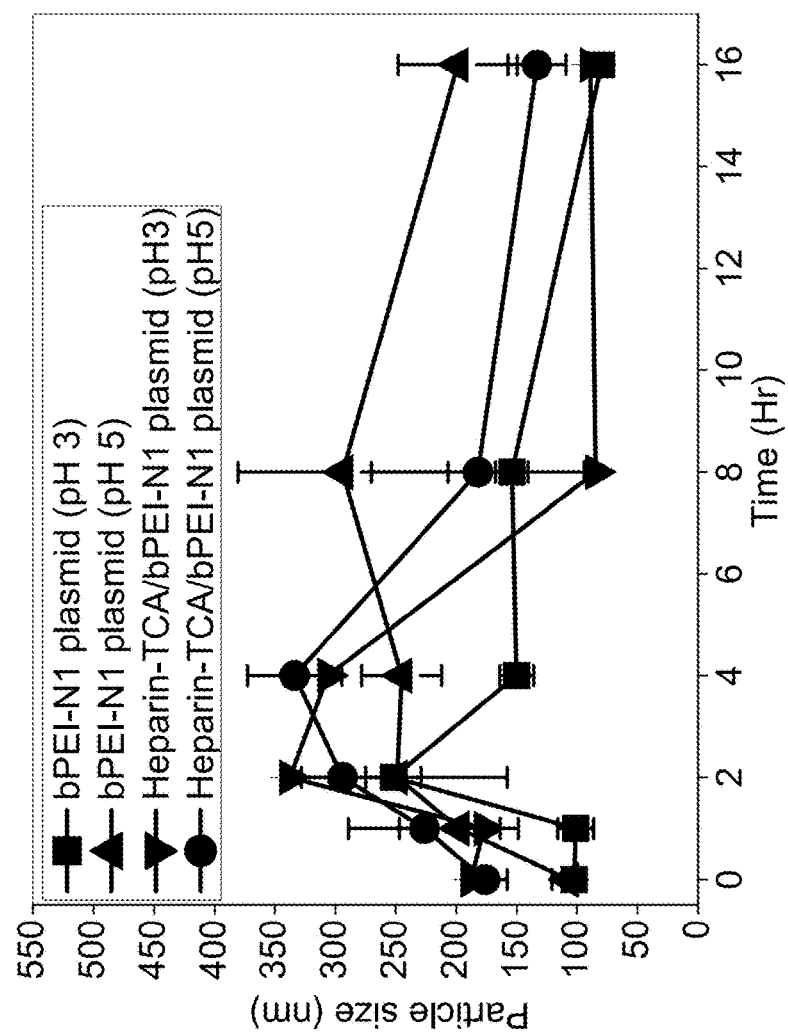
FIG. 3 is a graph of the particle size over time for an exemplary complex and an exemplary composition under two pH conditions.

FIG. 3 shows the stability of the particle size over time in buffers with two pH values. The data has a mean±SD, n=5. The formulation was prepared with pDNA-N1 and lyophilized for two days. The powder was re-dispersed in phosphate buffer solution and the pH was adjusted (pH 3) by adding HCl (1 N). The formulation preparation and the analysis of the formulation were performed at room temperature. The stability of both the cationic complex and heparin-TCA wrapped complex was observed by measuring the size and zeta potential values in aqueous solutions for up to 6 days. The measured zeta potential values were in the range of between about −20 to about 10 mV. This data confirms that the particles are stable, since the changes in size are not significant and the zeta values were maintained in the optimum range.

Figure 4A:
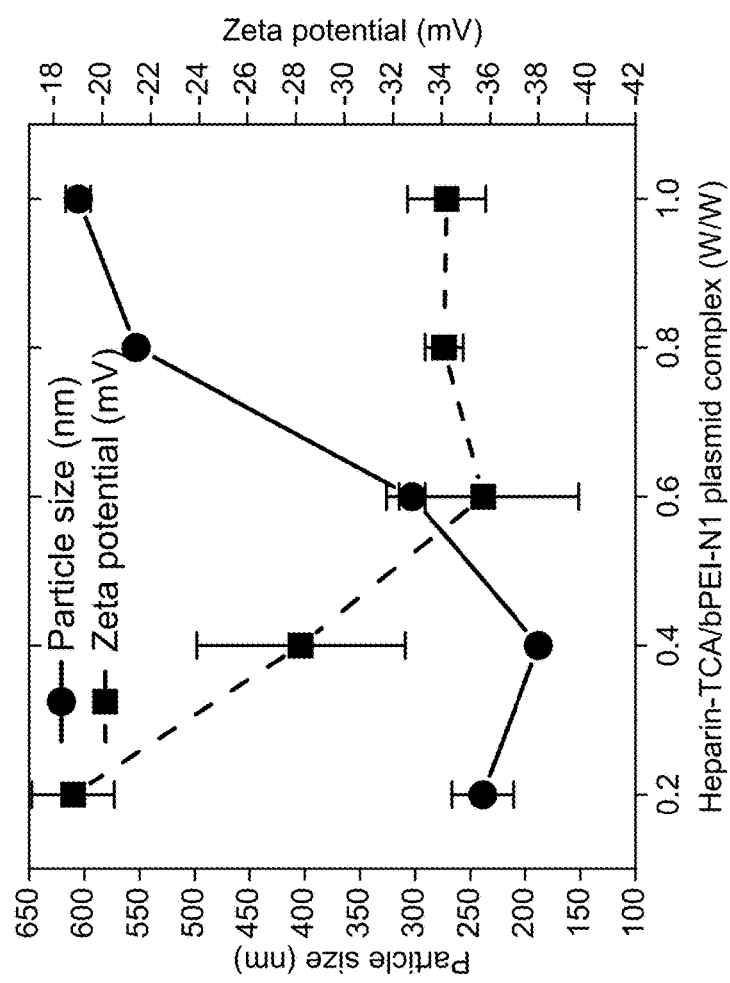
FIGS. 4A-4B are graphs of (FIG. 4A) the particle size and zeta potential with varying ratios of complex to conjugate, and (FIG. 4B) over time, of exemplary compositions.
Figure 4B:
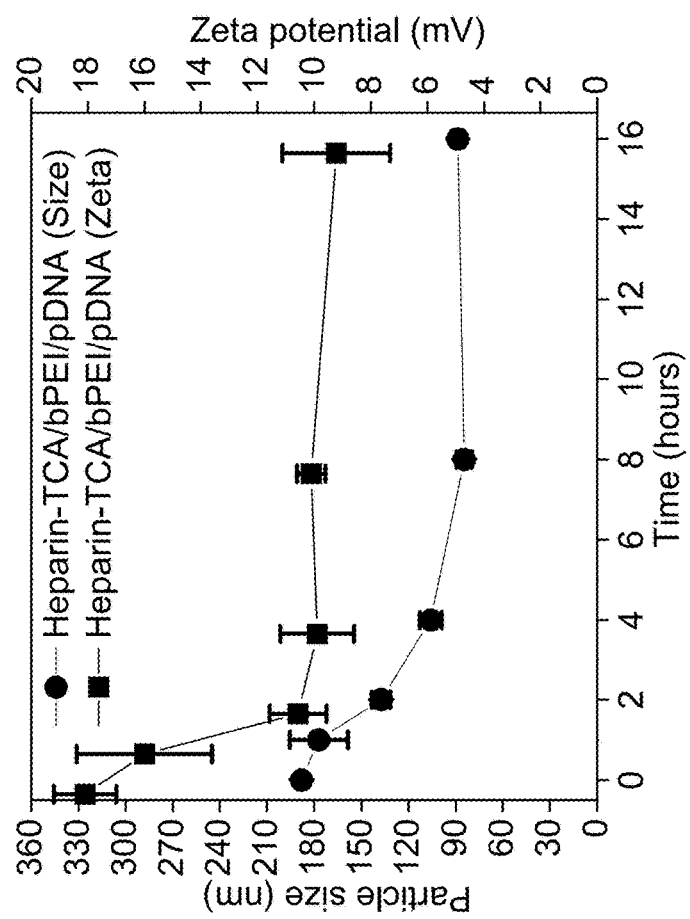

FIG. 4A is a graph of the particle size and zeta potential with varying ratios of the amount of cationic (bPEI/pDNA-N1) complex and bile acid coupled heparin. The HTCA/cationic complex ratios studied (all by weight) were 0.2, 0.4, 0.6, 0.8, and 1. The data has a mean±SD, n=5. The size and zeta stability of the heparin-TCA wrapped complex (with the 0.2 w/w ratio) was observed for 16 hours at pH 3, and is shown in FIG. 4B.

The highest heparin-TCA ratio tested (1/1) shows a larger size distribution profile with a large negative zeta potential value (more than −35 mV). As is seen by the data shown in FIG. 4A, the size of the complex/bile acid particles increased by about 150-500 nm in diameter, as the complex is around 100 nm and the heparin-TCA wrapped complex particles are between about 250 and 600 nm in diameter. Over the same time, the zeta potential went to negative values, which indicates that the surface of the cationic complex was wrapped with anionic heparin-TCA. The heparin-TCA wrapped complex particles were analyzed for zeta potential, which showed that they were highly negative (−20-25 mV).

Figure 5A:
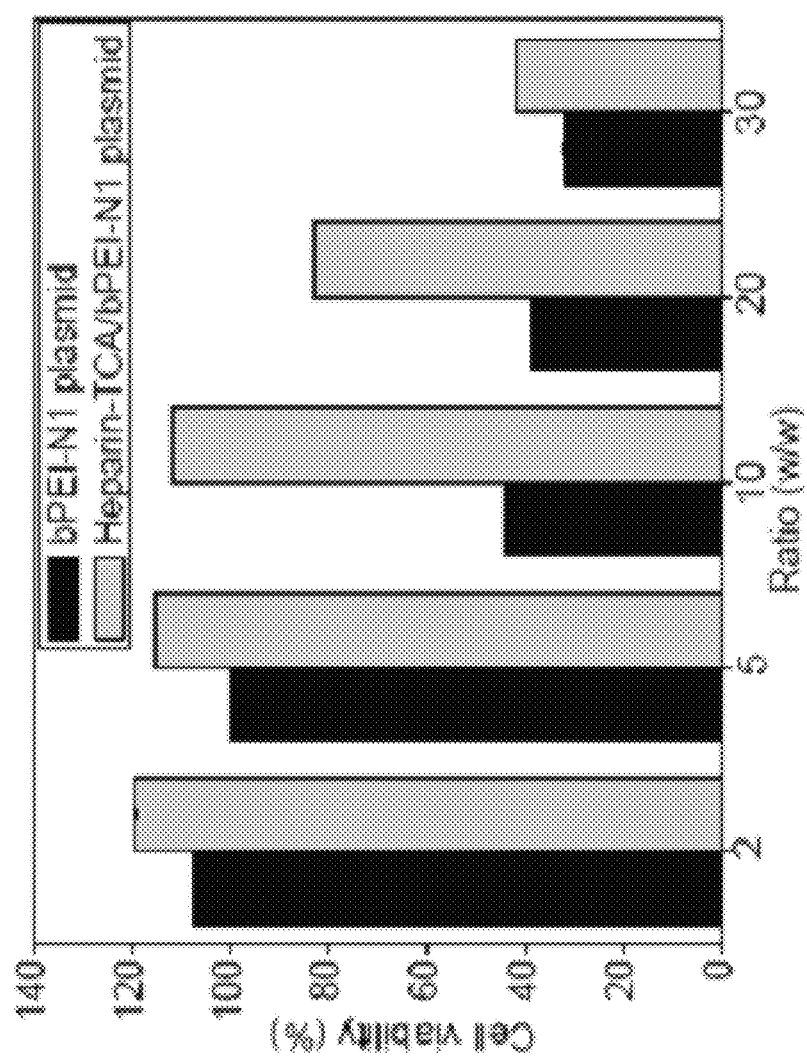
FIGS. 5A-5B are graphs of the toxicity of exemplary complexes and compositions with varying ratios of complex to conjugate in (FIG. 5A) EaHy926 cells and (FIG. 5B) HepG2 cells.
Figure 5B:
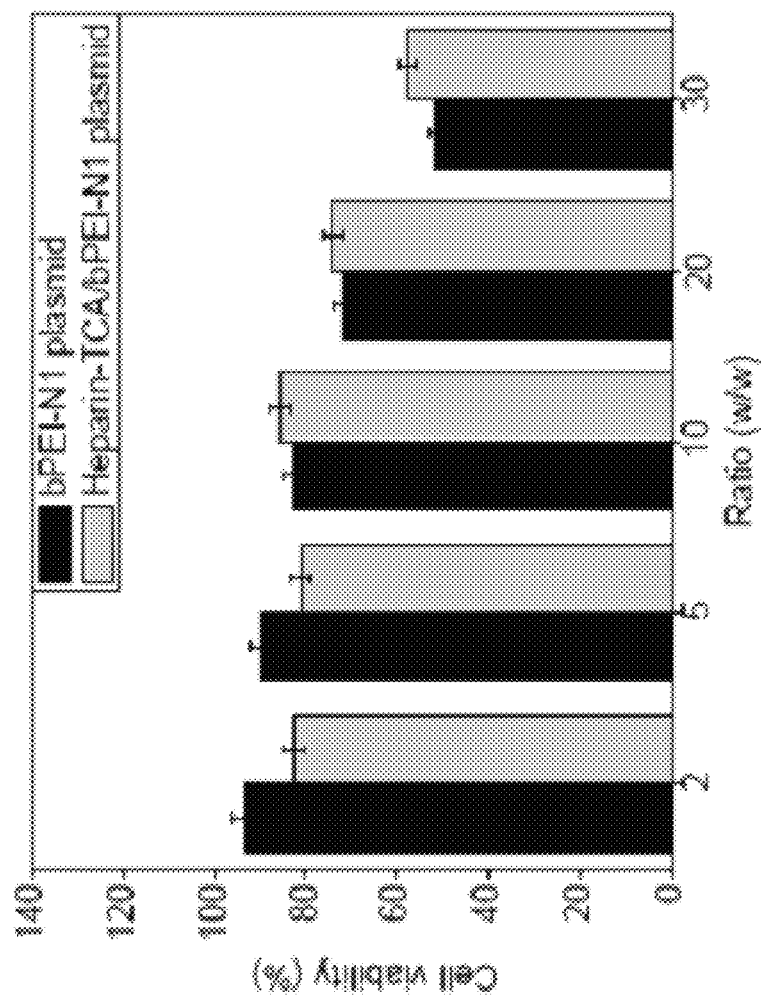

In vitro toxicity study expression studies. To investigate the cytotoxicity of the cationic (bPEI/pDNA-N1) complexes and the heparin-TCA wrapped compositions, they were co-cultured for 24 hr with EaHy926 and HepG2 cells. Cationic (bPEI/pDNA-N1) complexes with different N/P ratios (2/1, 5/1, 10/1, 20/1 and 30/1) with and without a heparin-TCA coating were incubated with EaHy926 and HepG2 cell lines for 24 h to observe in vitro cytoxicity. The cell viability was assessed by an MTT assay. The graph in FIG. 5A shows the cytotoxicity results in EaHy926 cells, and the graph in FIG. 5B shows the results in HepG2 cells. The data has a mean±SD, n=5.

The results shown in FIGS. 5A and 5B indicate a difference in the cell viability profile between EaHy926 and HepG2 cell lines. Generally, the formulations are slightly more toxic to EaHy926 cells than to the HepG2 cells. However, generally less cell viability (i.e. more toxicity) was observed in both cell lines for the cationic (bPEI/pDNA) complex than the heparin-TCA wrapped compositions. This may be attributed to the exterior heparin-TCA wrapping protecting the cells from the toxicity of bPEI by preventing the release of bPEI over a certain period of time. The formulations with an N/P ratio of 5/1 do not show much toxicity in both of the cell lines, either with or without the heparin-TCA coating. However, formulations with an N/P ratio of 10/1, 20/1 and 30/1 show more toxicity in the EaHy926 cell line compared to HepG2, but after wrapping with a biocompatible bile acid, the cell viability of all formulations increased.

Figure 6A:
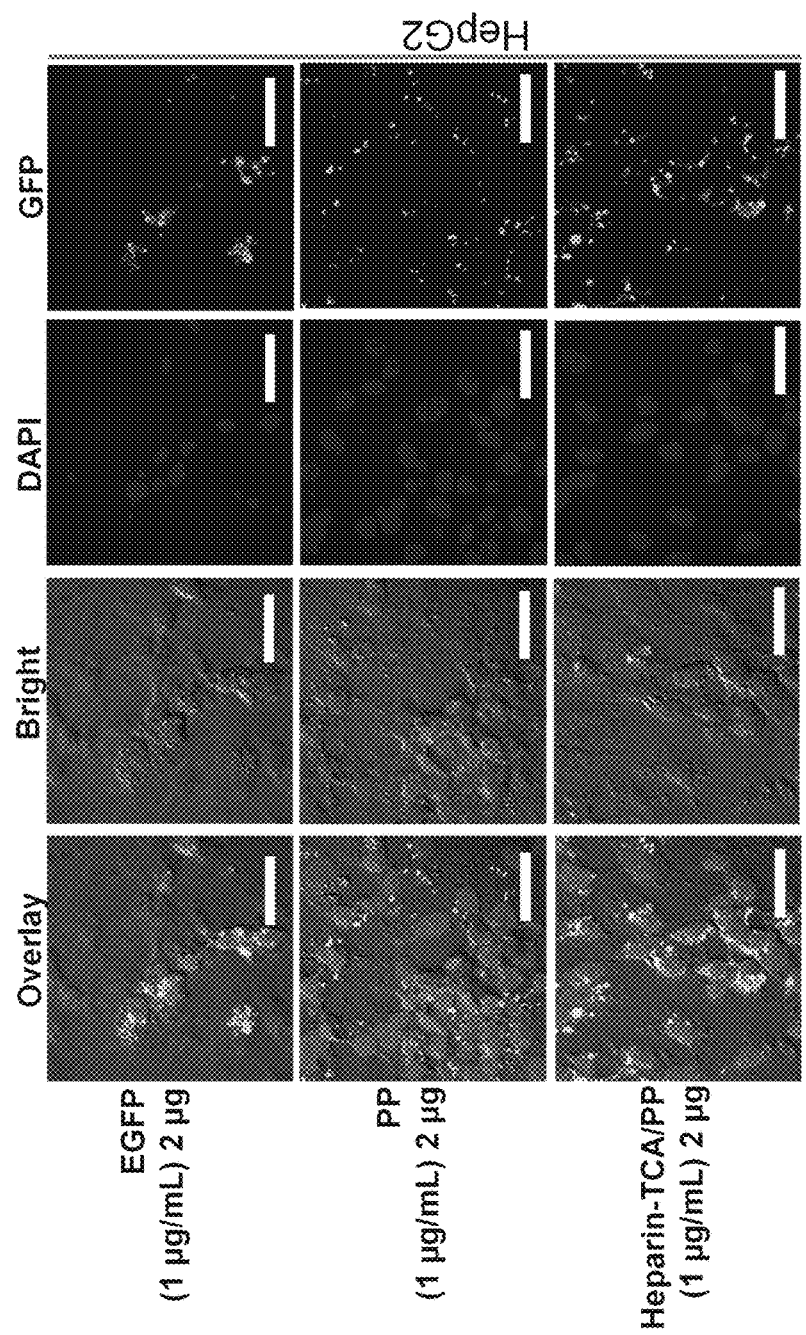
FIGS. 6A-6B are fluorescent images showing the expression of eGFP in exemplary complexes and compositions containing the gene for eGFP in (FIG. 6A) HepG2 cells and (FIG. 6B) EaHy926 cells. The scale bar is 20 um.
Figure 6B:
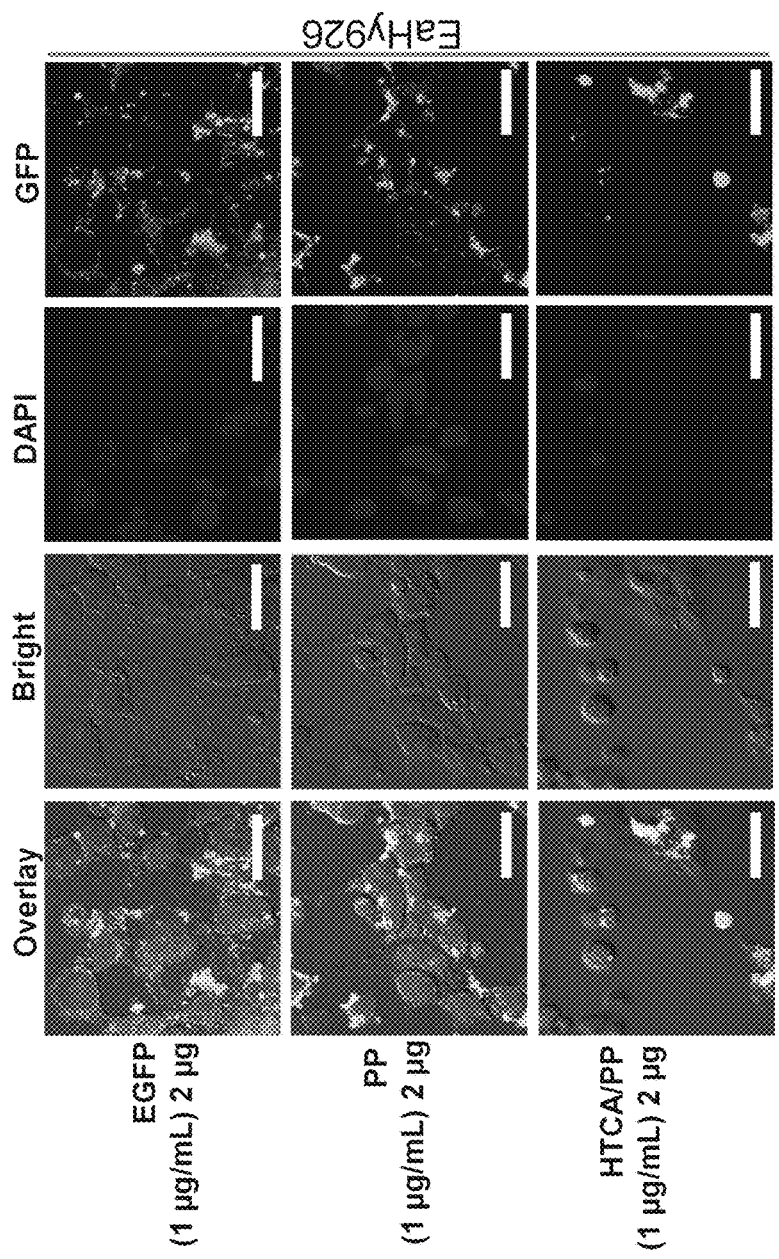

Each of the EaHy926 and HepG2 cell lines were incubated with samples of saline, the free eGFP gene, the cationic complex, and the heparin-TCA wrapped composition to investigate the comparative expression profile of eGFP. The cells were incubated for 24 hr with a concentration of eGFP of 2 rig/well, and the nucleus was stained with DAPI to determine the expression level at the intracellular level. The results of the 24 hr incubation with 2 μg/well of eGFP are shown in FIG. 6A for the HepG2 cell line, and in FIG. 6B for the EaHy926 cell line. EGFP represents the free gene, PP represents the cationic complex, and HTCA/PP represents the heparin-TCA wrapped cationic composition. The heparin-TCA wrapped cationic composition was less cytotoxic and did not cause any acute problems with animals after either IV or oral administration.

GFP expression was directly observed by confocal microscopy after 24 hr of incubation. The confocal microscopic images of cells demonstrate that the heparin-TCA wrapped compositions show the most expression, with the cationic complex showing lower expression than the heparin-TCA wrapped compositions but higher expression than free eGFP. The expression of free eGFP is attributed to a small amount of free gene accumulating into the cells, as evidenced with direct imaging.

Real time monitoring of bile acid oral absorption and biodistribution. Before the oral delivery of gene formulations was studied, experiments were conducted with optical imaging contrast agent quantum dots (QD) linked with taurocholic acid (TCA) to investigate the oral absorption profile in mice in real time. Carboxylated QDs were conjugated with TCA-NH$_2$ in presence of the coupling agents EDC and NHS. Characterization was confirmed that the QD and TCA were linked through an amide bond, as a confirmation peak appeared in the proton NMR spectrum. The compounds were dialyzed against water (MWCO-1000) to remove the unbound TCA and freeze dried for lyophilization. The resultant powder was dispersed in buffer and administered to the animals by oral gavage. The mice were fasted for 12 hours prior to dosing, and the oral administration was done with a dose of 2.5 mg/kg, with each group containing 5 mice. The mice dosed with the TCA-linked QD were imaged for a few hours using an optical imaging monitoring system.

Figure 7A:
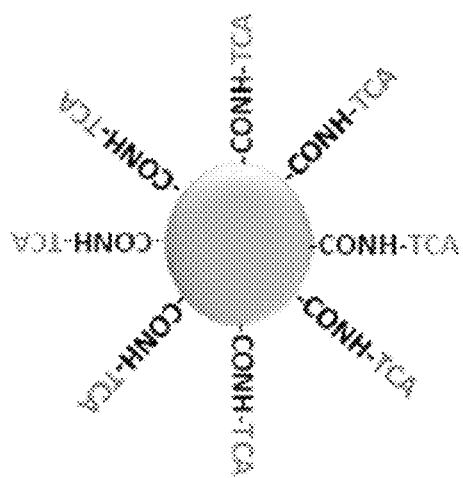
FIG. 7A is a schematic illustration of a taurocholic acid-linked quantum dot (QD-TCA), showing how the TCA is linked at the exterior of the quantum dot.
Figure 7B:
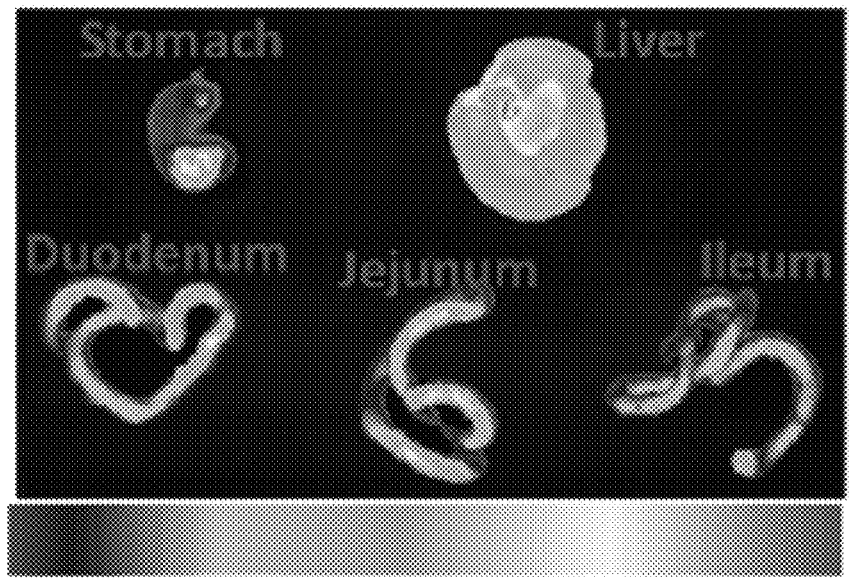
FIG. 7B is an ex-vivo optical imaging profile of various murine organs after treatment with QD-TCA.

FIG. 7A is an illustration of the structure of a TCA-linked QD. FIG. 7B shows the ex-vivo optical imaging profile of five organs of mice treated with QD-TCA. As shown in FIG. 7B, the QD-TCA is primarily localized in the liver and jejunum. For this quantitative real time observation in terms of biodistribution and organ localization, QD technology was used. The mice were sacrificed and dissected 24 hr after oral administration of the QD-TCA formulation. The selected organs were sectioned as 15 μm thin and embedded on TEM grid for observation and localization of the QD, in both a comparative quantitative and qualitative analysis.

Figure 8:
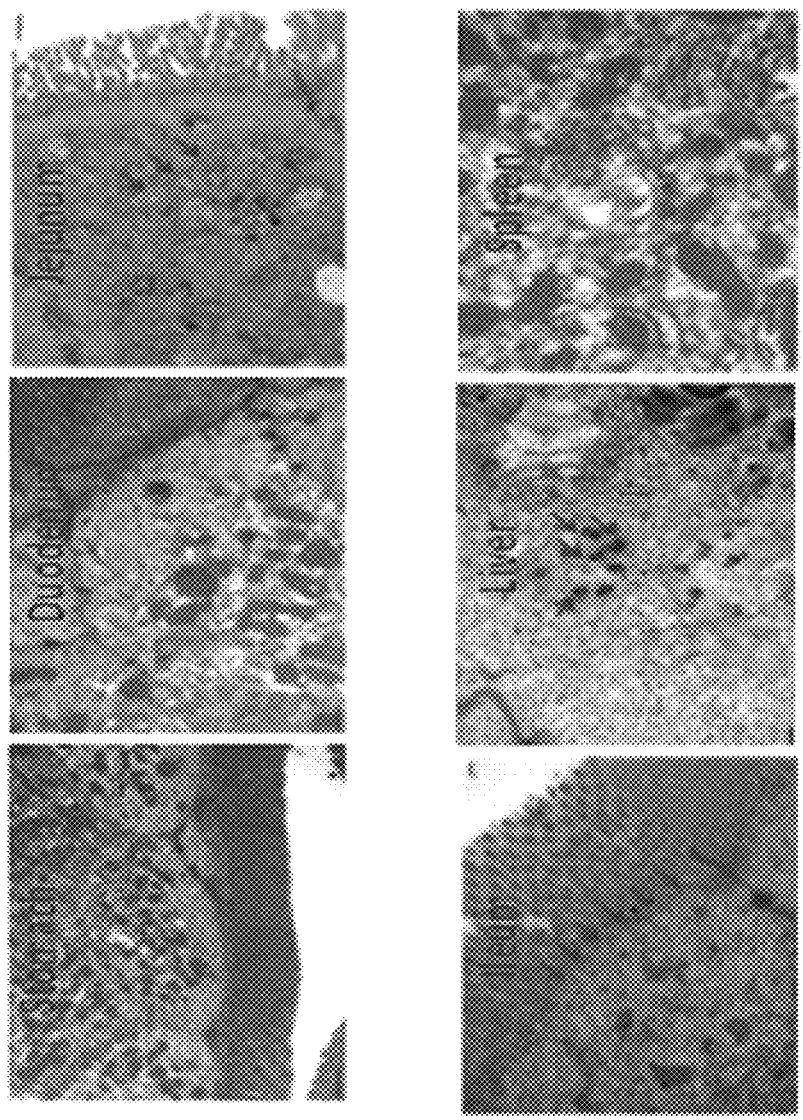
FIG. 8 is a series of TEM images showing the presence of QD-TCA in various tissues after treatment of the mice with QD-TCA. The QD-TCAs are identified by the arrow. The top images show tissue from the stomach, duodenum and jejunum; the bottom images show tissue from the ileum, liver and spleen.

FIG. 8 is TEM images of the stomach, duodenum, and jejunum (upper images), and the ileum, liver and spleen (lower images), which indicate the presence of a significant number of QDs in the ileum and liver of the mouse after oral administration of QD-TCA.

Oral delivery, biodistribution and optical imaging. An oral absorption feasibility study of the (bPEI/pDNA-N1, 5/1) cationic complex and the (complex/HTCA 1/0.2) heparin-TCA wrapped composition was conducted in mice (C57BL6). Five mice which were each approx. six weeks old with an average body weight of 17 g, were purchased from Simonson Bio (UT, USA). The animals were fasted overnight prior to oral administration of the formulations. The formulations were adminstered at a dosage of 2.5 and 5 mg/kg (200 μL). The animals were dissected and organs were isolated 24 and 48 hr after oral administration.

Specific organs were collected, those being the small intestine (jejunum, duodenum, and ileum), lung, liver, heart, kidney and spleen, and there organs were prepared for cryo-sectioning. After isolation, the organs from the mice were fixed with paraformaldehyde solution (4%) before paraffin embedding. The 15-μm thick tissues from the paraffin blocks were placed on a glass slide (dried in vacuum oven before observation was conducted) and analyzed. Images were taken with a confocal microscope to observe the expression of eGFP with scanning by a 488 nm excitation filter.

For the optical imaging study, five nude mice which were each approx. six weeks old with an average body weight of 25 g, were purchased from Dae Han Bio-link (Korea). The mice were fasted for 24 hr prior to oral administration of the cationic complex and the heparin-TCA wrapped composition. For the quantitative analysis of light, photons were also measured by a fluorescence (FL) analyzer (Varioskan Flash, Thermo Scientific, CA, USA). The isolated organs were washed with buffer and immediately frozen in liquid nitrogen. The following day, the organs were defrosted and stored on ice. After weighing, all organs were homogenized for 20 seconds on ice in 0.5 mL of reporter lysis buffer using a tissue homogenizer. Then, the resulting tissue homogenates were left on ice for 1 hr. The tissue solutions were vortexed for 20 seconds and subsequently centrifuged at 13,000 g for 10 min. Twenty-four hours after administration, the mice were dissected and organs were isolated. The organs were sliced by paraffin blocking and images were taken with a confocal microscope to observe the expression of eGFP. The scanning laser excitation and emission filters were at 488 nm and 510 nm, respectively.

Four formulations were prepared and studied to observe the comparative biodistribution profile of eGFP pDNA after 24 hr of administration in mice. The five formulations were (1) the cationic (bPEI/eGFP) complex which contained no bile acid or bile acid conjugate (administered orally); (2) a chitosan wrapped anionic eGFP formulation which contained no bile acid or bile acid conjugate (administered orally); (3) a heparin wrapped cationic (bPEI/eGFP) complex which contained no bile acid or bile acid conjugate (administered orally); and (4) the heparin-TCA wrapped (bPEI/eGFP) complex (administrated both IV and orally), with the ratio of complex/chitosan, heparin and HTCA all being 1/0.2 (w/w).

Figure 9:
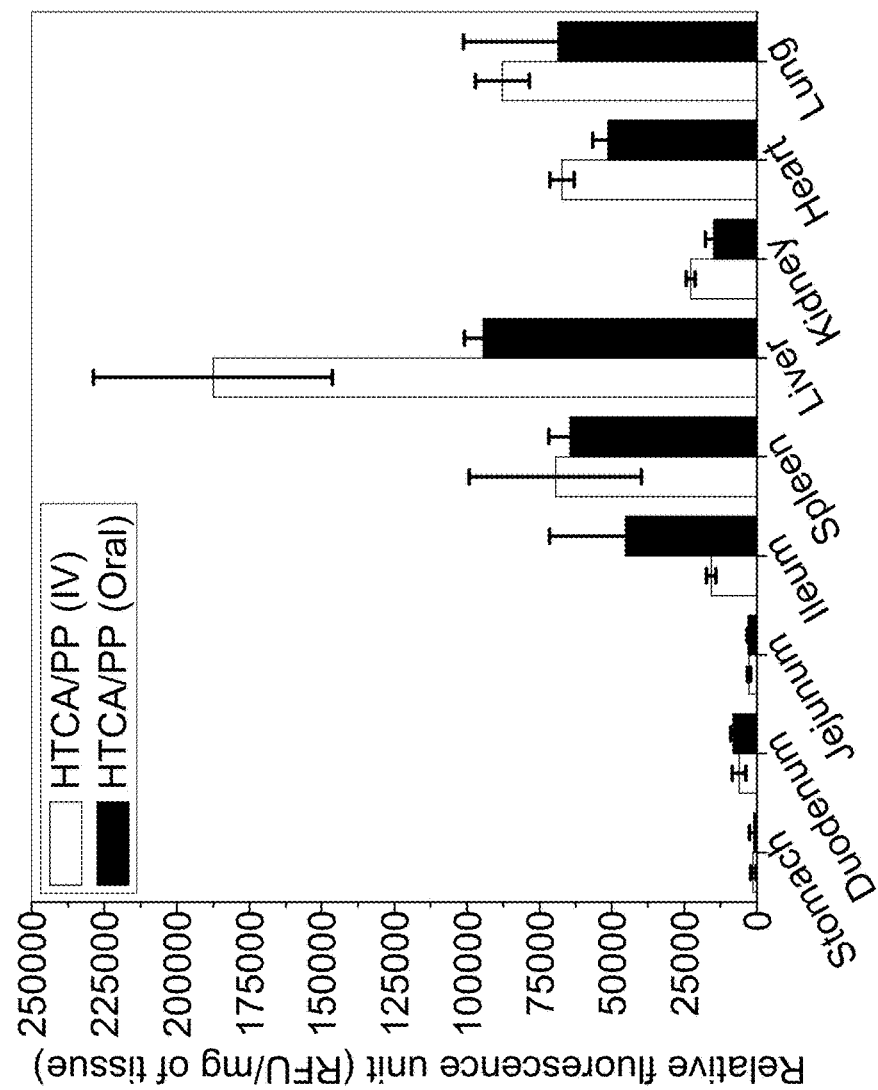
FIG. 9 is a bar graph showing the relative amount of fluorescence arising from eGFP in certain murine organs after IV and oral administration of an exemplary composition.

FIG. 9 shows a bar graph with the relative biodistribution analysis of orally and intravenously administered eGFP-plasmid DNA shielded by heparin-TCA (formulation 4). The data represents mean±SD, n=4. The relative amount of fluorescence arising from the eGFP present in certain organs was analyzed after IV (open bars) and oral (filled bars) administration to a mouse.

Figure 10:
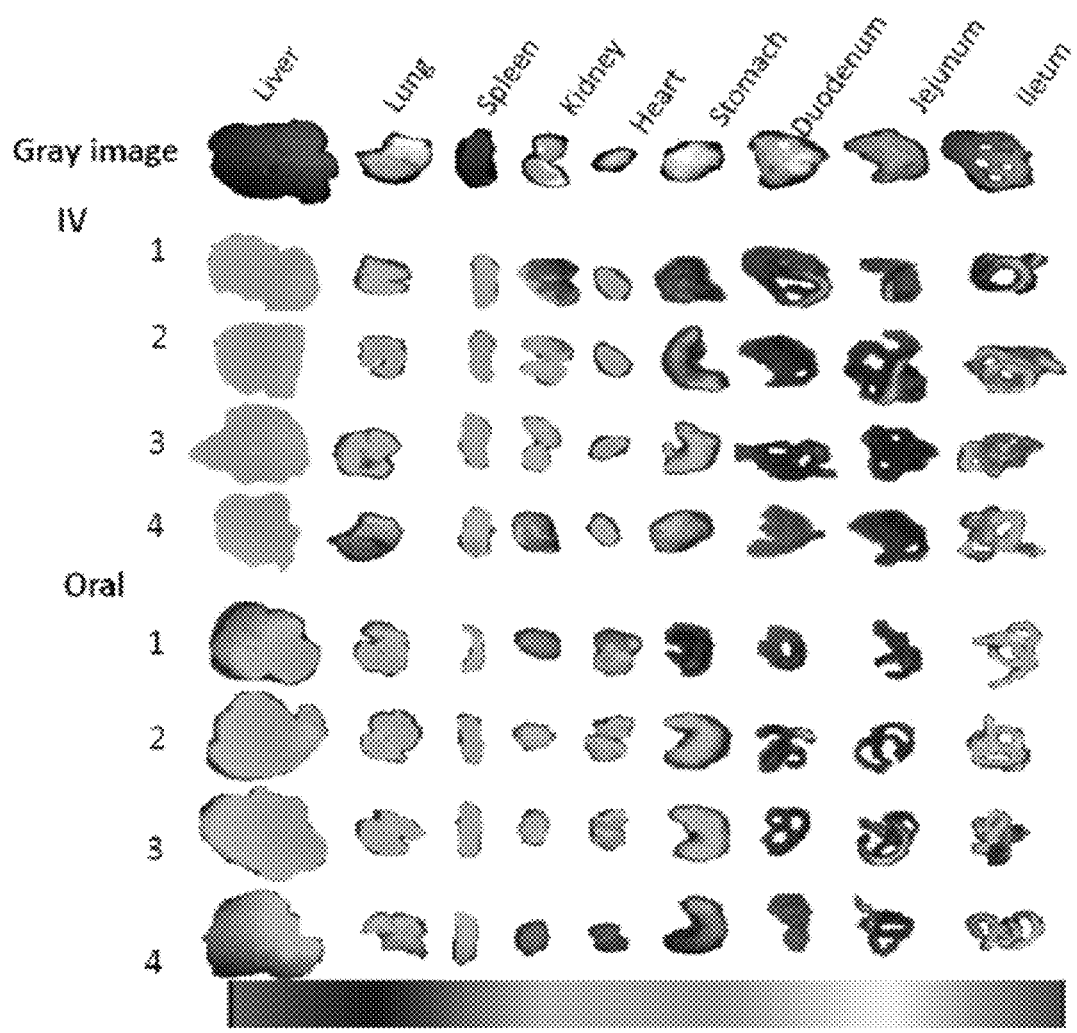
FIG. 10 shows the amount of eGFP present in certain organs after IV (upper rows) and oral (lower rows) administration of an exemplary composition to mice.

FIG. 10 shows the optical imaging of different organs of the mice when GFP expression was directly observed, after the IV (upper rows) and oral (lower rows) administration of eGFP-plasmid DNA shielded by heparin-TCA (formulation 4).

Figure 11:
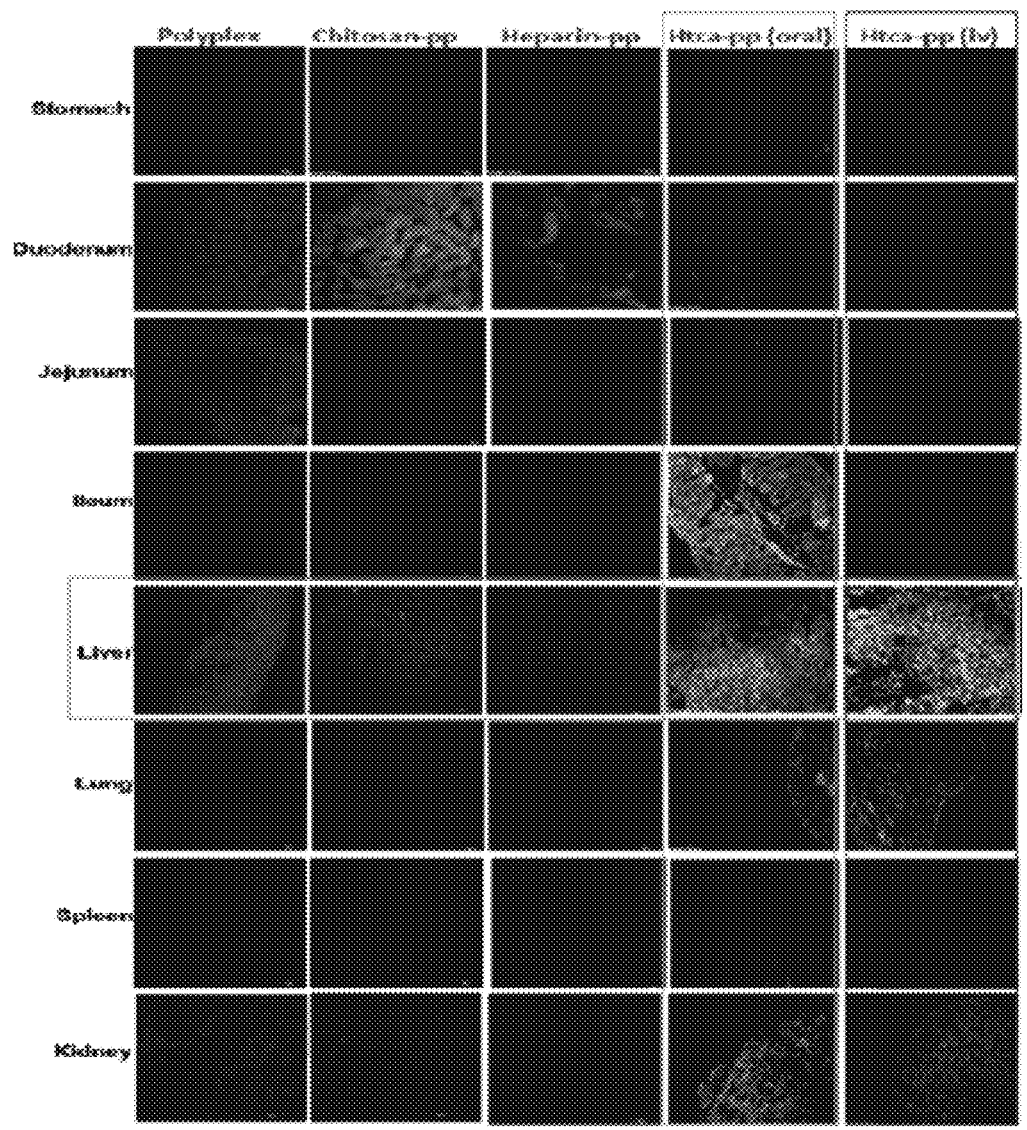
FIG. 11 shows a series of confocal images showing the amount of eGFP present in various murine organs after administration of five exemplary formulations.

FIG. 11 shows confocal images of 8 organs after administration of the four formulations, as labeled. The first column of images is after oral administration of the cationic (bPEI/eGFP) complex which contained no bile acid or bile acid conjugate (formulation 1, "polyplex"); the second column of images is after oral administration of the chitosan eGFP formulation which contained no bile acid or bile acid conjugate (formulation 2, "chitosan-pp"); the third column of images is after oral administration of the heparin wrapped cationic (bPEI/eGFP) complex which contained no bile acid or bile acid conjugate (formulation 3, "heparin-pp"); the fourth column of images is after oral administration of the heparin-TCA wrapped (bPEI/eGFP) complex (formulation 4, "htca-pp (oral)"); and the fifth column of images is after intravenous (IV) administration of the heparin-TCA wrapped (bPEI/eGFP) complex (formulation 4, "htca-pp (iv)"). The first row of images shows the fluorescence in the stomach, the second row are for the duodenum, the third row for the jejunum, the fourth row are for the ileum, the fifth row are for the liver, the sixth row is for the lung, the seventh row is for the spleen, and the eighth row is for the kidney.

Figure 12:
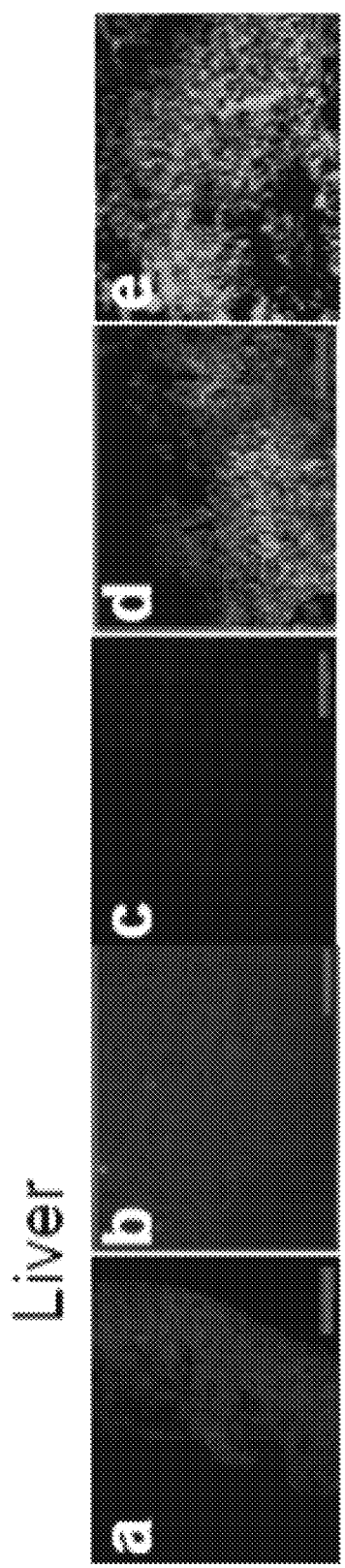
FIG. 12 is one row of the images of FIG. 11, expanded.
Figure 13:
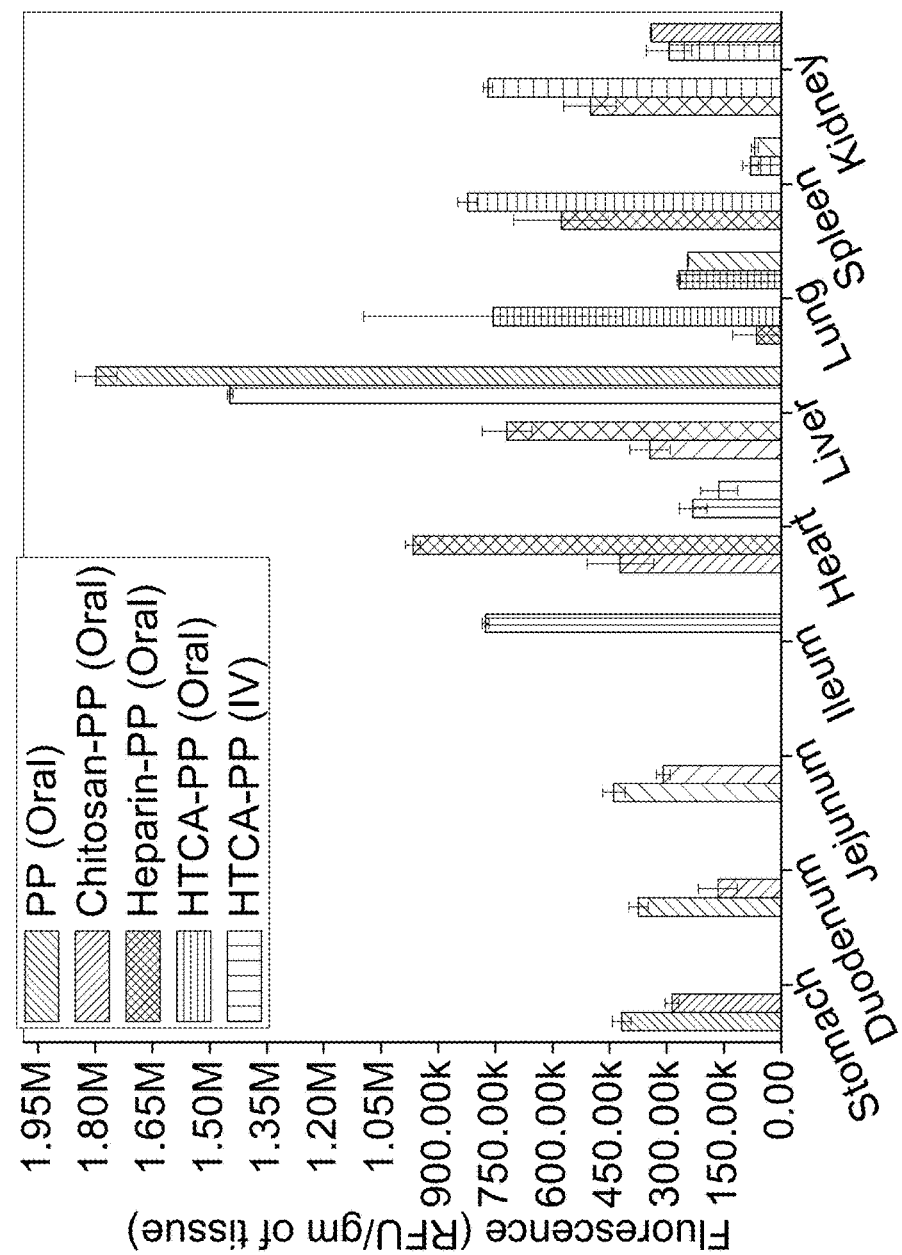
FIG. 13 is a graph of the relative fluorescence after administration of exemplary formulations in various murine organs.

FIG. 12 is an expanded view of the five images for the liver (the fifth row) from FIG. 11. The red bar corresponds to 100 nm. FIG. 13 is a graph of the relative fluorescence for each formulation in nine organs, providing the quantitative values of the images shown in FIGS. 11 and 12.

The images show that the heparin wrapped cationic (bPEI/eGFP) complex which contained no bile acid or bile acid conjugate (formulation 3) did not significantly absorb into the animal, as little evidence of eGFP expression was observed by either direct imaging or FL analysis (column 3 of FIG. 11). Thus, no eGFP expression in any organ was monitored for this formulation. FIG. 11 shows that a portion of formulation 1 (the cationic (bPEI/eGFP) complex which contained no bile acid or bile acid conjugate) and a higher amount of formulation 2 (the chitosan eGFP formulation, which contained no bile acid or bile acid conjugate) absorbed non-specifically through the stomach and small intestine, especially in the duodenum.

The heparin-TCA wrapped (bPEI/eGFP) complex (formulation 4) was specifically absorbed through the ileum since expression of eGFP was observed strongly in the ileum by both direct imaging and FL analysis. The ileum contains significantly more bile acid and Ost alpha/beta transporters than other parts of the GI tract, and should show an increased absorption of bile acid linked formulations compared to the other formulations.

The IV administration of the heparin-TCA wrapped (bPEI/eGFP) composition (formulation 4) shows the highest bioavailability and accumulation in liver. The heparin-TCA carrier shows significant expression in the different organs with bile acid transporter mediated specific absorption.

The comparative quantitative and qualitative expression data shown here demonstrate that expression of eGFP varies based on the carrier and administration route, and the degree of expression varies from organ to organ. In particular, results from the oral delivery of the heparin-TCA wrapped (bPEI/eGFP) composition (formulation 4) are consistent with absorption occurring through the bile acid transporters and Ost alpha/beta transporters in the ileum and liver, as the maximum accumulation of the eGFP was found in the liver as indicated by the high level of intensity of green color in the tissues.

In vivo release of Exendin-4 in mice (C57BL6). Following the procedures described above, heparin-TCA wrapped Exendin 4-pDNA was orally administered to mice at different dosages (2.5, 5 and 10 mg/kg) after 12 hr of fasting. For preparing the formulations, Exendin-4 was added to bPEI in a ratio of 5/1 and incubated for 30 min, allowing them to form a complex. The complex then was wrapped with heparin-TCA in a ratio of 1/0.2. The formulation was characterized by zeta and DLS to measure the zeta potential value and hydrodynamic size distribution, respectively. After 30 min of incubation at room temperature, the formulation was lyophilized over two days. The calculated amount of the powder was dissolved in 10 mM HEPES buffer (200 uL) and incubated at room temperature for 30 min to make a uniform dispersion. The IV administered mice were not fasted before injection. Blood was collected from the tail vein 12, 24 and 36 hr after the oral and IV administration. The expression/release of Exendin-4 in blood was analyzed/ measured by an Exendin-4 assay kit (Exendin-4 (Heloderma suspectum)-EIA Kit, Phoenix pharmaceuticals, INC. CA, USA).

Figure 14:
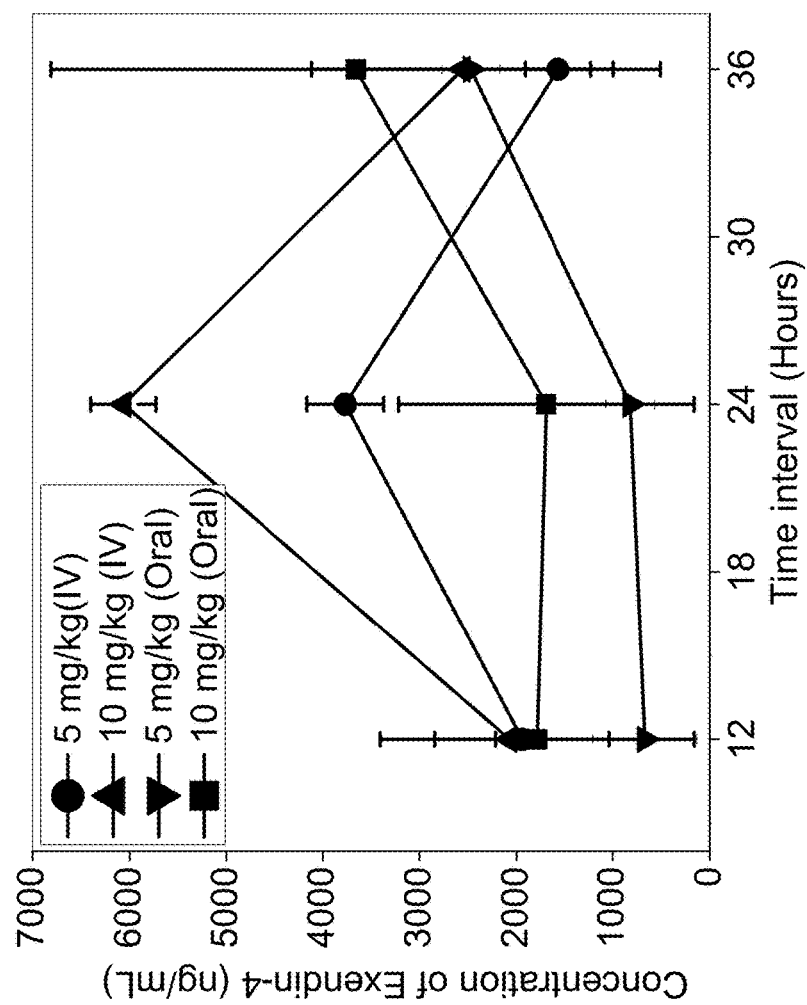
FIG. 14 is a graph which shows the plasma concentration of Exendin-4 over time, after IV and oral administration of an exemplary composition to a mouse.

Exendin-4 release in mice (C57BL6). FIG. 14 is a graph which shows the plasma concentration of Exendin-4 over time, after IV and oral administration of a heparin-TCA wrapped Exendin-4-pDNA composition to a mouse, at two dosages (5 and 10 mg/kg of Exendin-4-plasmid DNA). The data represents mean±SD, n=5.

FIG. 14 shows that the release of Exendin 4 is directly proportional to the administered dosage with both oral and IV administration of the compositions. The expression and release of Exendin 4 after IV administration is initially higher than that after oral administration for the same dose amount. At 36 hr post administration, however, the IV group showed the plasma concentration descending whereas the plasma levels were ascending for the oral group. The graph indicates that a longer observation time is needed to get the Tmax and Cmax values for the oral administration group. However, the highest concentration for 10 mg/kg of IV was observed at 24 hr (Tmax=about 24 hr and Cmax=about 6500 ng/mL).

Glucose level monitoring in type II diabetes model after administration of pGLP-1 formulations. Female Zucker Diabetic Fatty (ZDF) rats which were 6 weeks old were kept in a metal cage with free access to food and water. The ZDF rats develop obesity and insulin resistance at a young age and progressively develop hyperglycemia with aging. Hyperglycemia in ZDF rats is associated with impaired pancreatic β-cell function, loss of pancreatic β-cell mass and decreased responsiveness of liver and extrahepatic tissues to the actions of insulin and glucose. Blood glucose levels in the ZDF rats were >300 mg/dL as measured by a portable blood glucose monitoring device (Accu-chek, Roche Diagnostics, Basel, Switzerland). The rats were divided in 2 groups; one group was given a pGLP-1 gene formulation containing only the gene, i.e. free pGLP-1 (3 rats), and the other group was given a heparin-TCA wrapped pGLP-1 composition formulation (5 rats). To prepare the formulations, the GLP-1 gene was mixed with bPEI (with a N/P ratio of 5/1) and incubated for 30 min to allow the complex to form via electrostatic interactions. The complex was wrapped with anionic heparin-TCA by dissolving the compounds in HEPES buffer and incubating them at room temperature for 30 min. The formulation was then lyophilized by freeze drying over 2 days and re-dispersed in HEPES buffer solution for oral and IV delivery.

The rats of both the free pGLP-1 gene formulation group and the heparin-TCA wrapped pGLP-1 composition formulation group were fasted overnight (12 hours) before oral gavage delivery of 100 μg of the free pGLP-1 gene or in an amount providing 100 μg of the pGLP-1 gene in the heparin-TCA wrapped pGLP-1 composition formulation, respectively. The calculated amount of the dried formulation (equivalent to 100 μg of the GLP-1 gene) was dissolved in 100 μL HEPES buffer and incubated for 30 min in cell incubator (37° C.) prior to oral/IV administration.

In a different study, BALB/c mice were treated with streptokinase to damage the β-cells of their pancreas to inflammation in the pancreas. The mice were housed in a metal cage with free access to food and water and continuously monitored. Their blood glucose level increased to about 300 μg/dL over 2 weeks after streptokinase treatment. The mice were divided into two groups; oral (7 mice) and IV (7 mice) and the heparin-TCA wrapped pGLP-1 formulation (in an amount providing 100 μg of the pGLP-1 gene) was administered orally and intravenously.

The body weight of the animals was monitored regularly. The calculated amount of dried formulation (equivalent to 100 μg of GLP-1 gene) was dissolved in 100 μL HEPES buffer and incubated for 30 min in cell incubator (37° C.) prior to oral/IV administration.

Histochemistry. After 21 days of observation, specific organs (the duodenum, jejunum, ileum, kidney and liver) of the rats were isolated to observe GLP-1 expression through immunohistochemistry staining. The rats were dissected and selected organs were isolated after observing their blood glucose levels. The tissues were fixed in 10% formalin and embedded in paraffin to allow for slicing the tissue into 15 μm thick sections. The sections were subjected to an indirect immunohistochemical method for immune staining. The mouse monoclonal (8G9) primary antibodies were used for analysis of GLP-1 (Abacam ab26278) and the process was conducted according the instructions of the histochemistry assay kit provided by the vendor.

Figure 15A:
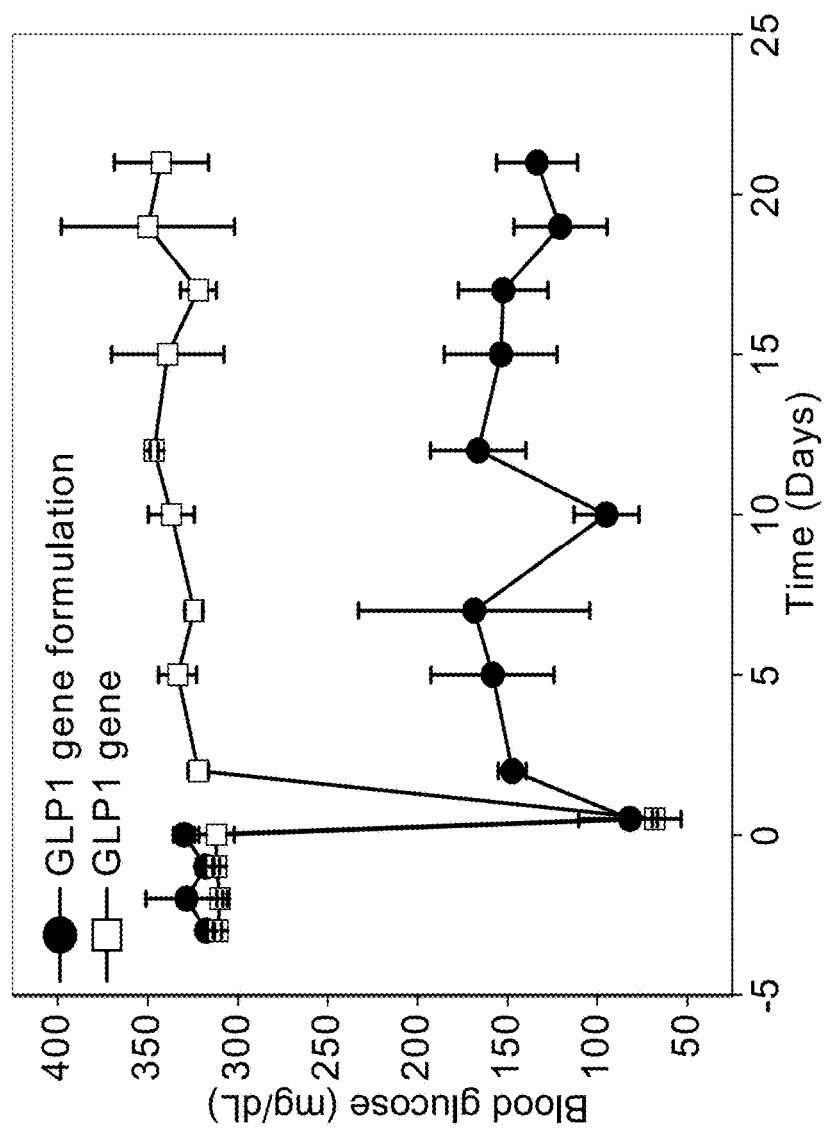
FIGS. 15A-15C show graphs of the blood glucose levels of animals treated with an exemplary composition.
Figure 15B:
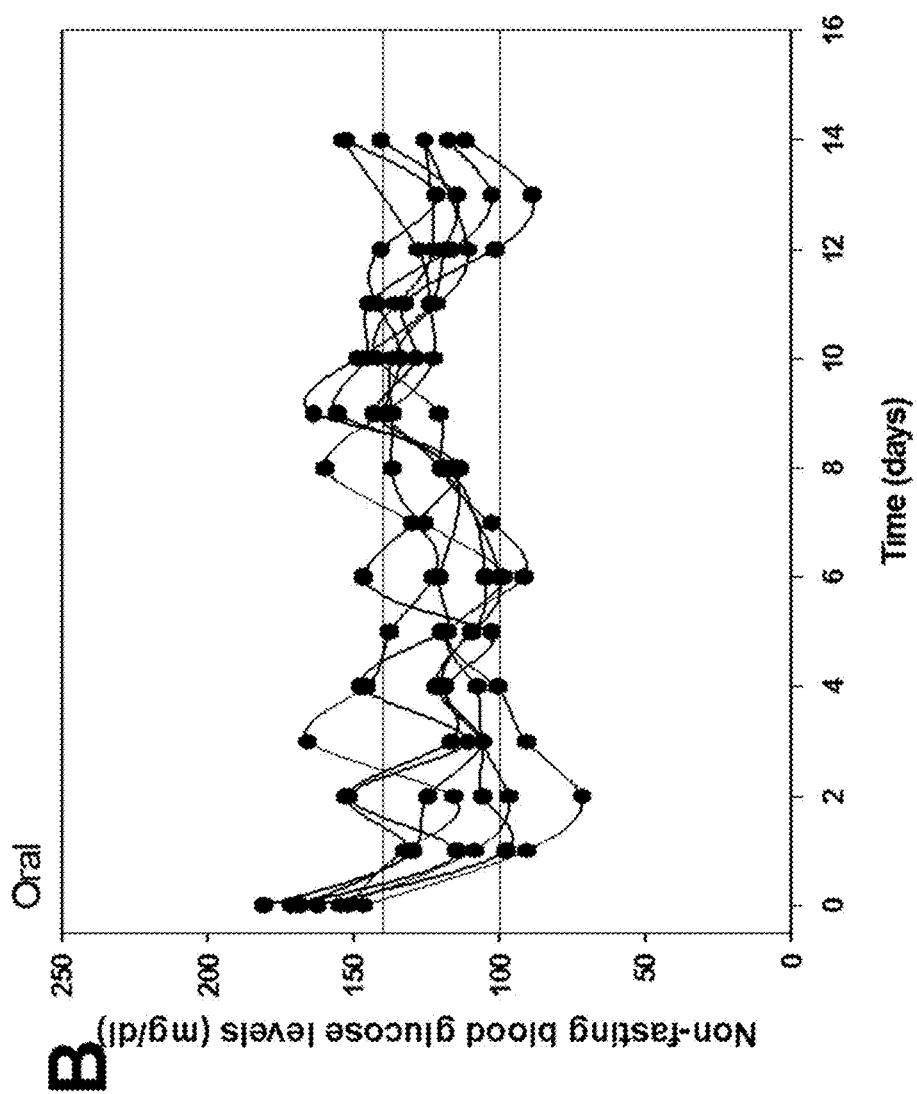
Figure 15C:
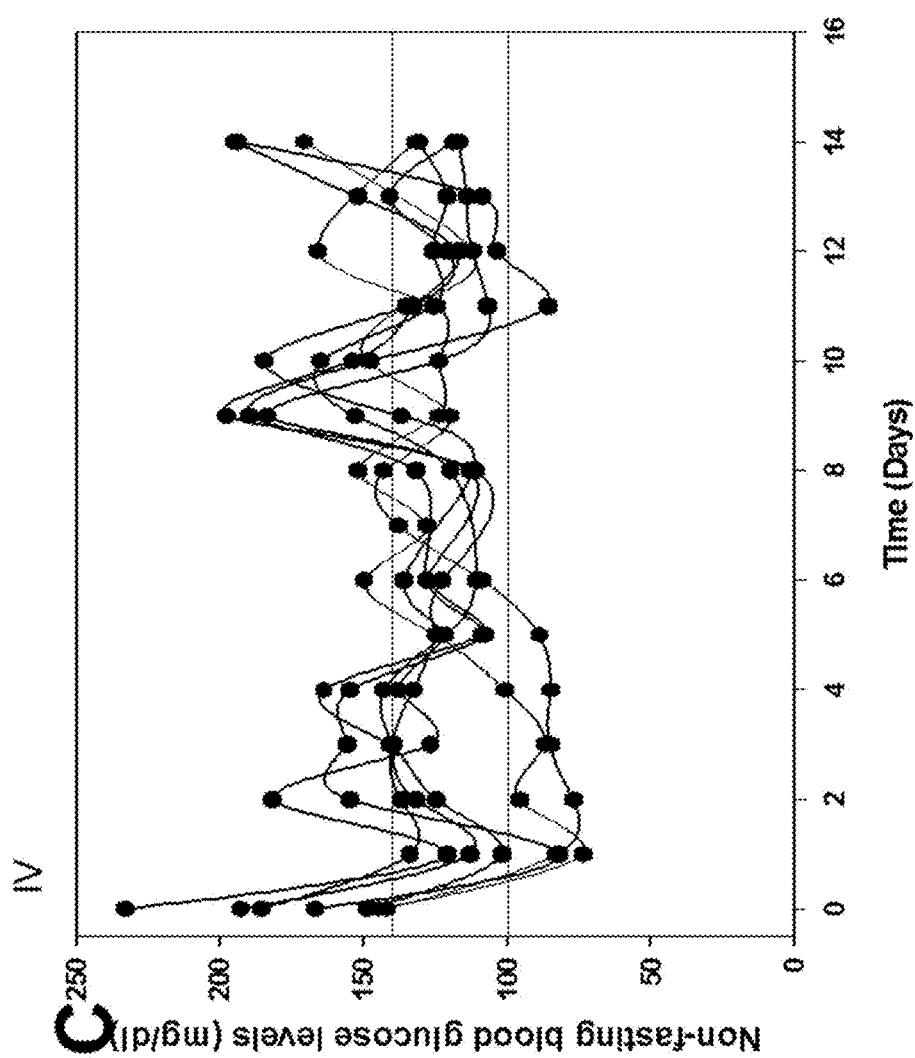
Figure 15D:
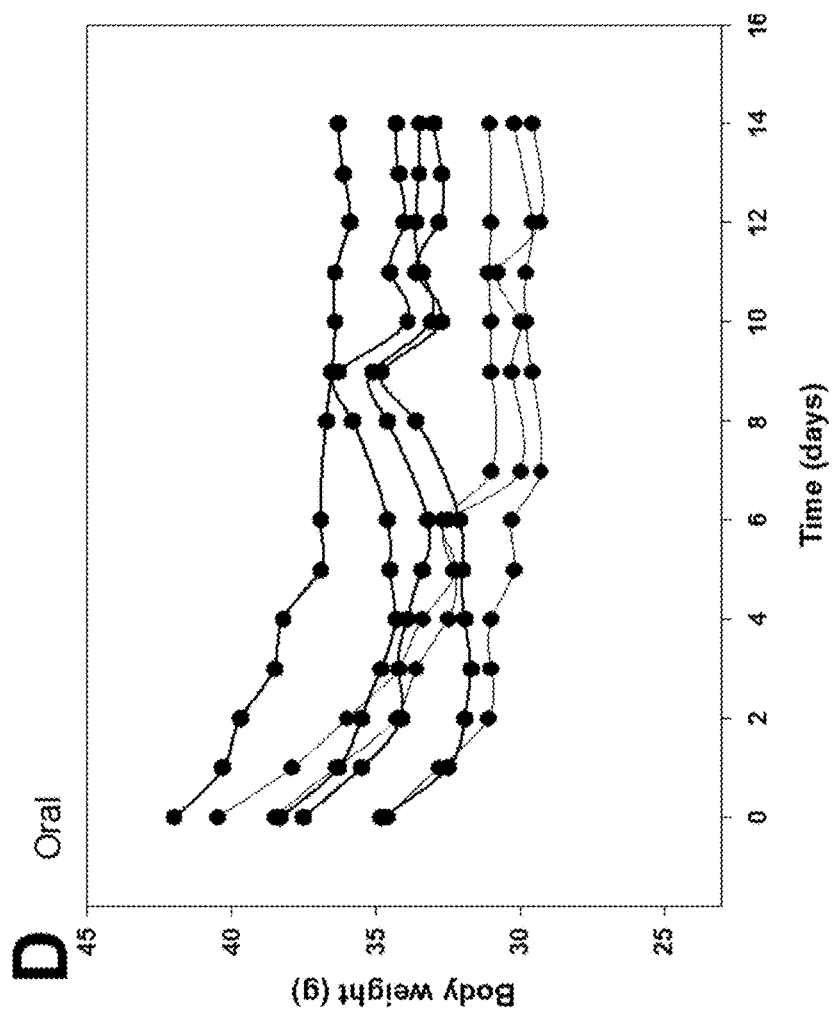
FIGS. 15D-15E show graphs of the body weights of animals treated with an exemplary composition.
Figure 15E:
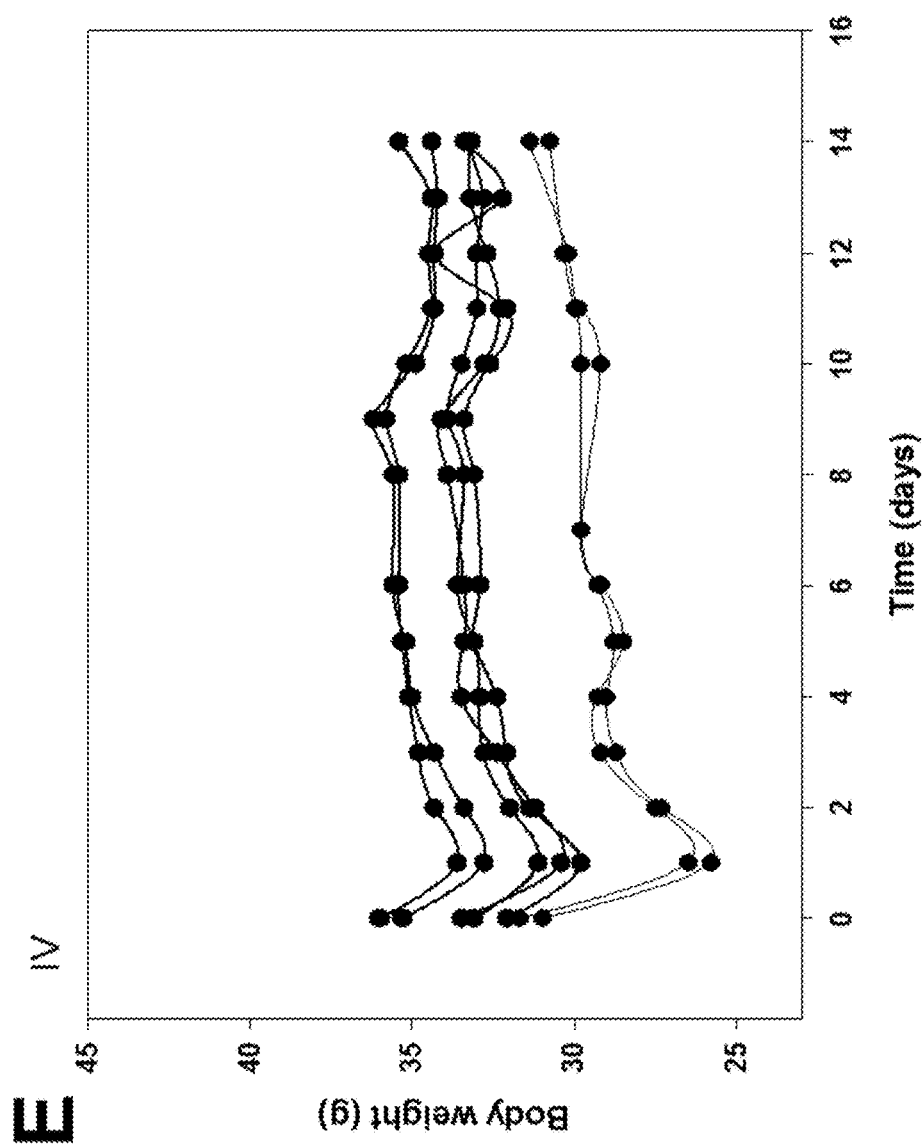
Figure 15F:
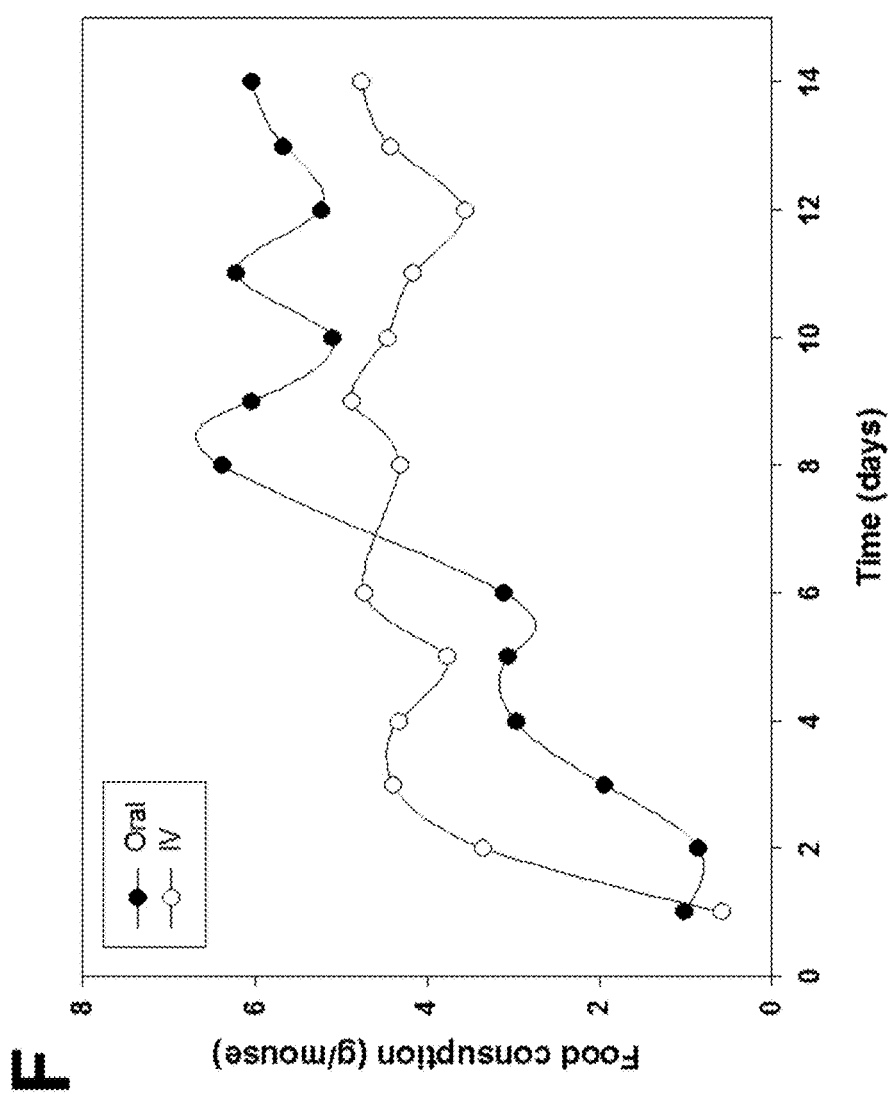
FIG. 15F shows a graph of food consumption over time of animals treated with an exemplary composition.
Figure 15G:
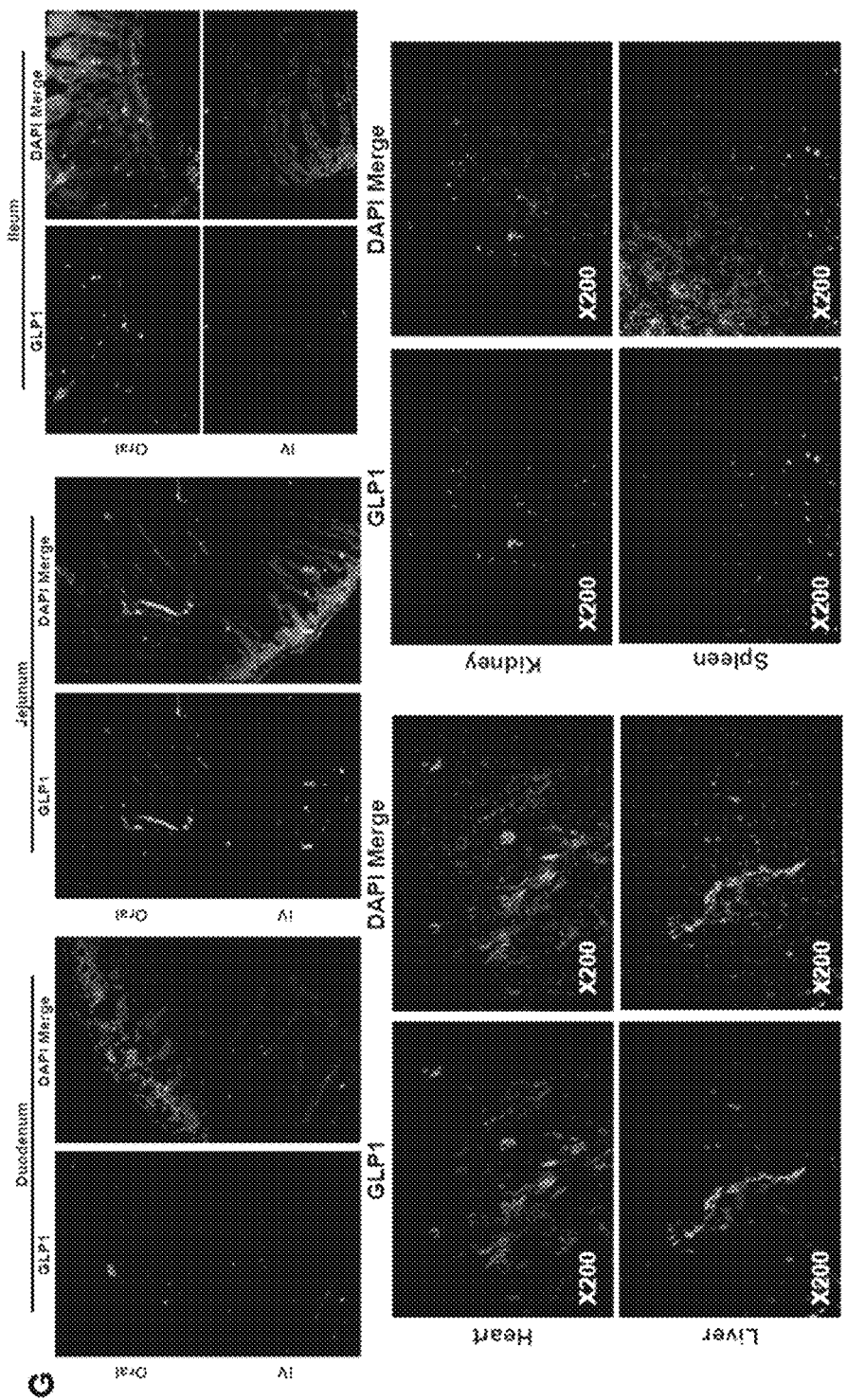
FIG. 15G is a series of images showing the amount of GLP-1 present in various animal organs after administration of an exemplary composition.

The GLP-1 expression was directly observed by confocal microscopy (green in FIG. 15G) whereas the nuclei of the cells were stained with DAPI (blue in FIG. 15G). The tissues were isolated and a tiny portion were embedded into a paraffin shaped by stainless steel cascade. The tissues were sectioned as 15 μm thick slices, and embedded onto a glass slide and stained with both DAPI and Abacam ab26278 for visually observing the nucleus and expression of GLP-1 in the cells, respectively.

The lyophilized heparin-TCA wrapped pGLP-1 formulation (in an amount equivalent to 100 μg GLP-1 gene) was dissolved in 100 uL HEPES buffer and orally administered to the overnight-fasted type-II diabetes model ZDF rats. The free GLP-1 gene formulation was also delivered to another group of animals as a control study. The monitored blood glucose levels were low, at about 60 mg/dL, during the period of fasting. Food was given to the animal 6 hr after oral administration of the formulation to avoid any interactions between the formulations with food that may inhibit absorption in the GI tract.

FIGS. 15A-15C are graphs of the blood glucose levels of animals treated with the heparin-TCA wrapped pGLP-1 formulation. As seen in FIG. 15A, the ZDF rats treated with the free GLP-1 gene formulation (open squares) maintained a blood glucose level around 300-350 mg/dL over the 21 days studied, with a short-term lower level on the day of oral administration. In contrast, the ZDF rats treated with the heparin-TCA wrapped pGLP-1 composition formulation (black circles) had a blood glucose level around 100-150 mg/dL after oral administration, which was maintained for the 21 days studied.

FIG. 15B shows the non-fasting blood glucose levels of each of the BALB/c mice in the oral administration group over the two weeks after administration of the heparin-TCA wrapped pGLP-1 composition formulation. In general, the levels ranged between about 100 and about 150 mg/dL. FIG. 15C shows the non-fasting blood glucose levels of each of the BALB/c mice in the IV administration group over the two weeks after administration of the heparin-TCA wrapped pGLP-1 composition formulation. In general, the levels ranged between about 100 and about 150 mg/dL.

FIGS. 15D-15E show graphs of the body weights of each of the BALB/c mice treated with the heparin-TCA wrapped pGLP-1 composition formulation. FIG. 15D shows the data for the orally administered group, and FIG. 15E shows the data for the IV administered group.

FIG. 15F shows a graph of the amount of food consumed over the two weeks after administration of the heparin-TCA wrapped pGLP-1 composition formulation for the oral group (solid circles) and the IV group (open circles). The oral group generally consumed more food per mouse than the IV group after about one week, and the food consumption for the IV group stayed relatively constant after about day 3 at about 4 g/mouse, but the food consumption for the oral group didn't stabilize until after about day 7 at about 6 g/mouse.

FIG. 15G is a series of images showing the amount of GLP-1 present in various rat organs after administration of the heparin-TCA wrapped pGLP-1 composition. The images show that GLP-1 expression was highest in the kidney, but GLP-1 expression was also observed in the duodenum, jejunum, ileum and liver as shown in the confocal images of tissues stained with DAPI.

The data shows (FIG. 15A) that once the rats had access to food 6 hr after oral administration of the formulations, their blood glucose levels started to increase. For the animals treated with the free GLP-1 formulation, the level returned to about 300-350 mg/dL from about 60 mg/dL, within a day after administration. However, the blood glucose levels of the heparin-TCA wrapped pGLP-1 formulation administered rats was maintained at about 100-150 mg/dL for up to 21 days after a single oral dose of 100 μg of the heparin-TCA wrapped pGLP-1 formulation.

The results provide evidence of a significant blood glucose lowering effect in rats treated with the heparin-TCA wrapped GLP-1 formulation, an effect which is sustained for a long period after a single oral dose administration. In a type-I model of diabetes, mice were administered orally and intravenously with the heparin-TCA wrapped GLP-1 gene formulation at the same dose amount of the gene. During the 14 days of blood glucose monitoring, oral delivery and IV delivery showed a similar profile for blood glucose levels as investigated in mice whose pancreatic cells were damaged by streptokinase. The overall results from blood glucose monitoring indicate that the formulations of the heparin-TCA wrapped pGLP-1 composition were orally absorbed adequately enough to reduce blood glucose levels and maintain them within the normal glucose range. Surprisingly, only a single oral dose kept blood glucose levels in the normal range for two weeks.

Conclusion. In the in vitro cytotoxicity and cellular transfection studies, HepG2 (hepatocyte) and EaHy926 (epithelial) cell lines were monitored at different time intervals, and the data demonstrates that the eGFP locates around the cytoplasm as well as the nucleus of cells. Oral absorption and pharmacokinetics studies conducted with a heparin-TCA wrapped eGFP composition in mice showed evidence of expression in the liver which was observed both visually and quantitatively. While complexes of the gene and a cationic moiety (but no bile acid coating) non-specifically transfected enterocytes in the stomach, duodenum, jejunum and other internal organs, the bile acid coated complexes transfected the distal small intestine and ileum, which actively uptakes bile acids, and significant eGFP expression was observed in the liver, lung, and kidney.

The plasma Exendin-4 levels in mice treated with a heparin-TCA wrapped Exendin-4 composition were approximately 10,000 fold higher than therapeutic Exendin-4 levels, which are on the order of a few hundred ng/mL, after 5-10 mg gene/kg doses. Therapeutic efficacy was also observed with a heparin-TCA wrapped GLP-1 composition in both a type-I and a type-II diabetes model for 2 and 3 weeks, respectively, which both show a reduction in the blood glucose levels to within a normal range.

In summary, the experimental results with three different genes support the concept of enhancing their oral absorption. Notably, two of the genes studied are potential therapeutic agents (Exendin-4 and GLP-1) for treating diabetes and have been validated in both a mouse model and a rat model of the human disease. The quantitative and qualitative data presented here, both in vitro and in vivo, regarding the oral absorption mechanism, organ expression and therapeutic efficacy of the genes, support the concept that bile acid linked anionic polymers can enhance the stability of the gene complex and simulate oral absorption through bile acid and Ost alpha-Ost beta transporters in the small intestine. The high accumulation and expression levels of the genes in the liver also indicate that the compositions actively bind with these receptors, which are overexpressed in liver cells.

Example 2. Protein Delivery

A cationic particle can be formed with a therapeutic protein which itself is cationic, or the protein can be complexed with a cationic polymer such as protamine. An exemplary therapeutic protein is insulin. The cationic complex can then be coated with a moiety made from a bile acid or bile acid conjugate which is covalently bound to an anionic polymer. An example of such a moiety is heparin-TCA. The resultant therapeutic composition would be expected to have a size of about 10 nm to about 10 um. The resulting composition would be anionic and could be orally administrated to an animal or a human subject, to reduce blood glucose levels.

Example 3. Bile Acid and Bile Acid Conjugates for Small Molecule Delivery

The oral administration of many drugs, including doxorubicin (DOX), is challenging due to their poor intestinal permeability which results in a low oral bioavailability. Oral formulations of drugs take into account the solubility, stability, dissolution rate, and permeability in the gastrointestinal (GI) tract of the drug, all of which affects its oral bioavailability. The oral dosage forms of these drugs should have a rapid dissolution rate and a high absorption rate, in order to lower the half-life and metabolism in the GI tract and maximize oral bioavailability. To improve drug efficacy, particularly of an anticancer drug, the oral formulation should overcome barriers in its absorbance through the epithelial lining of the walls of the GI tract.

DOX is an anticancer drug that has been widely used for treating lymphomas, sarcomas, breast, ovarian, and lung cancers. DOX damages DNA by intercalating into the bases of DNA, which inhibits topoisomerase II enzyme activity and interferes in DNA transcription. DOX is a drug with a BCS classification of III, which has a favorable solubility but poor permeability, and a low oral bioavailability (about 5%). However, a significant clinical limitation to using DOX is due to its cardiotoxicity resulting from oxidative stress generation, and other side effects including nephrotoxicity, myelosuppression, and the development of multidrug resistance—all of which leads to a narrow therapeutic index. Thus, a new formulation strategy is required to improve its poor intestinal permeability and oral bioavailability.

Bile acid transporters are a potential target for drug delivery, as bile acids secreted from the liver are reabsorbed from the terminal ileum through intestinal epithelial cells and are transported back to the liver via the portal vein. High bile acid recycling ratios make the enterohepatic circulation of bile acids a highly efficient process and benefit the bile acid transporters that are mainly expressed in the liver and the terminal ileum. Taurocholic acid (TCA) is an abundant bile acid, and is present in human intestinal fluids in approximately 45%.

TCA can be used as a drug carrier by covalent attachment to an anionic polymer, then delivered via oral administration. The TCA present on the surface of the polymer can interact with the bile acid transporters in the small intestine and improve the drug's intestinal permeability as well as its bioavailability. In the case of DOX, its hydrophilic cationic properties allow it to cross the intestinal epithelium cells mainly via the paracellular pathway. However, a TCA coating on the DOX surface would maximize the intestinal transcellular absorption via the $Na^+$-dependent apical sodium bile acid transporter (ASBT), which is present mainly in the terminal ileum, to facilitate DOX transport from the terminal ileum to the portal vein and introduce DOX into the systemic circulation.

Here, heparin (H) and chondroitin sulfate (CS) were chosen as exemplary anionic polymer backbones to covalently bind with TCA, due to their high biocompatibility, water solubility, and biodegradability. These polysaccharides are natural polymers, which provide a high amount of biocompatibility. H-TCA and CS-TCA can coat the surface of the DOX, increase its stability in the gastrointestinal (GI) tract, and protect the DOX from the GI environment. In addition, H-TCA and CS-TCA can complex with DOX and form small particles, which can be absorbed more efficiently than micron size particles. The particles disclosed herein range from about 10 nm to about 10 um. This formulation strategy can reduce the amount of non-specific adsorption and improve the specific intestinal absorption, improving the bioavailability of DOX. In addition, efficient TCA recycling via enterohepatic circulation could be beneficial to anticancer chemotherapy targeting liver carcinomas.

Materials. Doxorubicin hydrochloride, sheared salmon sperm DNA (Trevigen, MD), dimethyl sulfoxide (DMSO), 4-(2-hydroxy-ethyl)-1-piperazine (HEPES), 3-(4, 5-dimethylthiazol-2-yl)-2,5-diphenyltetrazolium bromide (MTT), D-glucose, sodium bicarbonate, recombinant human insulin, Hoechst 33342, RPMI 1640 medium, Dulbecco's phosphate buffered saline (DPBS), Dulbecco's modified eagle's medium (DMEM), carbodiimide (EDC), N-hydroxysuccinimide (NHS) were purchased from commercial vendors and used as received unless otherwise noted.

Preparation and characterization of DOX-loaded particles. To evaluate the potential for increasing the permeability of poorly bioavailable drugs such as DOX, a bile acid or bile acid conjugate (here, taurocholic acid, or TCA) is attached to an anionic polymer (here, the polysaccharides heparin and chondroitin sulfate are studied) to provide a composition suitable for oral delivery.

Heparin-bound taurocholic acid (H-TCA) was prepared by dissolving 1 mol of TCA sodium salt in DMF at 0° C., followed by the addition of 6 mol of triethylamine and 5 mol of 4-nitrophenyl chloroformate (NPC). The solution was then extracted three times with ethanol and DI water. A rotary evaporator was used to remove the organic solvent and the samples were freeze-dried to obtain TCA-NPC. One mol of TCA-NPC was dissolved in DMF with 2 mol of 4-methylmorpholine, and 100 mol of ethylene diamine was added dropwise and the product was dried to obtain TCA-$NH_2$.

To attach the TCA to heparin (H) or chondroitin sulfate (CS), 1 mol of the polysaccharide was dissolved in DI water, and EDC (5 mol) and NHS (5 mol) was added to the solution and stirred for 12 hr at RT. The same molar ratio of TCA-$NH_2$ was added to each of heparin and chondroitin sulfate to obtain the same coupling amount of TCA, which was 1:4 (one mol of polysaccharide to 4 mol of TCA). After a day, the solution was placed in a MWCO 1000 dialysis membrane and dialyzed against water. The final product was lyophilized and confirmed by its $^1$H-NMR spectrum in $D_2O$.

Figure 16A:
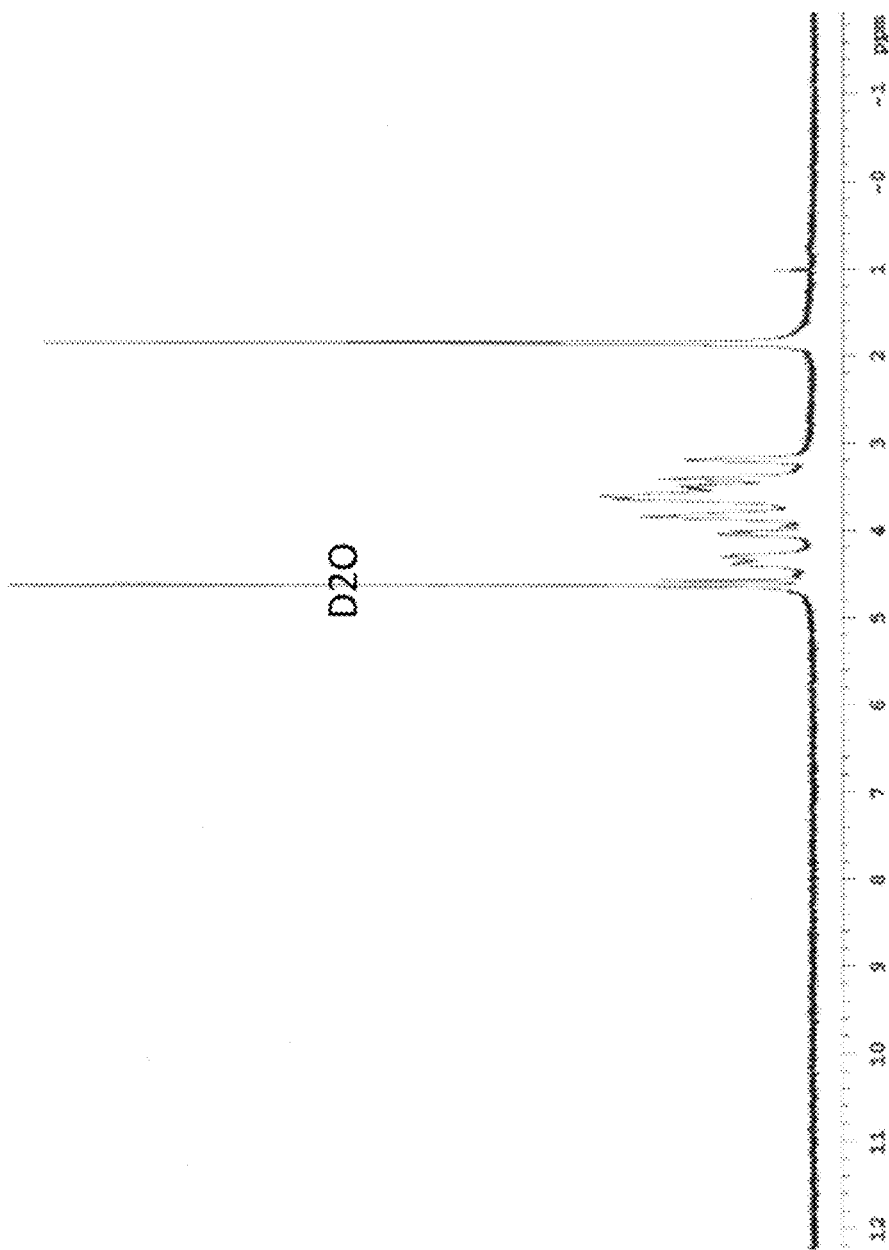
FIGS. 16A-16B are proton NMR spectra of (16A) chondroitin sulfate and (16B) chondroitin sulfate covalently bound to taurocholic acid.
Figure 16B:
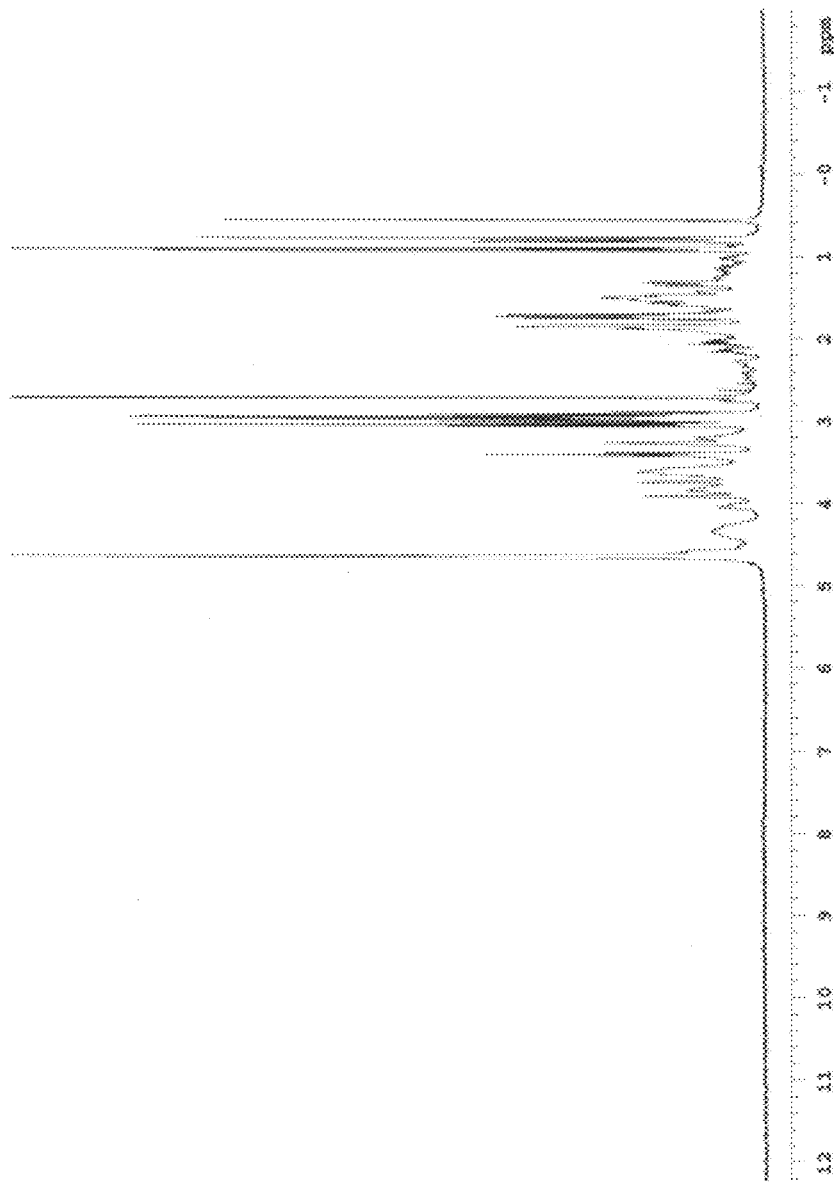

FIG. 16A shows the proton NMR spectrum of chondroitin sulfate prior to reaction with the TCA-$NH_2$. FIG. 16B shows the proton spectrum of the product from the chondroitin sulfate coupling with TCA-$NH_2$ after dialysis, confirming the covalent bonding.

Formation and reconstitution of DOX-loaded particles. DOX-loaded particles were formed via electrostatic coupling of the cationic DOX with the anionic TCA complexes CS-TCA and H-TCA. DOX was coated with either CS-TCA or H-TCA via an electrostatic interaction for oral administration.

CS-TCA was directly mixed with DOX at a 1:2 ratio (w/w). The solutions were mixed using a vortex and sonicated for 10 seconds at 20 amplitude followed by incubation for 30 min at RT.

For the H-TCA complex, DOX was first mixed with sheared salmon sperm DNA to get a negative surface charge on the DNA/DOX complex. The DOX/DNA complex was then mixed with ε-poly-L-lysine (ε-PLL) to get a complex which had a positively charged surface. Thus, sheared DNA was used to associate with the DOX to form an anionic DNA/drug ("DD") complex, then ε-PLL was used to coat the DNA/drug complex to provide a DNA/drug/polymer complex ("DDP") with a cationic surface. Finally, H-TCA was used to coat the cationic DDP complex, to provide the final therapeutic compositions.

In certain embodiments, the small-molecule therapeutic agent may itself be cationic, and therefore it may not be necessary to add other components (such as DNA and/or poly-lysine) to form the core complex. Thus, in some embodiments, the core complex comprises a cationic small-molecule therapeutic agent.

For each preparation, the solutions were mixed using a vortex and sonicated for 10 seconds at 20 amplitude followed by incubation for 30 min at RT. The final formulations of DDP coated with H-TCA were prepared with a ratio of DDP to H-TCA of 2.8:2.4. For the DDP/H-TCA composition, the ratio of DOX:DNA was 1:1, the ratio of the (DOX/DNA) moiety:ε-PLL was 2:0.8, and the ratio of the DDP:H-TCA was 2.8:2.4, with all ratios calculated based on weight (w/w).

Two DOX formulations were prepared, with different ratios of drug to bile acid-polymer; DOX/CS-TCA at a 1:2 w/w ratio and DDP/H-TCA at a w/w ratio of 2.8:2.4.

The final compositions formed particles which were evaluated further. Specifically, the particle sizes and surface charges of the DOX particles were evaluated by dilution with HEPES buffer (20 mM, pH 7.4), then the hydrodynamic particle size and zeta potential of the particles were monitored by dynamic light scattering (DLS) using a Zetasizer 3000 (Malvern Instruments, UK) at a wavelength of 677 nm and a constant angle of 90° at room temperature (25° C.).

After freeze-drying the samples, the particles were reconstituted in DI water and the samples were sonicated for about 10 sec at 20 amplitude immediately prior to the DLS measurements. The lyophilized powders were stored at −20° C. until use.

Figure 17:
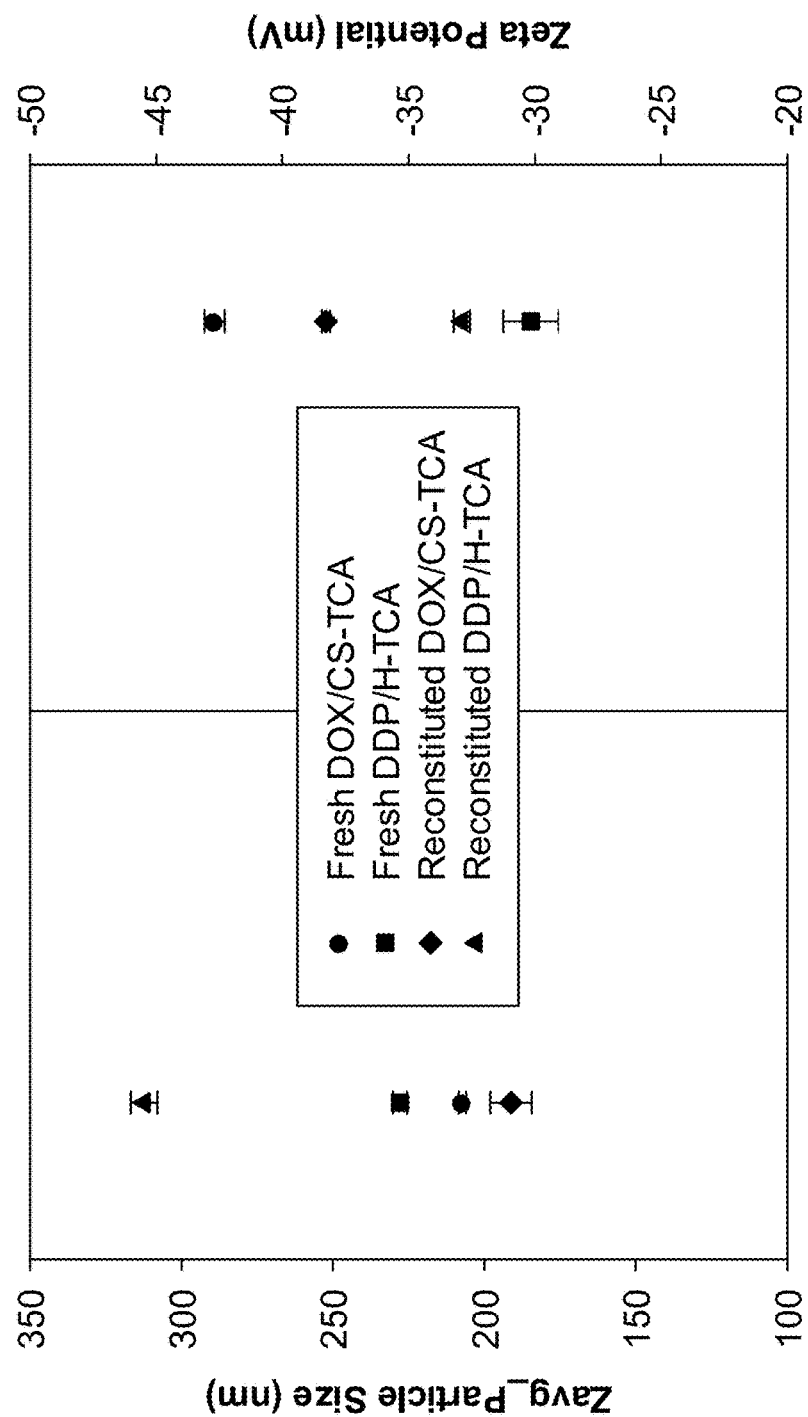
FIG. 17 is a graph of the particle size and zeta potential of exemplary formulations.

Analysis of the electrostatic interactions between the cationic DOX and the anionic TCA complexes indicate that DOX-TCA particles were formed. FIG. 17 is a graph of the particle size and zeta potential of samples of the freshly prepared and reconstituted DOX-TCA particles. The data is presented as the mean±SD, n=10.

Before the room temperature incubation, the particles were sonicated for about 10 sec at 20 amplitude and a reduction of particle size with a narrow polydispersity index (PDI) was observed. Sonication induces acoustic cavitation which creates shock waves with high force in the solution. As a consequence, particles collide into each other and agglomerates are broken up, which results in an overall decrease in particle size and PDI.

As shown in FIG. 17, the hydrodynamic diameters of the fresh DOX/CS-TCA and DDP/H-TCA particles were about 200 nm and about 230 nm, respectively. In the case of DDP/H-TCA, the multiple layers of components in the bile acid-wrapped complex increased the size. The zeta potential of fresh DOX/CS-TCA particles was −42.7 mV and −30.2 mV for the fresh DDP/H-TCA particles. They were both negatively charged due to the presence of carboxylic groups in the polysaccharide backbones.

The diameters of the DOX-loaded particles were slightly increased after reconstitution compared to that of samples before freeze-drying. The DOX-loaded particles after reconstitution displayed particle sizes around 201 nm for DOX/CS-TCA and around 312 nm for DDP/H-TCA; however, there was no significant change in their zeta potentials.

It was found that the H-TCA coating of the DDP complex produced a relatively large particle size with a wide polydispersity index (PDI). In contrast, a single coating of CS-TCA produced a smaller particle size with a narrow PDI at the 1:2 (w/w) ratio prepared. The DOX/CS-TCA and DDP/H-TCA particles were able to be reconstituted in deionized water after freeze-drying, and generally retained their size and zeta potential.

Spectral measurement of DOX encapsulation. Ultraviolet-visible (UV-Vis) spectroscopy (SpectraMax, USA) was used to monitor the change in absorbance of DOX-loaded particles as compared to free DOX. Samples of DOX (0.1 mL samples, with 25 µg of DOX per sample) were prepared and diluted in 0.9 mL DI water to provide a total volume of 1.0 mL, and were loaded in a quartz cuvette. The UV-vis absorbance spectra of free DOX displayed peaks at 232 and 490 nm, and the spectra of DOX-loaded bile acid particles were compared with the spectra of the free DOX control sample.

Figure 18A:
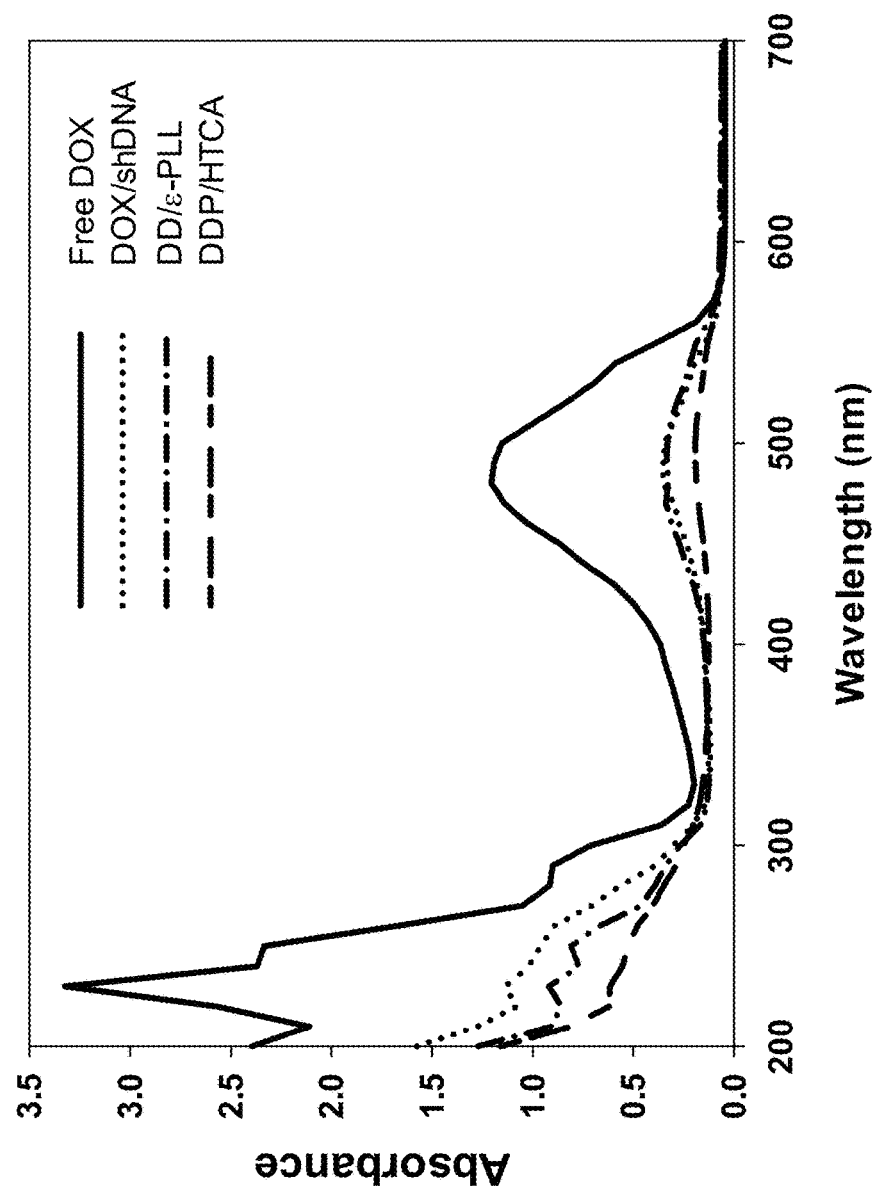
FIGS. 18A-18B are UV-VIS spectra of various exemplary formulations.
Figure 18B:
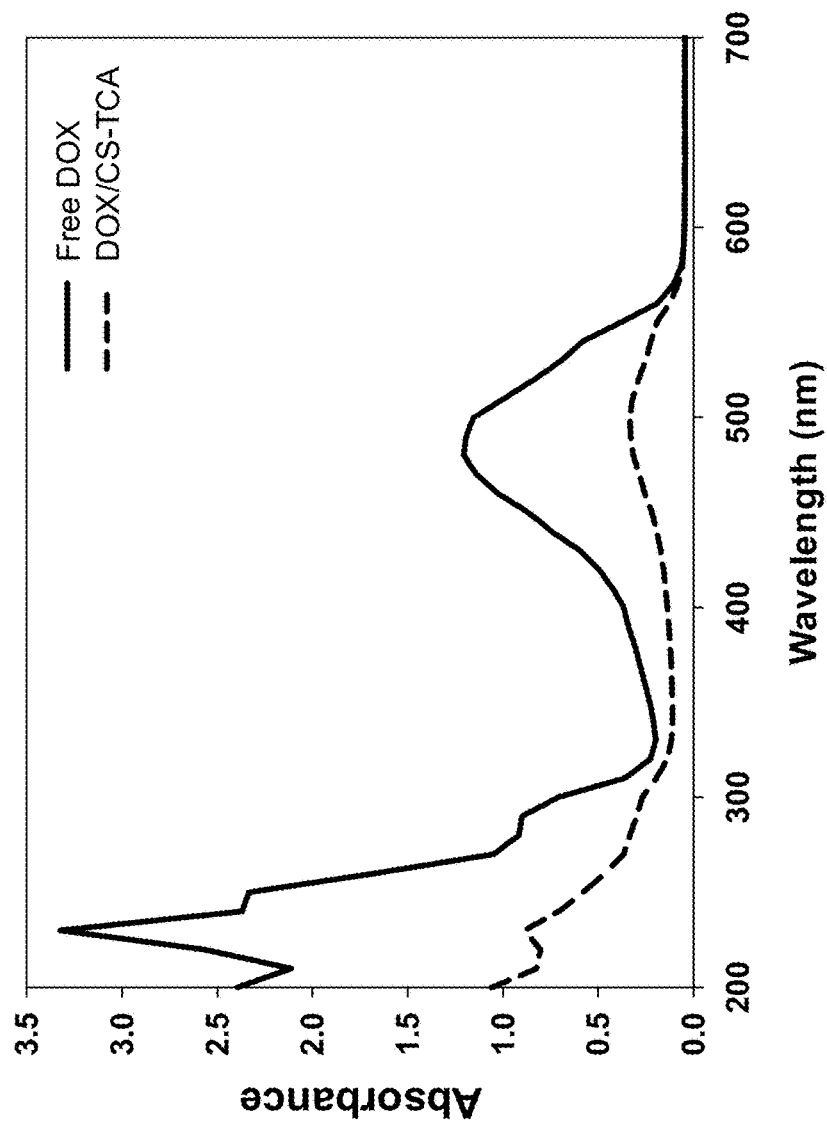

FIGS. 18A and 18B show the UV-Vis spectra of these samples. FIG. 18A shows the spectra of free DOX (solid trace), DOX/DNA (dotted trace), DOX/DNA/ε-PLL (dot-dashed trace) and the DDP/HTCA composition (dashed trace). FIG. 18B shows the spectra of free DOX (solid trace) and the DOX/CS-TCA composition (dashed trace).

As seen in FIG. 18A, DOX without any carrier displayed two main peaks at 232 nm and 490 nm. When DOX was coupled with the TCA linked polysaccharides heparin and chondroitin sulfate, there was a significant diminishing of these two peaks in the UV-Vis spectra. Both the DDP/H-TCA and DOX/CS-TCA samples showed the complete absence of the two DOX peaks after the single coating of the CS-TCA particle, or the multiple coating of the H-TCA particle, which indicates the interaction between DOX and the TCA linked polysaccharides. The change in the spectra also indicates that the loading of DOX in both formulations was successful. Within the particles, the DOX can be encapsulated with a high loading efficiency.

Figure 19A:
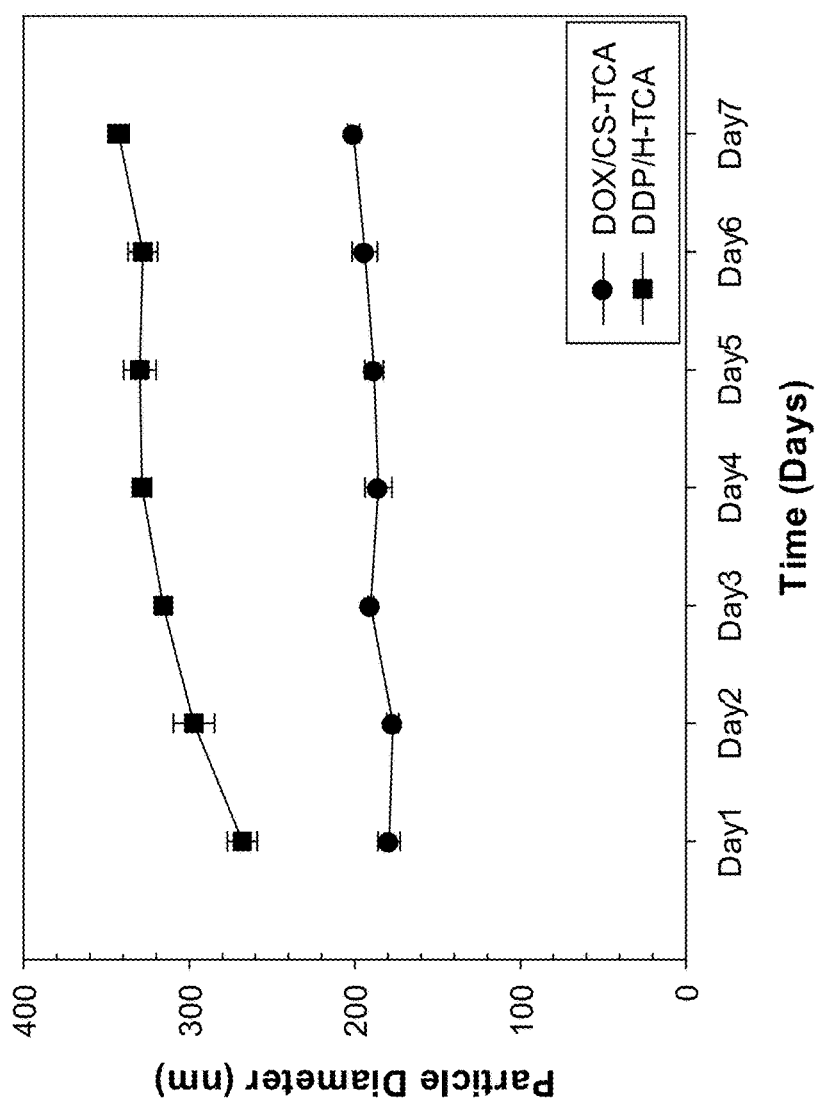
FIGS. 19A-19B are graphs of the particle diameter over time (FIG. 19A) and at varying pH values (FIG. 19B) of exemplary formulations.

The potential for long-term storage for these DOX-containing formulations was evaluated, to determine whether they can retain their properties after such storage. The particle size of the DOX/CS-TCA and DDP/H-TCA compositions was measured over a period of 7 days, as shown in FIG. 19A.

As shown, after 7 days of storage, the DOX/CS-TCA formulation remained generally stable with only a slight change of size, maintaining a particle diameter of about 190 nm. In the case of the DDP/H-TCA, the particle size slightly increased over time, from about 270 nm to about 340 nm. This gradual increase in the particle size suggested that multiple coatings may be unstable compared to a single coating, thus the single coating of the CS-TCA particle may provide better stability with regards to particle size than the multi-layered DDP/H-TCA particle.

Figure 19B:
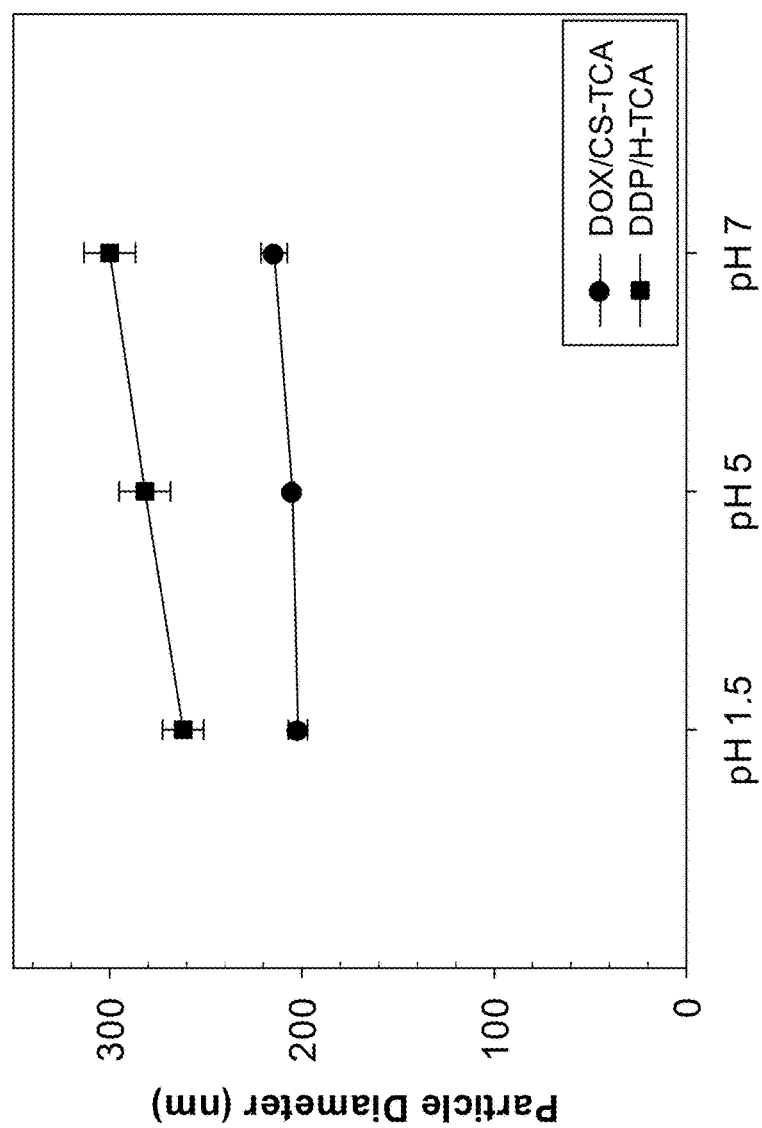

In vitro stability studies. The stability of DOX-loaded particles was tested at three different pH values (pH 1.5, 5, and 7) in a 0.1M Tris HCl buffer. The mean diameter of the particles was monitored by dynamic light scattering each day up for seven days, as shown in FIG. 19B, with a mean±SD, n=3.

At the acidic pH of 1.5, there was a decrease in the particle sizes for both polysaccharide compositions as compared to the size of the particles at the higher pH values, and the decrease was larger for the DDP/H-TCA particle than for the DOX-CS-TCA particle. DOX has a pKa of between about 7.2-8.0, so it is partially ionized at pH 7.4 by protonation of the amino group. Thus, DOX is more protonated at lower pH, and as a consequence, a stronger electrostatic interaction can be established between DOX and the anionic CS-TCA and the short piece of DNA, which may contribute to the decrease in particle size. The smaller particle size at the low pH also suggests that the DOX-loaded particles are stable at the pH values in the stomach, which can protect DOX from degradation. The small difference in size for the DOX/CS-TCA particles at different pH values, which went from about 200 nm at pH 1.5 to about 220 nm at pH 7, indicated that the particles with a single coating were generally more stable and maintained similar sizes over the wide range of pH values tested, as compared to the DDP/H-TCA particles. The DDP/H-TCA particles got slightly bigger as the pH increased, going from a size of about 260 nm at pH 1.5 to about 300 nm at pH 7.

DOX loading and encapsulation studies. The amount of drug loading and the loading efficiency for each formulation was measured using UV-Vis absorption spectra at 490 nm and calculated from a standardized curve. The DOX release from the particles was examined in a pH 7.4 and a pH 5 phosphate buffer (PBS) using a dialysis method.

For each pH, 1 mL of DOX/CS-TCA particles or DDP/H-TCA particles (250 µg of DOX per sample) were prepared and loaded in a dialysis membrane (MWCO 3500 g/mol). The dialysis bag was placed in 20 mL of buffer and the buffer was stirred at 130 rpm at 37° C. At predetermined time points, 1 mL of external buffer was removed and the same volume of fresh buffer was added.

The amount of DOX present in the external buffer sample represented the released DOX, and the amount was calculated by measuring the absorbance of the sample at 490 nm and comparing that number to a standard calibration curve. The percent of drug loading and efficiency were then calculated using the equations below.

$$\text{Drug loading } (\%) = \frac{\text{weight of } DOX \text{ in nanoparticles}}{\text{weight of nanoparticles}} \times 100$$

$$\text{Drug Efficiency (\%)} = \frac{\text{weight of DOX present in nanoparticles}}{\text{weight of Dox used}} \times 100$$

The loading efficiency of DOX/CS-TCA and DDP/H-TCA was calculated to be about 61.6% and about 77.8%, respectively. The loading content of DOX/CS-TCA and DDP/H-TCA was determined to be about 30.8% and about 18.5%, respectively. The multiple layers present in the DDP/H-TCA formulation appear to provide a higher drug loading ability and a higher loading efficiency as compared to the DOX/CS-TCA formulation. However, in both formulations, high loading levels and a high loading efficiency of the drug has been achieved.

Figure 20A:
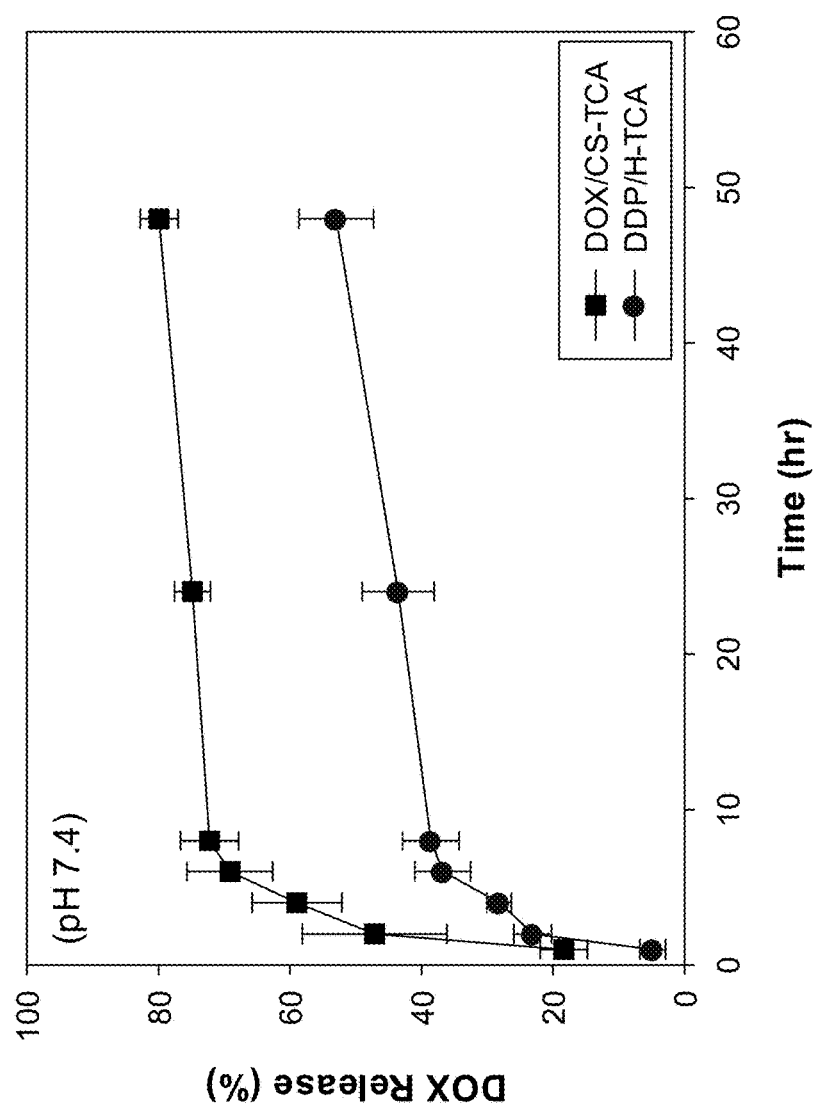
FIGS. 20A-20B are graphs of the release of drug over time at (FIG. 20A) pH 7.4 and (FIG. 20B) pH 5.0, for exemplary formulations.
Figure 20B:
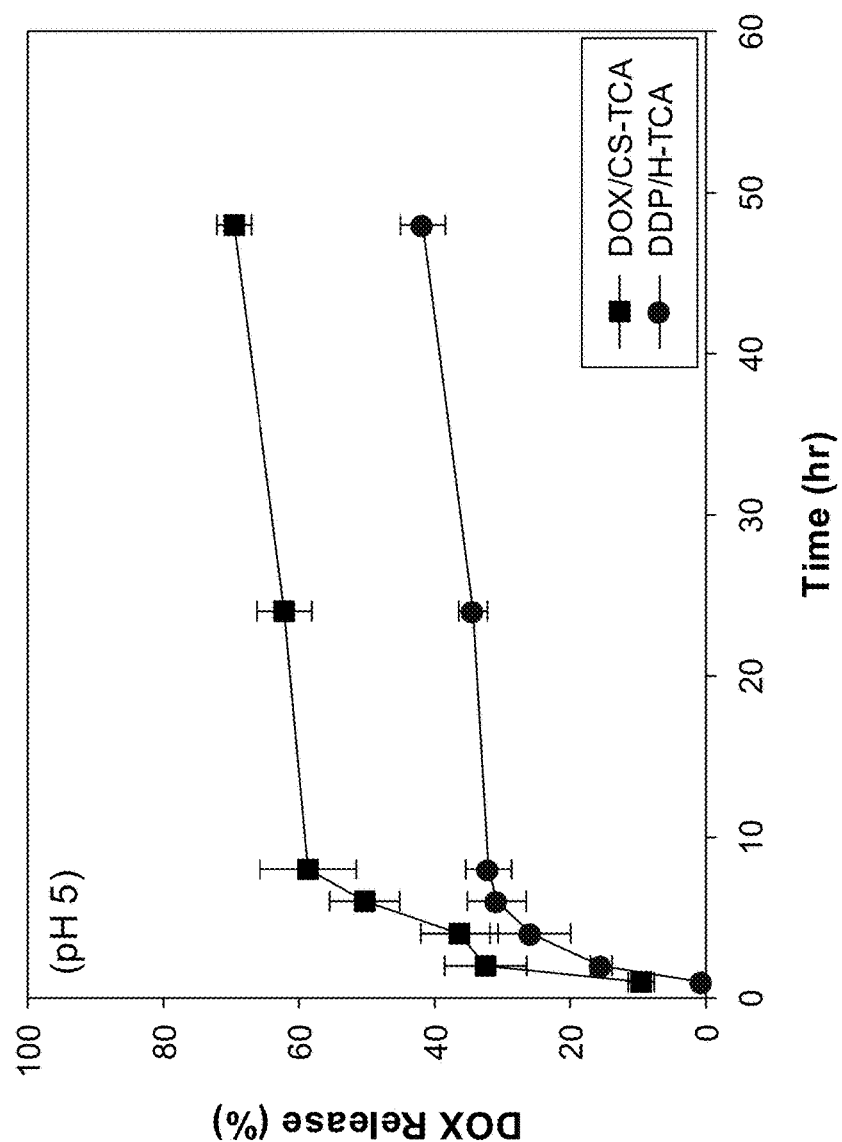

The data for release of drug from the two particle formulations is shown in FIGS. 20A and 20B. The data are presented as the mean±SD, with n=3. FIG. 20A is the data for the DOX release at pH 7.4 over time for DOX/CS-TCA formulation (upper line with square symbols), and for the DDP/H-TCA formulation (lower line with circle symbols). FIG. 20B is the data for the DOX release at pH 5 over time for DOX/CS-TCA formulation (upper line, square symbols), and for the DDP/H-TCA formulation (lower line, circle symbols).

The data indicates that a relatively rapid release of DOX within 24 hr was seen in DOX/CS-TCA formulations at pH 7.4, releasing around 75% of the drug in that time. The release of DOX from DDP/H-TCA formulations was slower, and around 50% of DOX was released at 48 hr. This indicates that a single coating can induce a faster release of drug from the particles. The multi-layered DDP/H-TCA particle may act as if it contains a diffusion barrier which can delay the DOX release, as it showed a slower release rate compared to that of the DOX/CS-TCA single coated particle. The release profile of DOX/CS-TCA indicated that it released DOX faster than the DDP/H-TCA composition.

At pH 5, the release rate of DOX from the formulations was delayed compared to the rate at pH 7. At pH 5, the DOX/CS-TCA formulation showed around 65% of DOX release at 48 hr and the DDP/H-TCA released about 40% of the DOX at 48 hr. This observation may be due to the high degree of protonation of the daunosamine group in DOX in an acidic environment. Therefore, DOX-loaded formulations may exhibit a slower release and a higher protonation of DOX at pH 5 (which corresponds to the endolysosomal pH), but an accelerated DOX release rate at pH 7.4. Since the nucleus is the target site of DOX where the pH is 7.4, the DOX should be released faster and available to intercalate DNA in the nucleus. These findings indicate that DOX release from DOX-loaded formulations is partially pH-controlled.

In vitro cytotoxicity of DOX-loaded particles. To evaluate the cytotoxicity of the polymers and DOX-loaded particles, samples were transfected in a dose-dependent manner and evaluated by an MTT-based cell viability assay using HepG2 cells. Cell Culture: HepG2 cells (a human hepatoma cell line) were cultured in DMEM supplemented with 10% FBS and D-glucose (4.5 g/L). Cells were grown and maintained under humidified air containing 5% $CO_2$ at 37° C. Cell Viability: a MTT assay was used to evaluate the cell viability of bile acid-linked polymers and DOX-loaded particles. HepG2 cells were seeded into a 96-well plate at a cell density of $5 \times 10^3$ cells/well in 100 µL media. After 24 hr, different concentration ranges (0.01-100 µg/mL) of DOX and DOX-loaded formulations were exposed to the cells for an additional 24 hr. MTT (10 µL; 5 mg/mL) solution was then added to the wells and incubated for 4 hr. All remaining media was aspirated, and DMSO (100 µL) was added to dissolve the formazan crystals produced from living cells with 10 min incubation at 37° C. The absorbance of the cells was measured at 570 nm and their cell viability was calculated.

Figure 21:
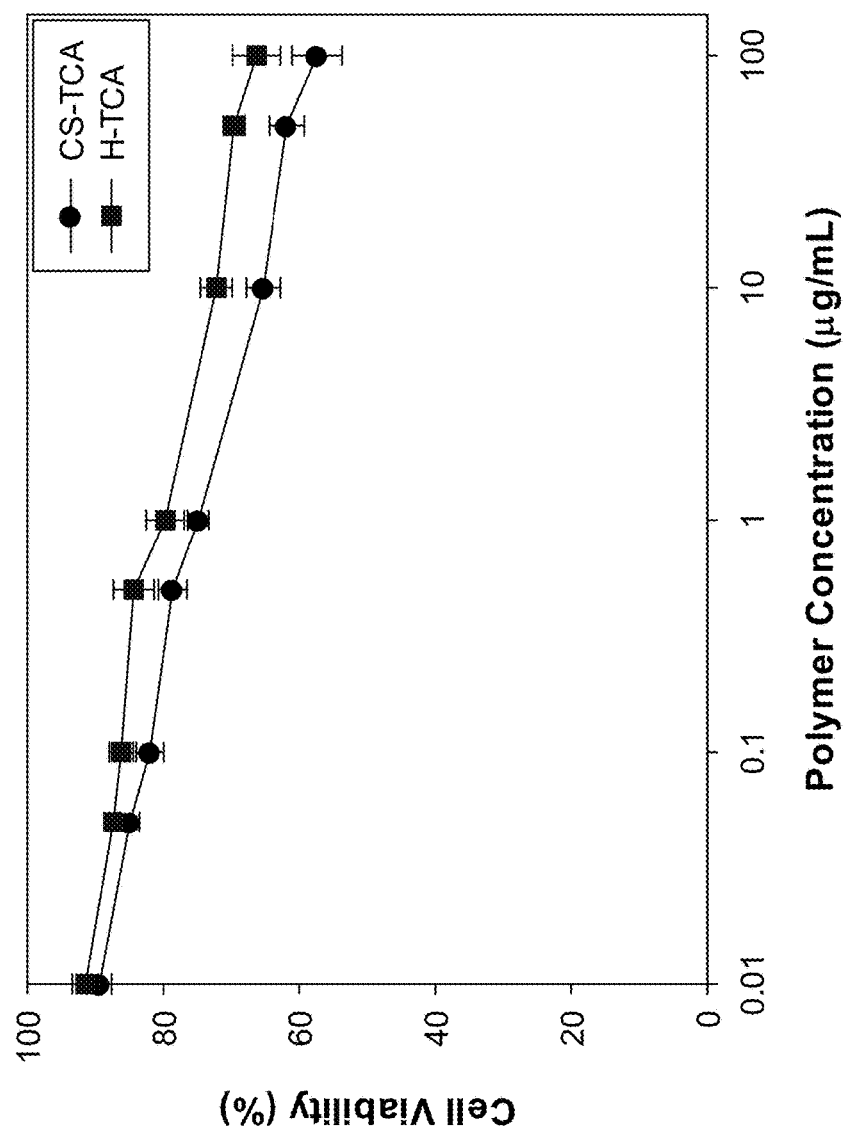
FIG. 21 is a graph reflecting the toxicity of exemplary bile acid-linked polysaccharides in HepG2 cells.

FIG. 21 shows the HepG2 cell viability after exposure to the H-TCA complex (upper line, square symbols) and the CS-TCA complex (lower line, circle symbols). The data are presented as the mean±SD, n=6. No DOX was present in these samples. The MTT assay of the bile acid-linked polymers showed that after incubation of the cells with either CS-TCA or H-TCA, about 90% and 60% of the original cell viability was maintained at 0.01 µg/mL and 100 µg/mL concentrations, respectively. This indicated a negligible cytotoxicity of these polymers.

Figure 22A:
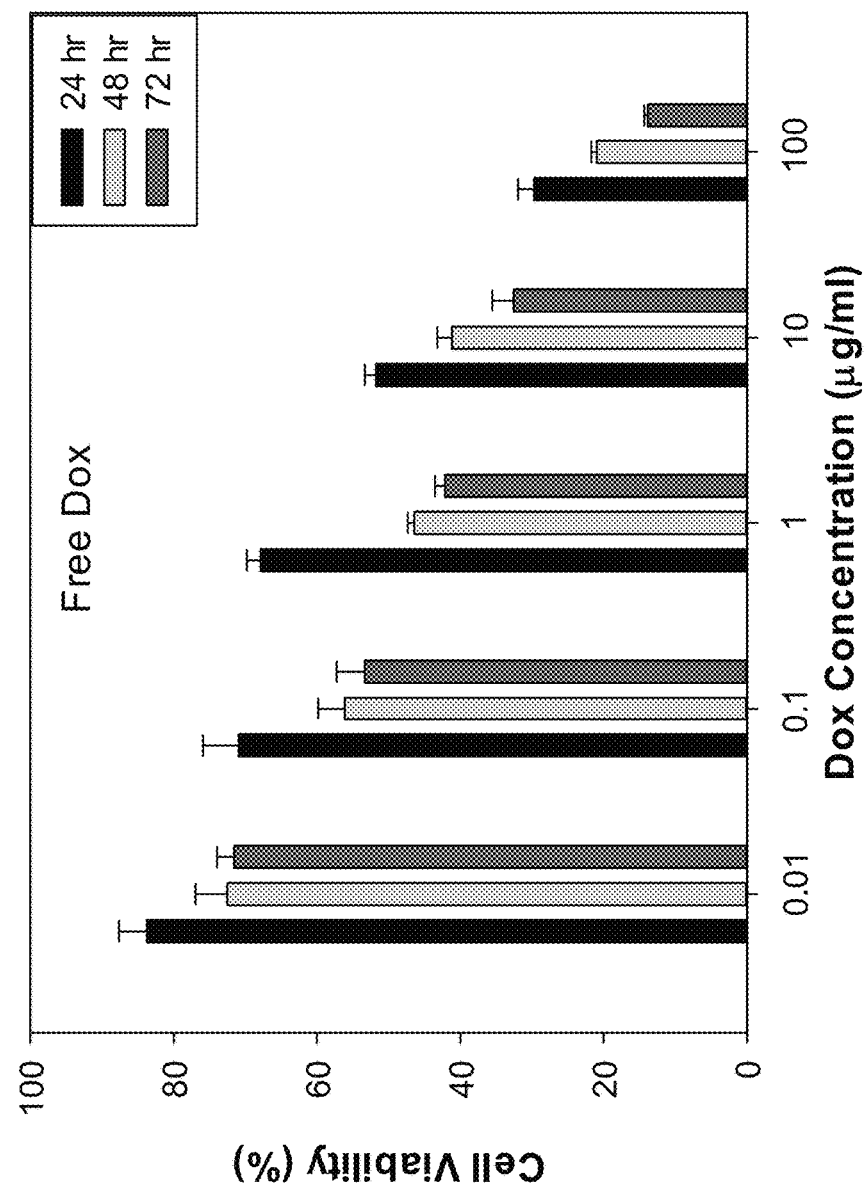
FIGS. 22A-22C are graphs showing the toxicity of exemplary formulations in HepG2 cells.
Figure 22B:
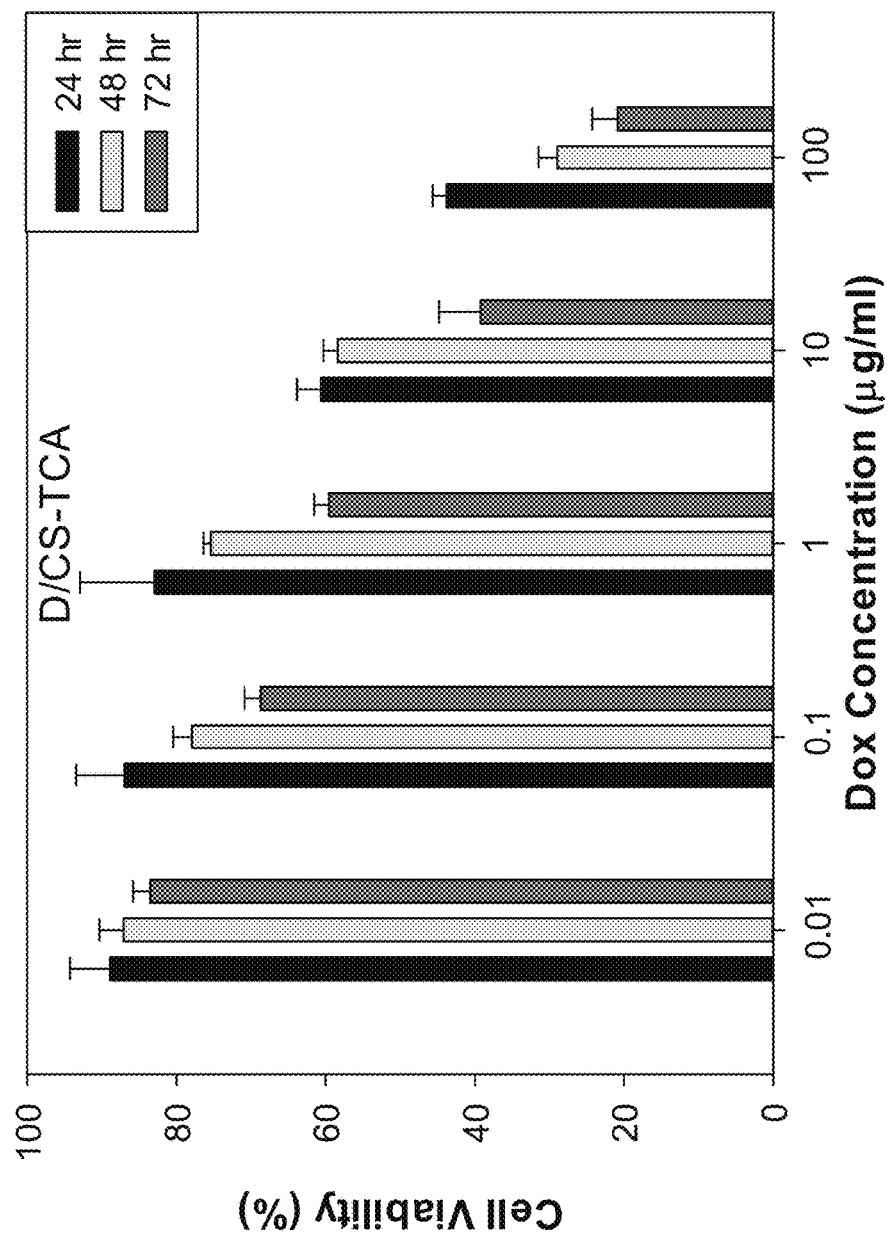
Figure 22C:
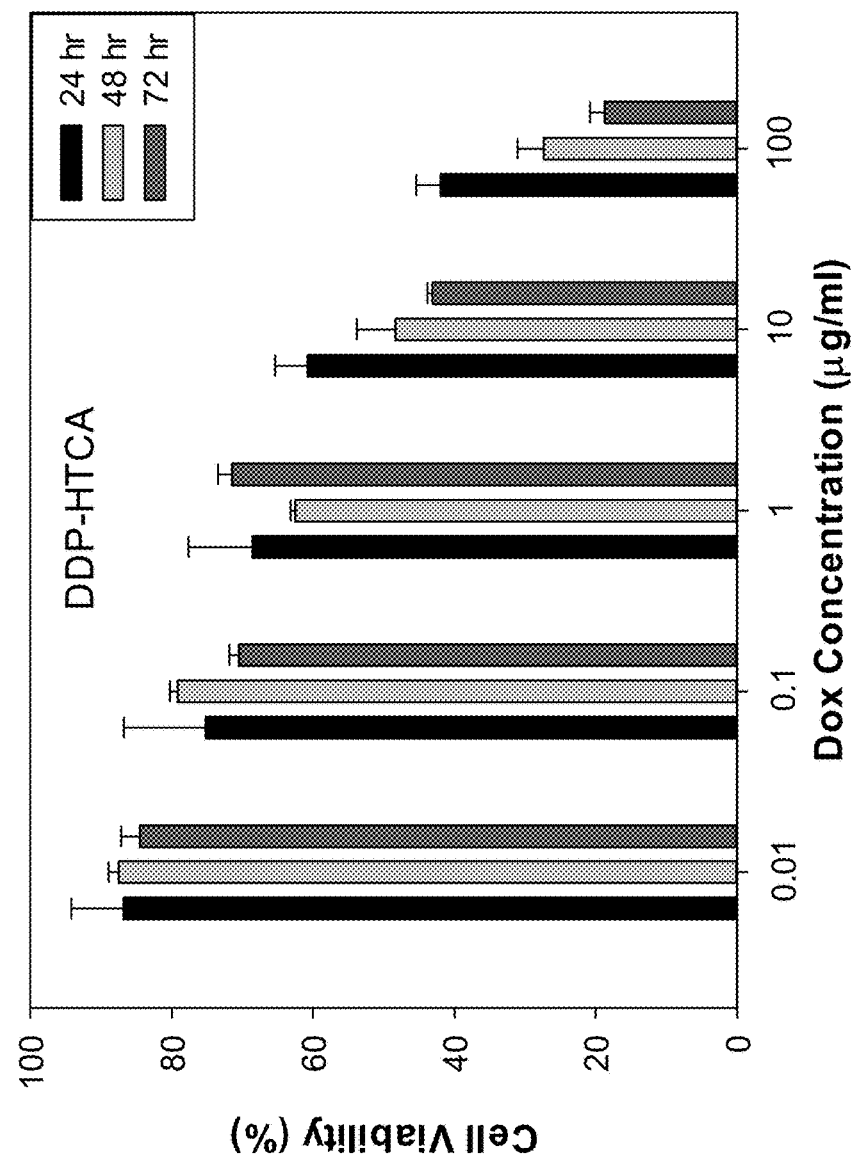

The cell viability of free DOX, the DOX/CS-TCA particles, and the DDP/H-TCA particles was also investigated in HepG2 cells after 24, 48, and 72 hr of incubation. The results are shown in FIGS. 22A-22C. The data are presented as the mean±SD, n=6. FIG. 22A shows the cell viability for free DOX at five concentrations (0.01, 0.1, 1, 10 and 100 ug/mL), after 24, 48 and 72 hr. FIG. 22B shows the cell viability for the DOX/CS-TCA formulation at the same five concentrations, also after 24, 48 and 72 hr. FIG. 22C shows the cell viability for the DDP/H-TCA multi-layered formulation at the same five concentrations, also after 24, 48 and 72 hr.

The data indicates that free DOX showed the highest dose-dependent cytotoxicity, likely due to the cationic properties of DOX which are more toxic to cells. For the DOX/CS-TCA formulation and the DDP/H-TCA formulation, the DOX-loaded particles showed lower toxicity compared to free DOX, and the DOX/CS-TCA formulation displayed a slightly lower toxicity than the DDP/H-TCA formulation. The CS-TCA or H-TCA anionic polymer coating improved DOX-induced cytotoxicity (i.e. increased the cell viability), thus, lower cell toxicity from the DOX-loaded formulations were observed. However, the multi-layered coated DDP/H-TCA complex showed a slightly higher toxicity than the singly-coated DOX/CS-TCA formulation. These results may be due to the presence of up to three different polymers coating the DOX.

In vivo efficacy in a tumor bearing animal model. The in vivo anticancer efficacy of free DOX and the DDP/H-TCA composition was evaluated in a HepG2 xenograft mouse model. Animals which were treated with free DOX delivered via both orally and via IV administration were used as a control group, and DDP/H-TCA compositions were administered orally every 3 days at a dose of 4 mg DOX/kg, up to 18 days.

HepG2 cells ($5 \times 10^6$ cells/mL) in 100 µL PBS were injected subcutaneously into the back of each mouse. When the tumor size reached approximately 100-150 mm$^3$, each mouse received an oral administration of PBS, 4 mg/kg DOX, or 4 mg/kg DOX in a DDP/H-TCA composition, once every three days. In addition, an equal amount of doxorubicin was intravenously (IV) administered in a control group. Tumors were measured every three days with a digital caliper and the tumor volume was calculated using the equation shown below.

$$\text{Tumor volume} = \text{Length} \times \frac{\text{Width}^2}{2}$$

To achieve a relatively high concentration, the lyophilized powder of DDP/H-TCA particles was reconstituted in DI water just prior to in vivo administration. First, the tumor growth inhibition efficacy of bile acid-coated DOX-loaded particles was investigated in a mouse xenograft model. Doxorubicin (DOX) at a dose of 4 mg/kg, or an equivalent amount of DOX formulated as DDP/H-TCA particles, was prepared and delivered via IV or oral administration every 3 days up to 18 days to monitor tumor progression. DOX-loaded particles without a bile acid (i.e. no TCA) were also tested as a non-targeted control formulation to evaluate the tumor inhibition efficacy of the TCA. Because tumors in the PBS control group were quite aggressive and reached over 10% of the animals' body weight around day 18, all treatments were terminated and all mice were sacrificed at day 18.

Statistical analysis. The Student's t-test was used to compare two groups, and one-way ANOVA with a bonferroni post-hoc analysis was used to compare three or more groups, with $p<0.05$ considered statistically significant.

Figure 23A:
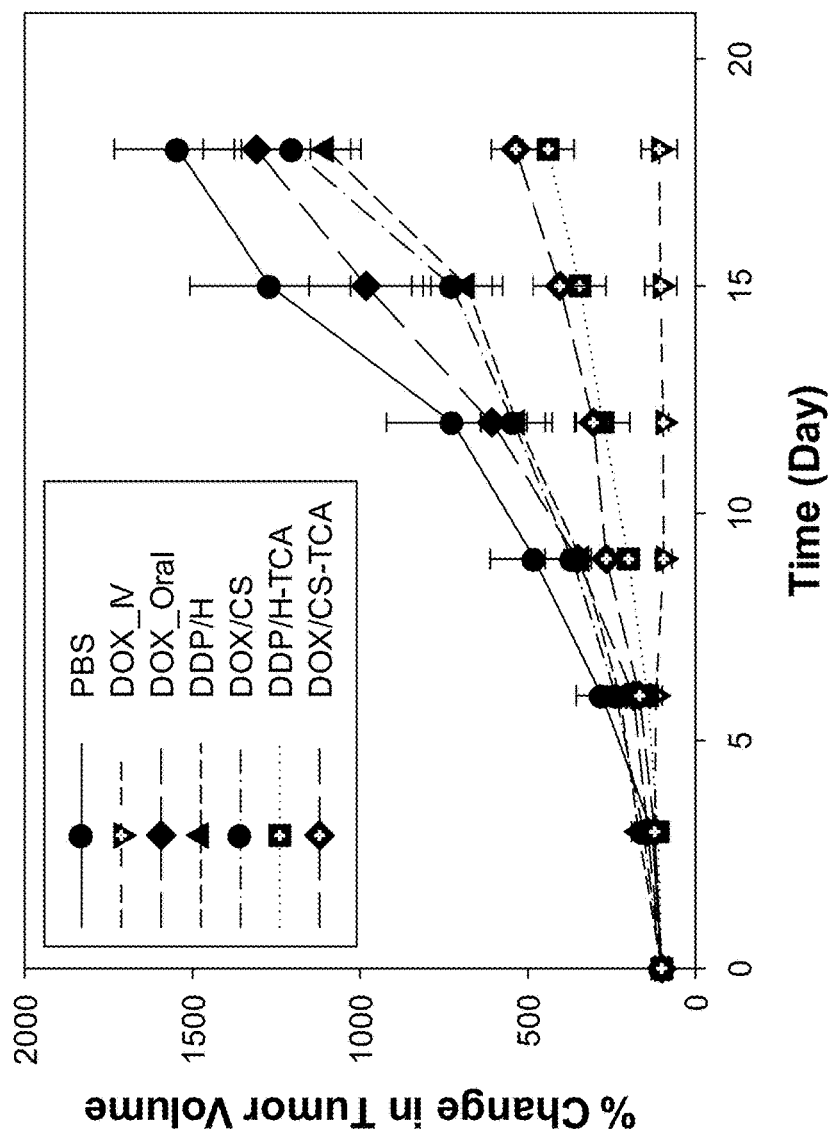
FIGS. 23A-23C are graphs of efficacy for exemplary formulations.
Figure 23B:
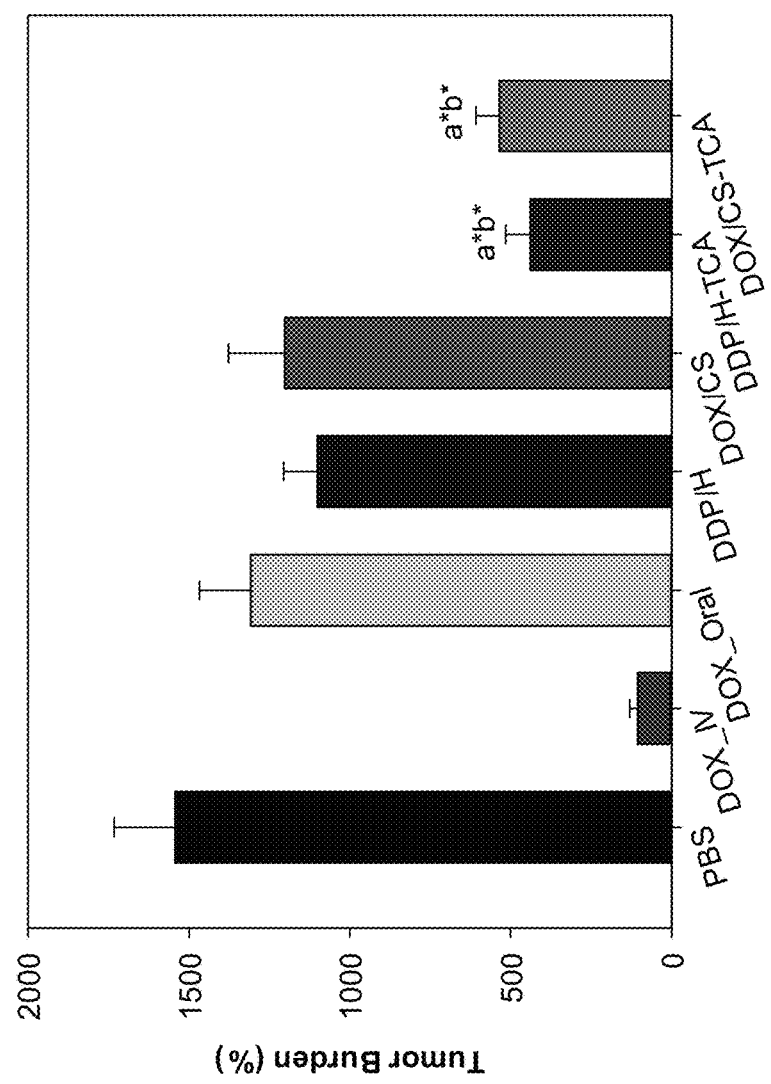
Figure 23C:
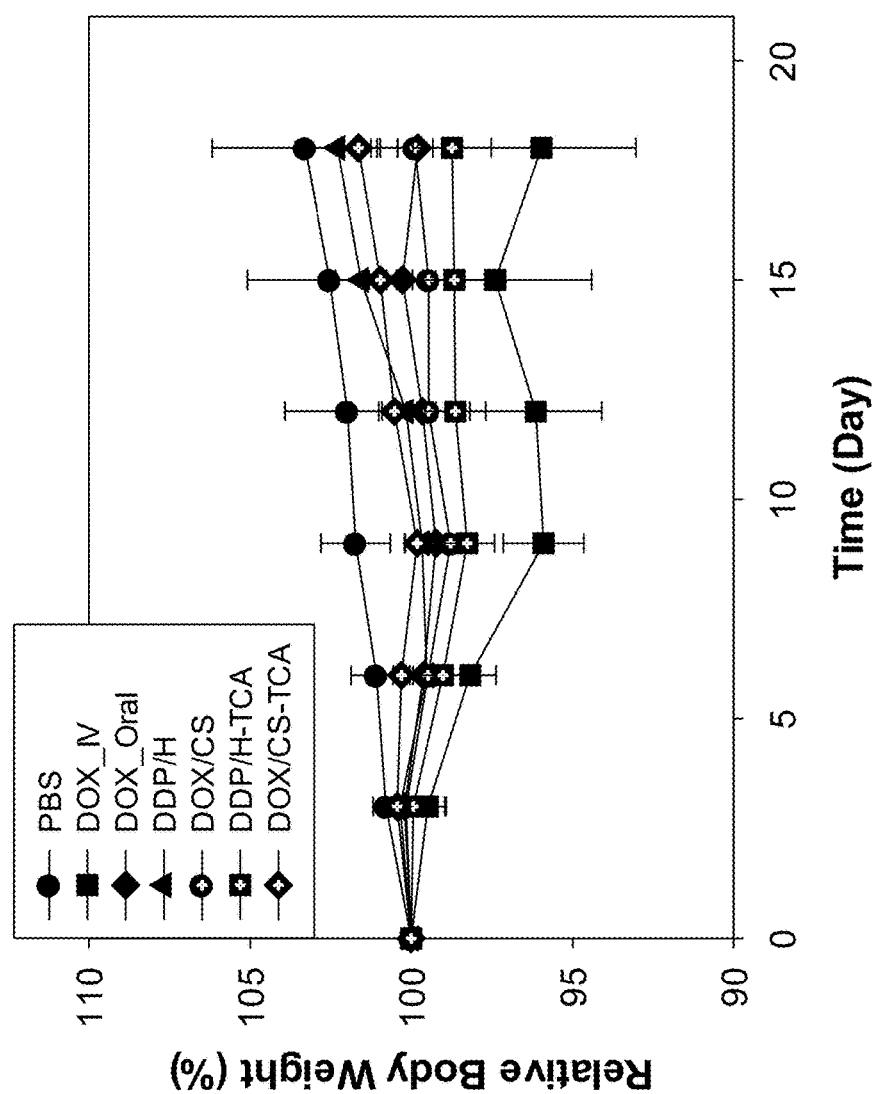

FIGS. 23A-23C show the antitumor efficacy of the formulations. All the treatment groups showed an increase of tumor volume over time. However, there was a significant difference in tumor growth rate and overall tumor volume change depending upon the formulation used for the treatment. The data are presented as the mean±SEM, n=3.

FIG. 23A shows the percent change in the tumor volume in the mice over time for the 7 formulations used in the study; the PBS control; free DOX administered by IV; free DOX administered orally; a DDP/heparin complex (no bile acid); a DOX/chondroitin sulfate complex (no bile acid); and the two bile-acid wrapped DOX compositions (DDP/H-TCA and DOX/CS-TCA).

As shown in FIG. 23A, the tumor volume in the free DOX IV group (the dashed line with inverted triangles) showed the greatest inhibition of tumor growth. However, a greater amount of suppression of tumor growth was observed in mice treated with bile acid-wrapped DOX particles (the dotted line with squares and the large dashed line with marked diamonds) compared to that of the other oral control groups. The tumor volumes in the bile acid-wrapped DOX groups were significantly smaller ($p<0.05$) than the tumor volumes of the mice administered free oral DOX (large dashed line with filled diamonds). The tumors in the free oral DOX group had an almost 1400% increase in volume, whereas the tumors in the DDP/H-TCA and DOX/CS-TCA groups displayed an only 400% and 600% increase in volume, respectively. The tumors in the DOX/CS-TCA group showed a slightly greater increase in tumor volume than the tumors in the DDP/H-TCA group, and this result may be caused by the faster release of DOX from DOX/CS-TCA complexes as compared to DDP/H-TCA complexes. In contrast, tumors treated with non-bile acid DOX-polysaccharide complexes (small dashed line with triangles and dot-dashed line with circles) did not have a significant inhibition of tumor growth and generally showed no marked change in the rate of tumor growth compared with the free oral DOX group. There was no significant difference in tumor volume between the free DOX oral group and non-TCA group.

FIG. 23B shows the percent change in tumor burden in the treated animals. The changes indicated by the starred values (a and b on the right-most bars) have a $p<0.05$ as compared to oral free DOX. The two bile-acid wrapped DOX compositions (i.e. the DDP/H-TCA and DOX/CS-TCA labeled bars) were more efficacious at tumor growth reduction compared with mice treated with non-TCA DOX complexes (i.e. the DDP/H and DOX/CS labeled bars). The tumor regression shown in the two bile-acid wrapped DOX groups suggests a strong anti-tumor effect for two bile-acid wrapped DOX formulations in the HepG2 xenograft cancer model. The measured tumor burden on day 18, as shown in FIG. 23B, represented a considerable reduction in tumor burden in the animal groups that received the DOX-TCA particles as compared to the tumor burden in the free oral DOX group.

The body weight of the mice was also measured throughout the treatments to assess the toxicity induced from the treatments. This data is shown in FIG. 23C, which is a graph of the relative body weight percentage of the treatment groups over time.

As seen in FIG. 23C, the PBS and two DOX control groups, as well as the non-TCA treated groups (i.e. the DDP/H and DOX/CS groups) showed no significant weight loss in the beginning of the treatment, and a small weight gain in the mice was observed over time which indicated no serious toxicity due to the treatments. However, there was some weight loss seen in the animals in the DDP/H-TCA group, but a slow weight gain was observed towards the end of the study.

Biodistribution. A biodistribution study was performed in HepG2 tumor-bearing NOD/SCID mice. The major organs and intestinal tract of each mouse were collected 4 hr after administration of the formulations. The liver, kidney, heart, stomach, small intestine including duodenum, jejunum, ileum, and tumor of each mouse was collected and suspended in 70% ethanol with 0.3 N HCl. The samples were then homogenized to extract the doxorubicin, and then the samples were refrigerated for 24 hr and centrifuged to collect supernatant. For analysis, 200 μL of the supernatant was loaded in a black opaque plate and DOX fluorescence was measured using a plate reader, where the wavelengths of excitation and emission were 470 and 590 nm, respectively.

Figure 24:
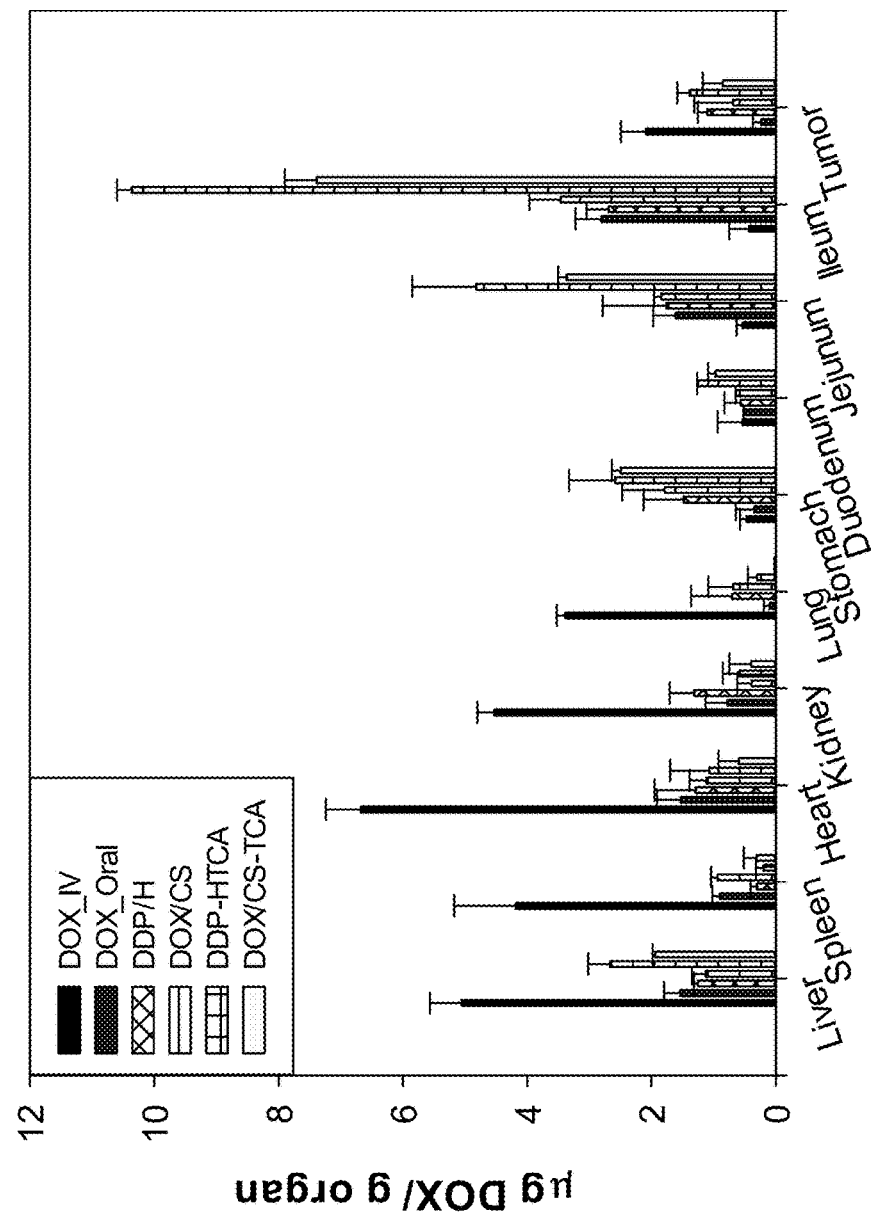
FIG. 24 is a graph showing the biodistribution of doxorubicin in tumor-bearing mice after administration of exemplary compositions.

The results of the biodistribution study are shown in FIG. 24. The data are presented as the mean±SEM, n=3. The concentration of DOX was measured in the major organs and intestine of each mouse by measuring the DOX fluorescence intensity, and the results are presented as μg DOX per gram of tissue. Notably, a higher concentration of DOX was seen in the heart and liver tissues after IV injection of free DOX than in any of the orally administered groups.

The data indicates that the highest amount of DOX for the oral formulations was observed in the ileum of samples treated with the two bile-acid wrapped DOX compositions (i.e. the DDP-HTCA and DOX/CS-TCA bars). The DOX content in the ileum for mice treated with these two compositions was around 3 to 4-fold higher than that in the free DOX oral or non-TCA groups. The amount of DOX accumulation in the ileum is an indication of targeted absorption of the bile-acid wrapped DOX compositions and suggests the effective uptake of bile-acid wrapped DOX compositions by the bile acid transporters present in the ileum. Moreover, an improved accumulation at tumor sites was also observed. These results suggest that oral bile acid-mediated DOX absorption leads to a higher DOX concentration in the blood stream compared to the concentration after administration of oral free DOX. As a consequence, the relatively higher accumulation in the blood stream may contribute to slow tumor progression (superior DOX efficacy) compared to free DOX oral administration.

In conclusion, a statistically significant suppression of tumor growth was seen, without a marked reduction of body weight, in the animals treated with bile-acid wrapped doxorubicin compositions. In addition, a biodistribution analysis suggested that the animals treated orally with bile-acid wrapped doxorubicin compositions showed a higher absorption of doxorubicin from the ileum than those treated orally with free doxorubicin. The animal data showed that the bile acid coating not only diminished the toxicity of doxorubicin, but also enhanced its absorption in the intestine, particularly in the ileum. These findings indicate that enterohepatic circulation of bile-acid wrapped doxorubicin compositions appears to elevate the systemic levels of DOX and increase DOX plasma levels, which leads to oral bioavailability enhancement and tumor growth reduction.

The bile-acid wrapped doxorubicin particles showed no change in stability upon freeze-drying, which indicated the possibility of long-term storage. The bile acid coating also showed negligible toxicity compared with free DOX, and provided for high drug loading efficiency and a pH-dependent drug release. Importantly, the in vivo results showed that the bile-acid wrapped doxorubicin compositions significantly delayed tumor growth. Biodistribution studies also demonstrated an improved absorption of the doxorubicin from the bile-acid wrapped doxorubicin particles in the ileum of the intestine. Overall, orally administered formulations containing a bile acid showed a higher therapeutic efficacy for solid tumors than free DOX and non-bile acid-containing formulations. This indicates that the bile acid-mediated targeted delivery enhanced the therapeutic performance of doxorubicin by utilizing bile acid transporters, which leads to an enhancement in its oral absorption. Thus, bile acids are a proven effective carrier for the oral delivery of doxorubicin. In addition, these new formulations may allow for the feasibility of switching the route of administration of certain anticancer or chemotherapeutic drugs from intravenous to oral.

Figure 25:
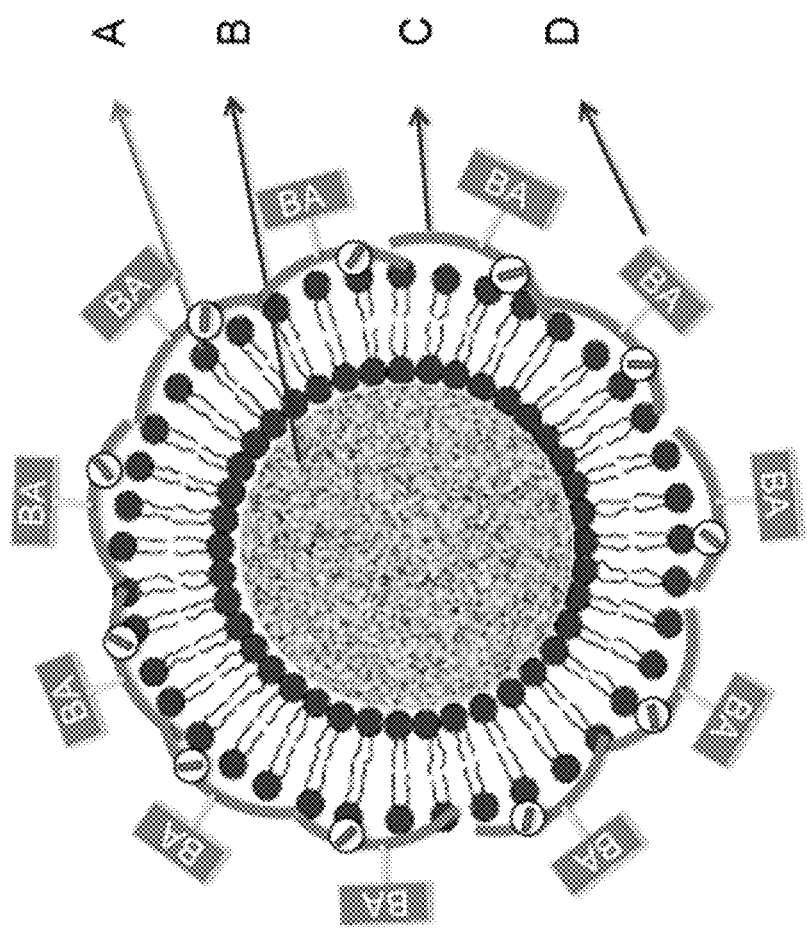
FIG. 25 is an illustration of the general structure of a liposomal exemplary therapeutic composition, made with 4 components labeled A, B, C and D.

Example 4. Therapeutic Compositions Comprising a Bile Acid and/or Bile Acid Conjugate, a Liposome, and a Therapeutic Agent The therapeutic compositions disclosed herein which contain a core complex having a bile acid or bile acid conjugate on their surface, may also contain lipids or a layer of lipids, such as a liposome. The liposome may form an exterior surface of the core complex, and may be cationic in nature. Thus, certain of the inventive compositions may be made with a therapeutic agent encompassed, completely or in part, within a liposome which has a cationic surface, to form the core complex. Such a liposomal core complex can interact electrostatically with an anionic polymer which is covalently bound to a bile acid or bile acid conjugate. One embodiment of such a liposomal composition is illustrated in FIG. 25, where A is a cationic liposomal composition (shown as a phospholipid bilayer), which can contain a single cationic lipid, or a mixture of neutral and cationic lipids, but has a surface with a net positive charge at a pH of 5; B is a therapeutic agent, which include a protein, peptide, DNA, gene or a small-molecule drug; C is an anionic polymer, which may be biodegradable and/or injectable, including heparin, chondroitin sulfate, and hyaluronic acid, and which has a net negative charge at neutral pH; and D is a bile acid or a bile acid conjugate (BA) which is covalently bound to the anionic polymer C.

The composition shown in FIG. 25 is illustrated as spherical and with each layer completely encompassing the interior core. In certain embodiments, each layer does not encircle completely the core and/or an interior layer, and the composition is not spherical.

The successful design of a delivery approach which can be used for a variety of different therapeutic agents, including DNA-based, protein and conventional small molecule drugs, may include the use of functionalized liposomes. Such an approach requires the sophisticated control of the assembly of micrometer-sized structures to achieve the desired properties. Here, the use of drug-loaded liposomes which were wrapped with an anionic polymer covalently bound to a bile acid or bile acid conjugate was investigated.

Figure 26:
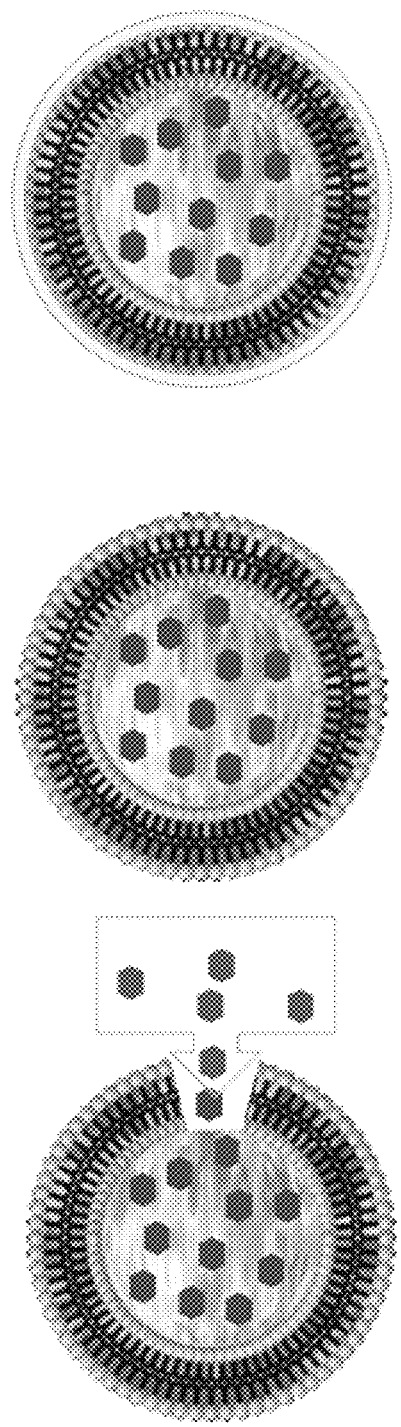
FIG. 26 is an illustration of the process of loading a liposome with a therapeutic agent and subsequent coating of the closed liposome with a bile acid or bile-acid conjugate covalently bound to an anionic polymer.

To load the therapeutic agent into the liposome, a number of schemes can be envisioned. One scheme has the therapeutic agent incorporated into the bilayer, completely or in part, which can be formed by building the liposomal bilayer in the presence of the agent. Another scheme incorporates the therapeutic agent completely within the interior of the liposome and not significantly interacting with the phospholipid bilayer. To load the therapeutic agent into the liposome in this scheme, it is possible to build the liposome in the presence of the agent and let the liposomal bilayer self-assemble around the agent. Alternatively, the liposome can be formed separately from the agent, and the agent can be added through a temporary hole in the liposome and the liposome spontaneously sealed by lateral diffusion of the phospholipids. This approach is used in the experiments described herein, and shown schematically in FIG. 26.

Thus, high-density superparamagnetic $Fe_3O_4$ nanoparticles were dispersed in a liposome and a high load was applied in a particular direction to the liposome membrane to generate open lipid bilayer holes. The designed experimental conditions enabled the formation of one or multiple open pore sites in liposome membranes. The open lipid bilayer holes in liposome membranes were used as an entrance to insert a therapeutic agent (including genes, proteins, or small molecule drugs) into the liposomes prior to the natural recovery (i.e., closing) of the lipid bilayer holes.

Lipids with suitable hydrophilic/lipophilic proportions can self-assemble in aqueous solutions into vesicular lipid bilayers. Hydrophilic or lipophilic bioactive species can be contained in a hydrophilic inner core or a lipid bilayer shell, respectively. Liposome-based delivery systems for chemical or biological molecular candidates offer various possibilities in the biomedical and other fields.

The dynamic properties of lipid bilayers, including their fusion, fission, and shape deformation, can be affected by various experimental conditions. The generation of a structure-transformed liposome that evolves from a conventional lipid bilayer structure represents a means for designing highly efficient liposomal drug carriers. Herein, a method of forming liposomes with open lipid bilayer holes (hereafter referred to as partially uncapped liposomes, or "UCLs") is disclosed, which use highly dense and superparamagnetic $Fe_3O_4$ nanoparticles and a magnetic impeller with a tailor-made magnet. Under magnetic shear stress, the $Fe_3O_4$ nanoparticles dispersed in the liposome apply stress to a specific position of the lipid membrane via the strong magnetic field and the magnetic shear stress consequently squeezes the liposome surface and tears it, to form open lipid bilayer holes. This is illustrated schematically in FIG. 27.

This method has been used to prepare liposomes which have been coated with a bile acid or bile acid conjugate which has been covalently bonded to an anionic polymer (chondroitin sulfate) and loaded with insulin and doxorubicin.

Materials and methods. Chemicals and solvents were obtained from Sigma-Aldrich (USA) unless otherwise noted. $Fe_3O_4$ nanoparticles (average 7 nm in diameter, prepared after the chemical reaction of iron (III) acetylacetonate, 1,2-hexadecanediol, oleic acid, and oleylamine in benzyl ether at 200° C. for 2 h and 300° C. for 1 h) were synthesized as described in Lee et al, Int. J. Pharm. 471, (2014), 166-172.

(I) Liposomal Insulin.

Three sets of liposomes were prepared and labeled insulin was inserted into them. One of the sets was coated with chondroitin sulfate (CS) and one set was coated with chondroitin sulfate which had been covalently bound to taurocholic acid (CS-TCA), prepared as described for Example 1. The molar ratio of CS:TCA used in the coupling is 1:4, and its preparation is shown in Scheme 1.

Figure 27:
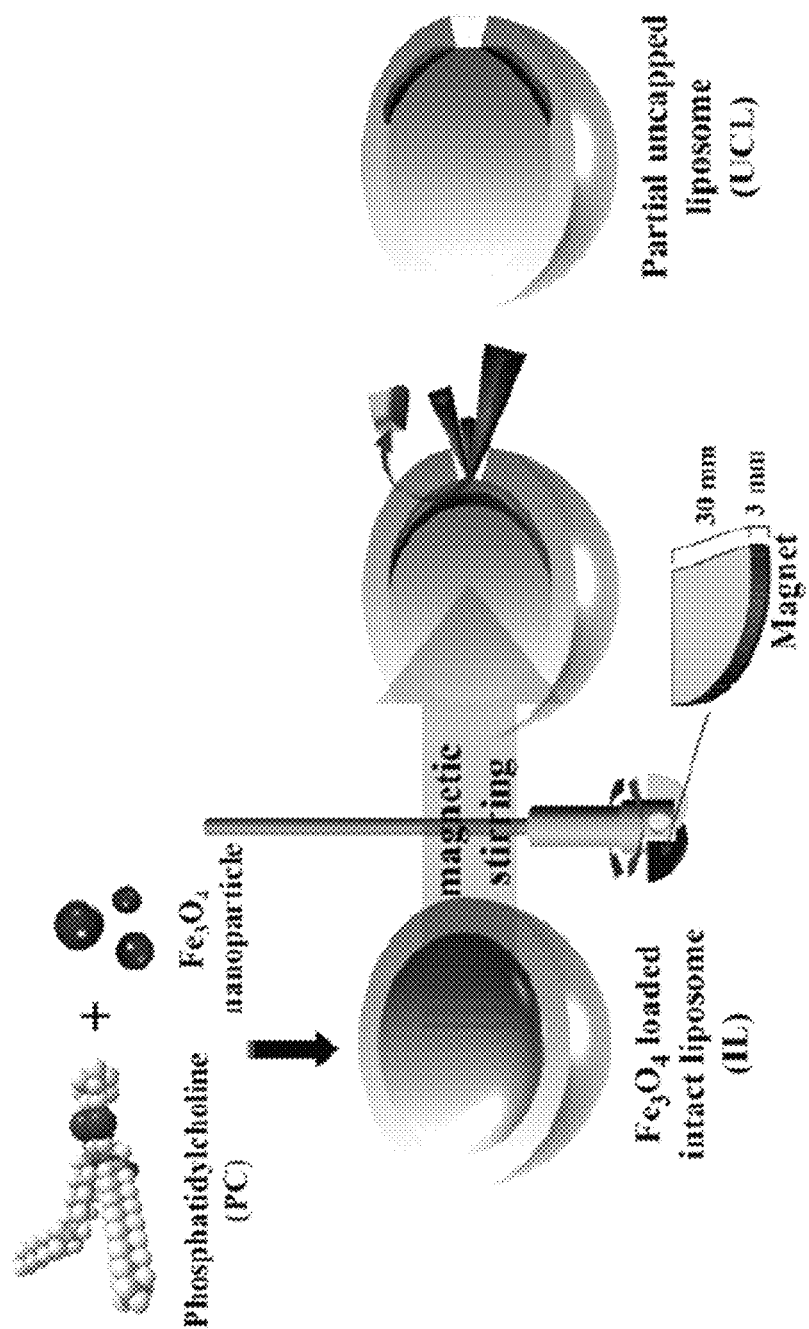
FIG. 27 is an illustration of the formation of a partially uncapped liposome.

Liposome preparation for the protein therapeutic agent studies. The liposomes were generally prepared as described in Kwag et al, Colloids and Surfaces B: Biointerfaces, 135 (2015), 143-149. Dimethyl dioctadecyl ammonium bromide ("DD") (20 mg), deoxycholic acid ("DOCA") (5 mg) and $Fe_3O_4$ nanoparticles (0.5 mg) dissolved in chloroform (5 mL) were added to a round-bottomed flask. The solvent in the round-bottomed flask was removed by rotary evaporation to form a thin film on the surface of the flask. The film was rehydrated in 150 M PBS (pH 7.4, 20 mL) using a sonicatory (60 Hz for 5 min) at 25° C. The obtained liposomes were slowly mixed using a magnetic impeller with a tailor-made magnet formed with two quarter-circles (30 mm in radius and 2 mm thick) as shown in FIG. 27. The liposomes that stuck to the magnet were again stirred at 25° C. for 1 min using a magnetic impeller at 1500 rpm) with the tailor-made magnet. After the liposome solution was magnetically stirred, ring-shaped, neodymium rare-earth magnets (10 mm in radius and 10 mm thick) were immediately attached to the bottom of the flask to remove the free $Fe_3O_4$ nanoparticles that had leaked from the liposomes.

A control or "blank" set of liposomes was prepared without the $Fe_3O_4$ nanoparticles, following the conventional film rehydration method, using the same ratio of dimethyl dioctadecyl ammonium bromide and deoxycholic acid as described above.

An additional set of liposomes were prepared as above, but without the deoxycholic acid ("DOCA") added to the solution. Thus, these liposomes contained only dimethyl dioctadecyl ammonium bromide ("DD") in the liposomal bilayer.

Ce6-Insulin preparation and loading. Insulin was labeled with Ce6 to allow for its detection with NIR fluorescence spectroscopy. The carboxylic acid groups in Ce6 were used to attach to the insulin. Ce6 (0.1 mM) was reacted with excess insulin (10 mM) at room temperature for 3 days, in the presence of EDC (5 mM) and NHS (5 mM) in 10 mL of deionized water, to produce Ce6-conjugated insulin. The resulting solution was then purified by dialysis (2 days) using a Spectra/Por MWCO 3.5K membrane against fresh deionized water to remove any uncoupled reagents. The solution was then freeze-dried for 2 days.

Liposomes made with just dimethyl dioctadecyl ammonium bromide ("DD") and liposomes made with DD and DOCA were loaded with the labeled insulin, as were the "blank" liposomes. The appropriate liposome (20 mg) was dispersed in 150 mM PBS (pH 7.4, 20 mL) and slowly stirred (30 rpm) with insulin (10 mg) at 25° C. for 2 hours, which enabled facile protein encapsulation through the open pores of the UCLs.

A portion of the insulin-loaded liposomes made with both DD and DOCA were mixed with chondroitin sulfate (20 mg/mL) at 14,000 rpm for 30 seconds, to provide insulin-loaded liposomes coated with chondroitin sulfate.

A portion of the insulin-loaded liposomes made with both DD and DOCA were mixed with chondroitin sulfate which had been covalently bound to taurocholic acid (CS-TCA, 20 mg/mL), prepared as described in Example 1, at 14,000 rpm for 30 seconds, to provide insulin-loaded liposomes coated with CS-TCA.

A summary of the three sets of liposomal samples is shown in Table 1, below.

TABLE 1

Samples of liposomal formulations

| Sample | Preparation condition for partially-opened liposomes | | | | | Coating on liposome surface | |
|---|---|---|---|---|---|---|---|
| | Lipid | Lipid charge | $Fe_3O_4$ NP | DOCA | Insulin | CS | CST |
| DD0 | DD 50 mg | (+) | 0.5 mg | — | 10 mg | — | — |
| DD1-CS | DD 50 mg | (+) | 0.5 mg | 5 mg | 10 mg | 20 mg | — |
| DD1-CST | DD 50 mg | (+) | 0.5 mg | 5 mg | 10 mg | — | 20 mg |

Dimethyl dioctadecyl ammonium bromide (DD)
chondroitin sulfate (CS)
Deoxycholic acid (DOCA)
CS-taurocholic acid (CST) conjugate The protein loading efficiencies of the protein-loaded liposomes were determined after measuring the free insulin concentration using a BCA protein assay kit in the supernatant of the liposome solution, which was centrifuged at 20,000 rpm for 10 min. The insulin loading efficiency was defined as the weight percentage of the insulin entrapped in the liposomes relative to the initial insulin feeding amount.

The insulin loading efficiency of the CS or CS-TCA coated liposomes was greater than 40% after 2 hr of treatment, and the insulin loading efficiency of the blank liposomes was less than 5% after 4 hr of treatment. The insulin loading content of the liposome was calculated by a weight percentage ratio of insulin in the liposome, and was found to be about 8 weight percent for each liposome.

Particle size distribution and Zeta-potential analysis. The particle size distributions of the liposomes (1 mg/mL, PBS) were measured using a Zetasizer 3000 instrument (Malvern Instruments, USA), which was equipped with an He—Ne laser with a wavelength of 633 nm and a fixed scattering angle of 90°. The zeta potential charge of the liposome solution (1 mg/mL, PBS) was measured using the Zetasizer 3000 instrument (Malvern Instruments, USA). Prior to the analysis, the liposome solution was stabilized at room temperature for 2 hr.

Figure 28:
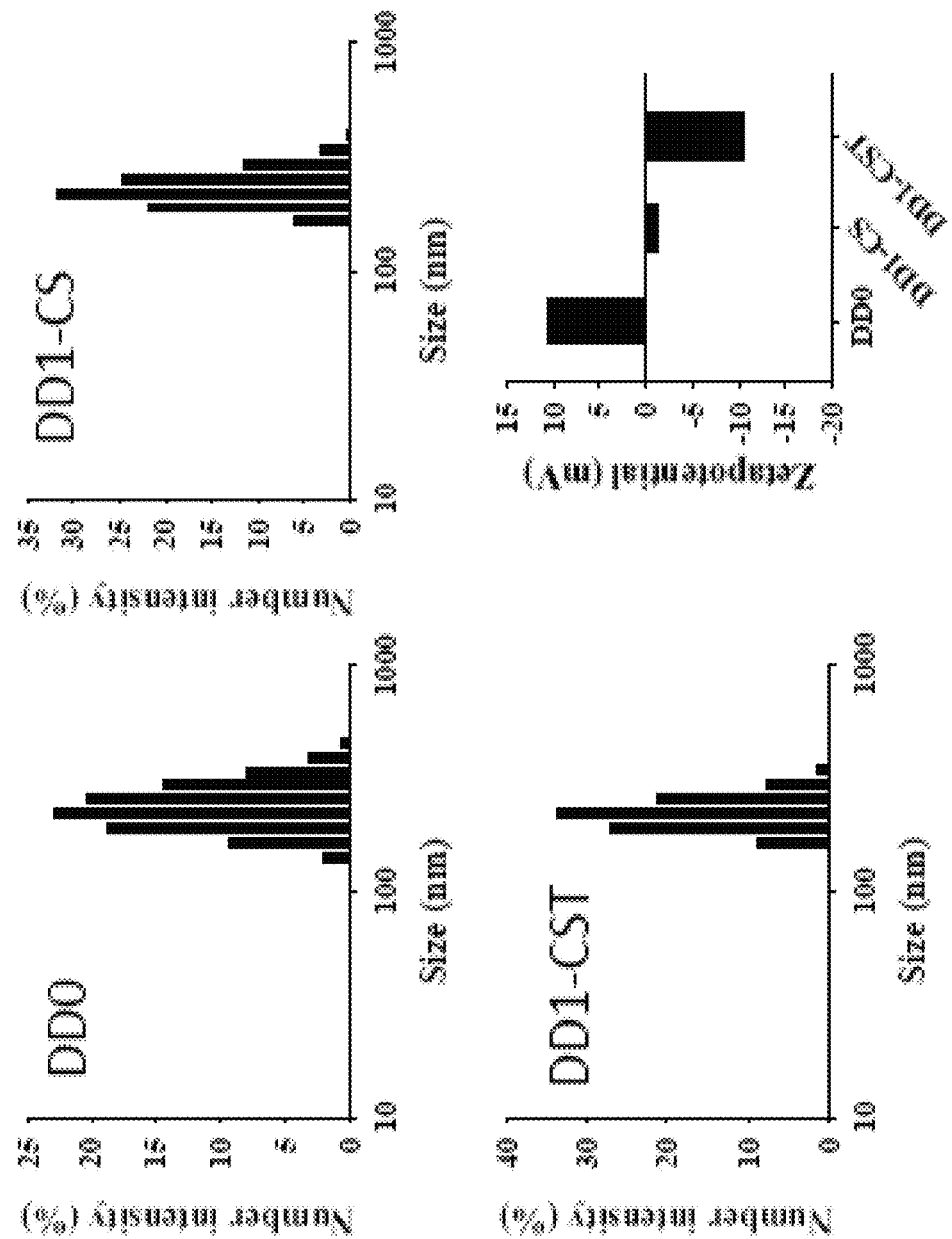
FIG. 28 are graphs showing the average size and Zeta potential of three exemplary liposomal compositions.

The particle size and zeta potentials of the protein-loaded liposomes are shown in FIG. 28, and summarized in Table 2, below.

TABLE 2

Data for sample liposomes.

| Sample | Insulin loading efficiency (%) | Zeta-potential (mV) | Average size (diameter, nm) |
| --- | --- | --- | --- |
| DD0 | 43.67 | 10.63 | 220 |
| DD1-CS | 41.69 | −1.19 | 221 |
| DD1-CST | 40.42 | −10.50 | 220 |

Protein release. The liposomes were dispersed in PBS (1 mg/mL, pH 7.4, with 0.01% sodium azide) and were added to a dialysis membrane bag (Spectra/Par® MWCO 3.5 KDa). The dialysis membrane bag was sealed and subsequently immersed in a vial containing fresh PBS (10 mL, 150 mM). The release of insulin from the liposomes was induced by mechanical shaking (100 rev./min) at 37° C. The outer phase of the dialysis membrane bag was extracted and replaced with fresh buffer solution at predetermined time intervals (0-24 hr). The insulin concentration in the extracted solution was calculated using a BCA protein assay kit. In addition, circular dichroism (CD) analysis of insulin in the extracted solution at 4 hr post-incubation was performed using a J-815 CD spectrometer (Jasco International, UK) to evaluate the insulin stability (n=3).

Figure 29:
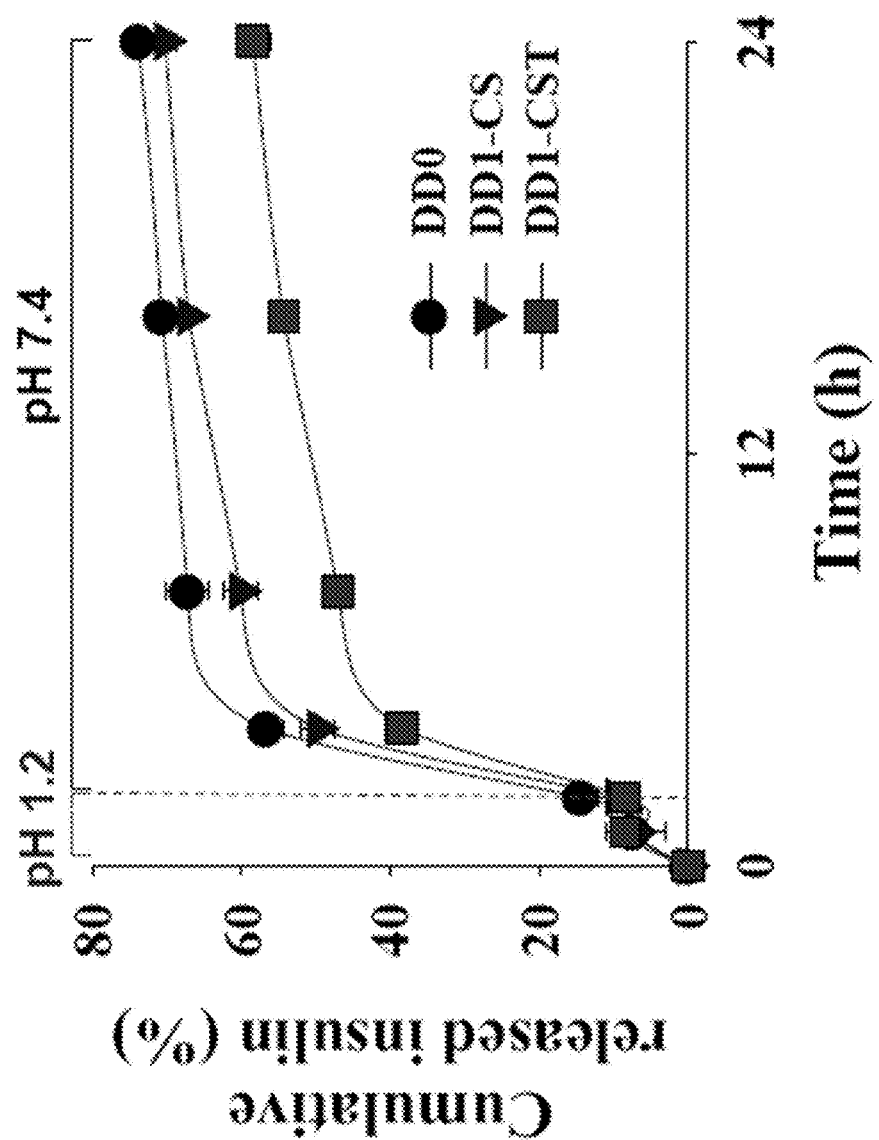
FIG. 29 is a graph of the amount of insulin released from three exemplary liposomal compositions over time, at pH 7.4 and pH 1.2.

The amount of released insulin over time for the three protein-loaded liposomes is shown in FIG. 29, at a pH of 7.4. The a single data point at a pH of 1.2 (after 2 hours) is shown, as well. As can be seen in the graph of FIG. 29, the amount of total (cumulative) insulin released by the liposomes at pH 7.4 varies, from a total of about 75% released in the non-coated liposome after 24 hours, to about 70% released in the same time period with the CS-coated (no bile acid) liposomes, and down to about 55% released in the CS-TCA coated liposomes. All of the liposomes released most of the insulin within 8 hours. The data at a pH of 1.2, which shows that all of the liposomes release only a small amount (about 5-15%) of their insulin, indicates that when exposed to an environment of low pH, such as in the stomach, the liposomes are generally stable and do not lose a significant amount of the protein therapeutic agent they hold.

In vitro cellular uptake. Human epithelial colorectal adenocarcinoma cells (caco-2 cells) were maintained in Dulbeco's Modified Eagle's Medium (DMEM) with 1% penicillin-streptomycin and 10% FBS in a humidified standard incubator at 37° C. with a 5% $CO_2$ atmosphere. Prior to testing, cells ($1\times10^5$ cells/mL) that were grown as a monolayer were harvested via trypsinization using a 0.25% (wt/vol) trypsin/0.03% (wt/vol) EDTA solution. Caco-2 cells suspended in DMEM were seeded onto each well plate and cultured for 24 hours prior to the in vitro cell testing. The cellular uptake of the liposomes (provided in an amount equivalent to an insulin-Ce6 concentration of 10 ug/mL, treated for 4 hr) was monitored by FACSCalibur Flow Cytometer (Becton Dickinson, USA). In addition, the localization of the liposome was examined by fluorescence of the insulin-Ce6 loaded liposome using a confocal laser scanning microscope.

Figure 30:
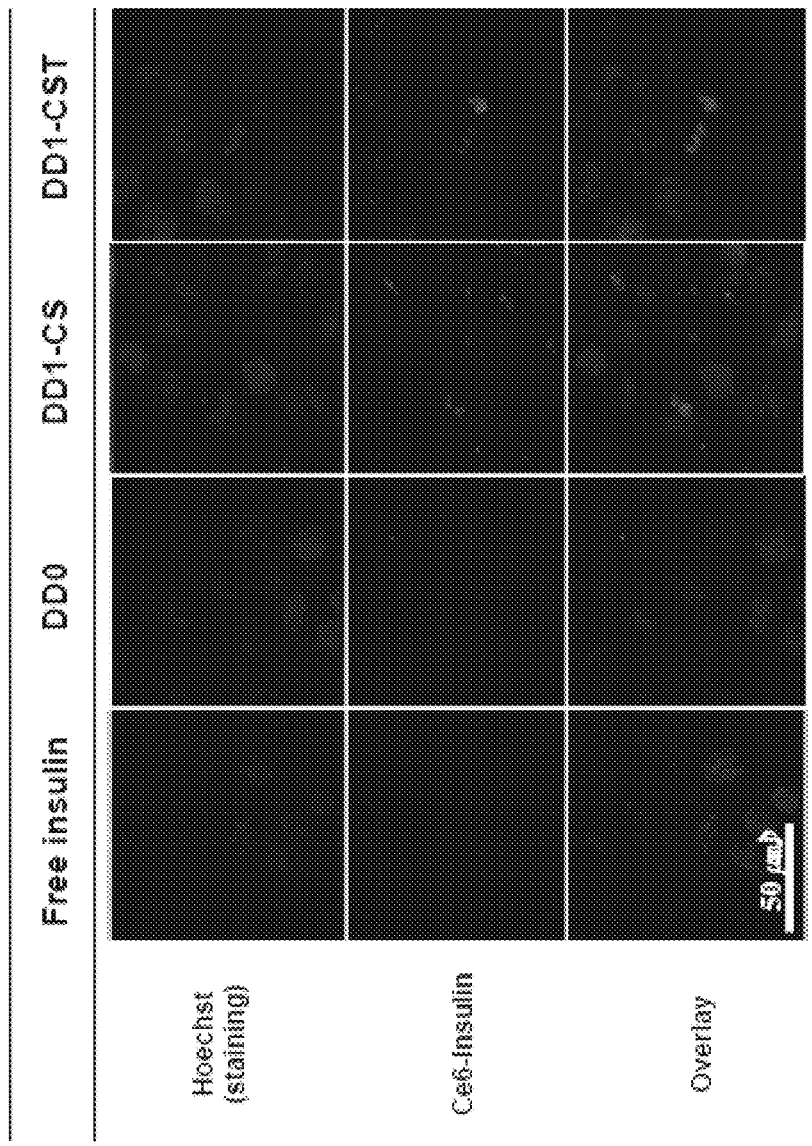
FIG. 30 is a series of images showing the amount of Ce6-labeled insulin present in cells after exposure to exemplary liposomal compositions.
Figure 31:
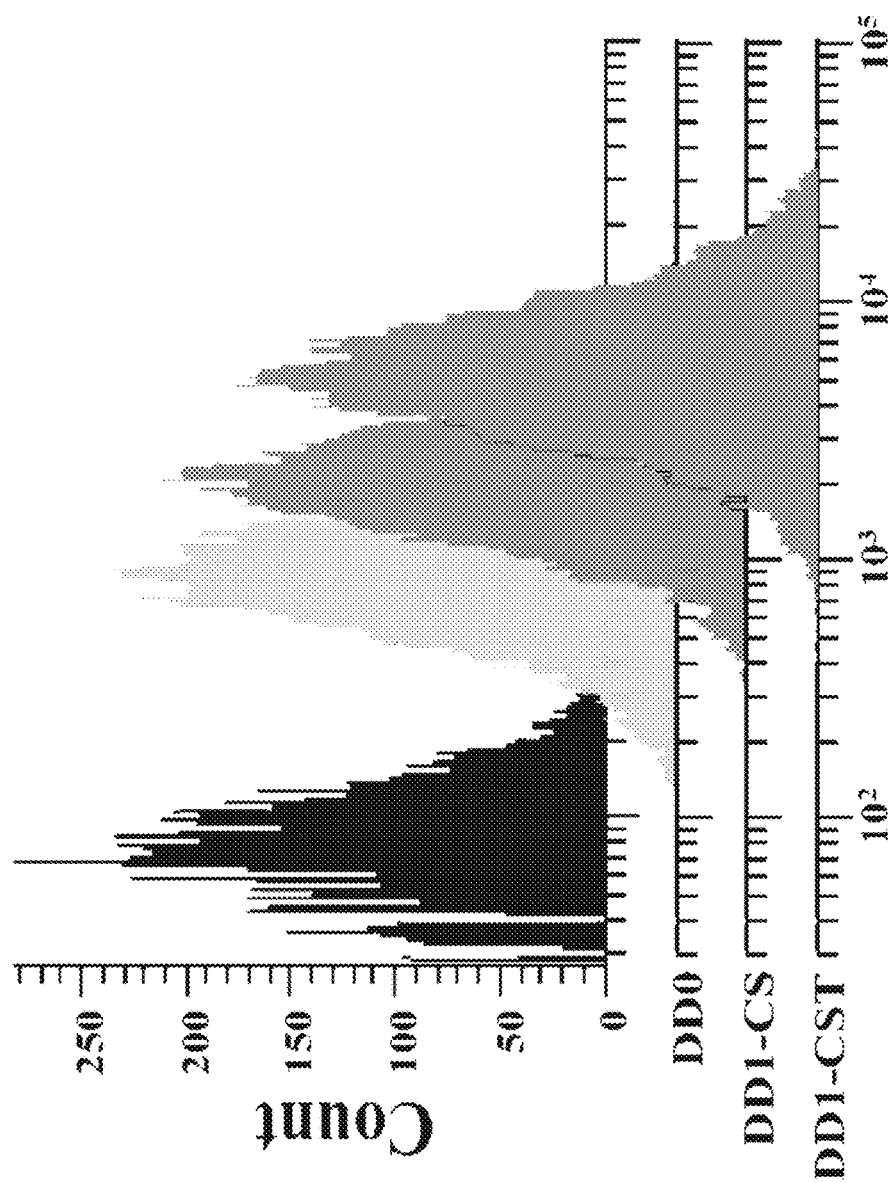
FIG. 31 is a graph showing the fluorescence counts and cell numbers for animals treated orally with exemplary liposomal compositions.

The results of this study is shown in FIG. 30, which is a series of micrographs of the stained cells after exposure to the liposomes, with the first row showing the stained liposomes, the second row showing the fluorescent signal from the Ce6-labeled insulin, and the last row showing an overlay of rows 1 and 2. From the last row, it is evident that there is relatively little labeled insulin present in the control sample (cells treated with non-liposomal insulin) and in the cells treated with the DD0 liposomes. In contrast, there is labeled insulin present in the cells treated with the chondroitin sulfate and CS-TCA coated liposomes. An analysis of the cells which contained the liposomes is shown in FIG. 31.

In vivo organ accumulation. In vivo studies were conducted with 6- to 8-week old female BALB/c mice. The three types of liposomes containing insulin tagged with Ce6 were administered orally to the mice at a dose equivalent to 50 IU/kg of insulin. A different cohort of mice was given free insulin (no liposomes), at the same dose. A 12-bit CCD camera (Image Station 4000 MM; Kodak, New Haven, Conn., USA) equipped with a C mount lens and a long-wave emission filter (600-700 nm) were used to obtain live photo-luminescent images of the mice from the time of administration (t=0) to 24 hours.

Figure 32:
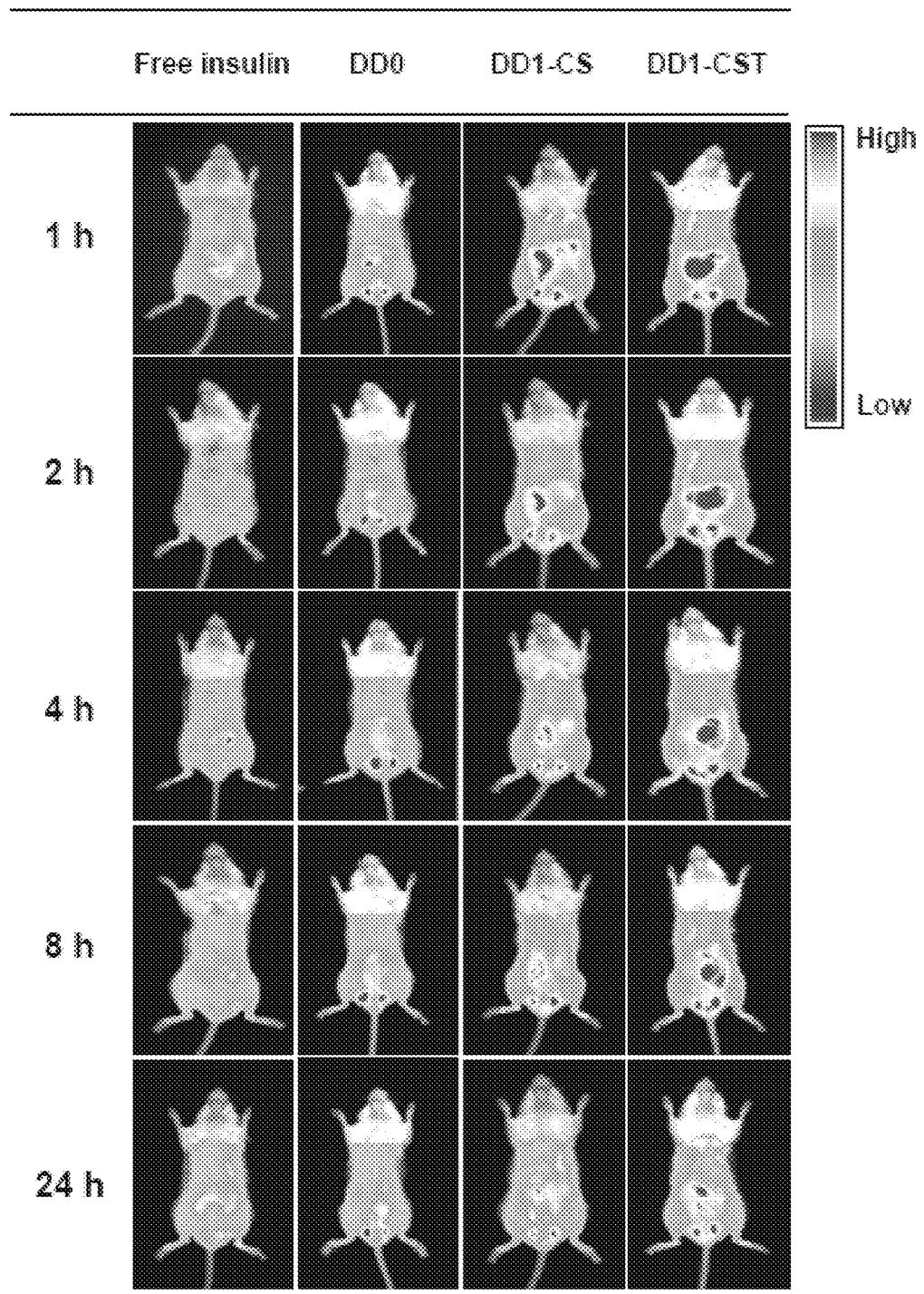
FIG. 32 is a series of images showing the amount and location of Ce6-labeled insulin present in live mice after oral administration of exemplary liposomal compositions.

Micrographs of a live mouse at 1, 2, 4, 8 and 24 hours are shown in FIG. 32, treated with free insulin (first column) or the three liposomal insulin formulations (columns 2-4, as indicated). As can be seen in the photos, the mice treated with CS-TCA coated liposomes showed the most fluorescent signal, indicating the greatest amount of labeled insulin present in the animals, with less signal showing in the CS-coated liposomes, and significantly less showing in the other two groups.

Figure 33:
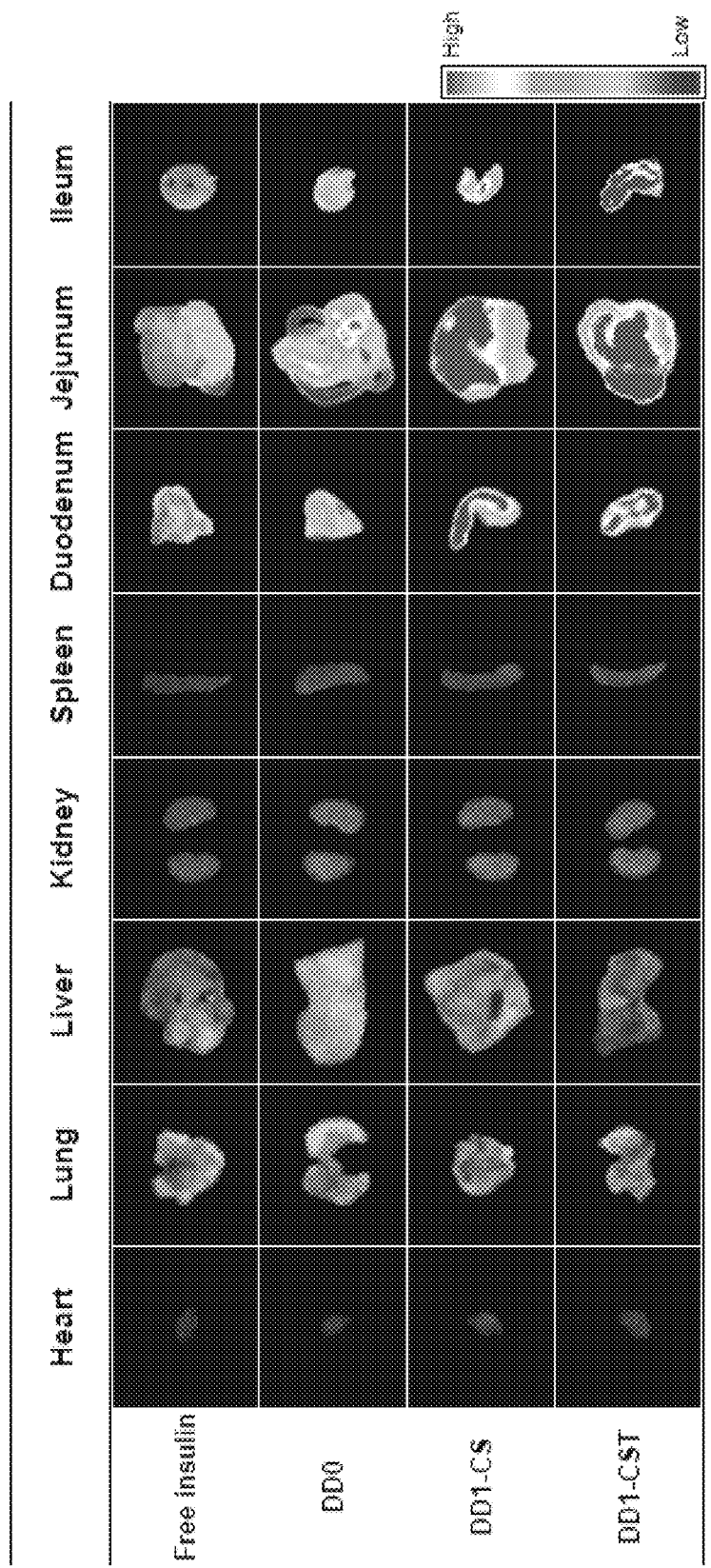
FIG. 33 is a series of images showing the amount of Ce6-labeled insulin present in various organs of mice after oral administration of exemplary liposomal compositions.
Figure 34:
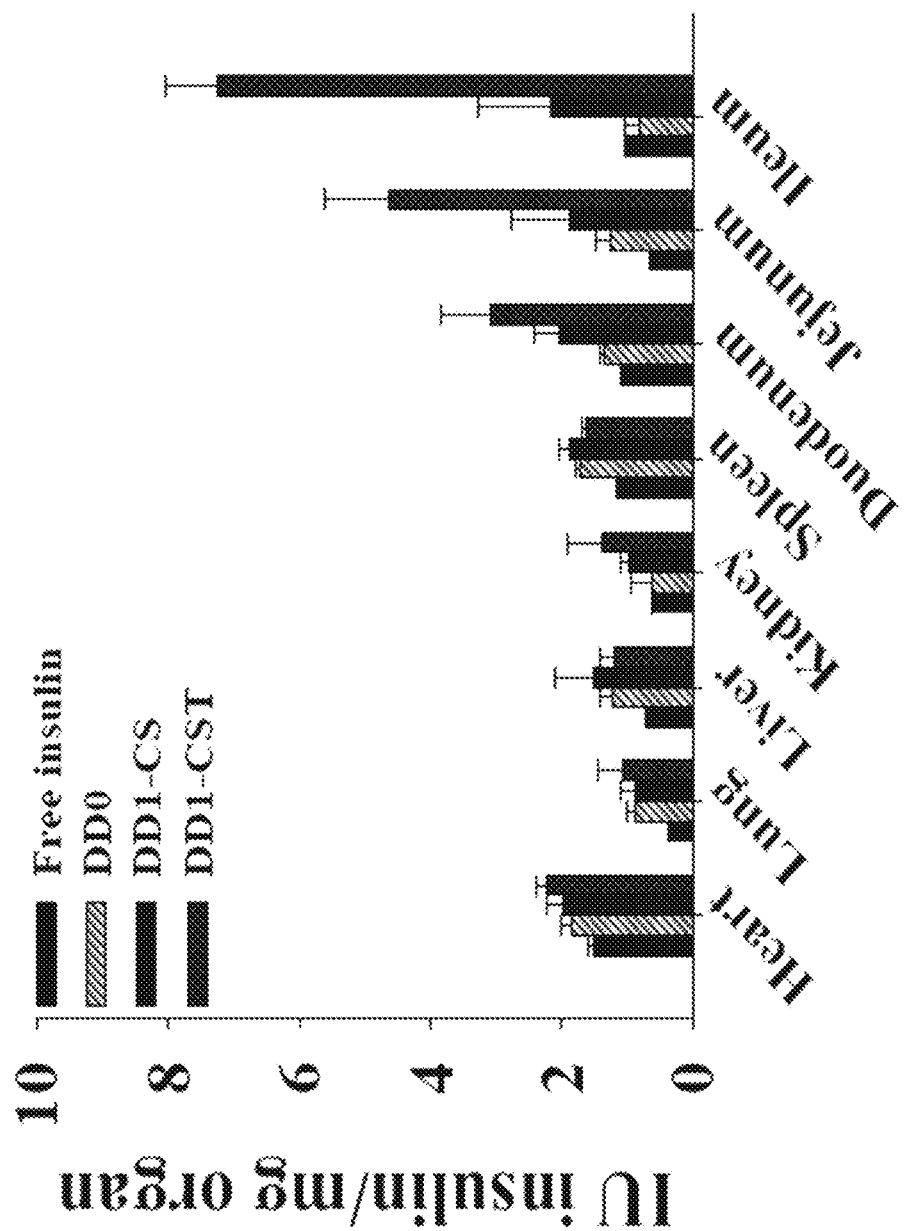
FIG. 34 is a graph of the insulin present in each organ shown in FIG. 33. For each organ listed, the bars (from left to right) are for the free insulin treatment, the treatment with DD0, the treatment with DD1-CS and the treatment with DD1-CST.

Ex vivo fluorescence studies. At 4 hours post injection, a subset of the mice were sacrificed (n=5), and the excised organs were investigated (heart, lung, liver, kidney, spleen, duodenum, jejunum and ileum). Micrographs of the organs are shown in FIG. 33. After harvesting and suspension in 70% ethanol with 0.3 N HCl, the organs were then homogenized to extract the tagged insulin. Following centrifugation, the Ce6 fluorescence (excitation at 410 nm, emission at 670 nm) in the supernatant was measured using a fluorescence plate reader. The levels of the fluorescence are shown in FIG. 34.

FIG. 33 shows that the labeled insulin is present primarily in the duodenum and jejunum of the mice treated with the CS and CS-TCA coated liposomes. FIG. 34 summarizes the distribution, and shows that significantly more labeled insulin is present in the mice treated with the CS-TCA coated liposomes (the right-most bar in each set) than the CS coated liposomes (the third from the left bar in each set).

Plasma concentrations. Blood was collected via cardiac puncture, kept in microtainer tubes with EDTA, and centrifuged to obtain plasma. After freeze-drying the plasma sample, it was dissolved in 70% ethanol with 0.3 N HCl, to extract the Ce6 label. The intensity of the Ce6 fluorescence in the supernatant was measured as described previously (n=5). The Ce6 fluorescence may originate from intact insulin or from insulin fragments (after digestion) containing the Ce6 label.

Figure 35:
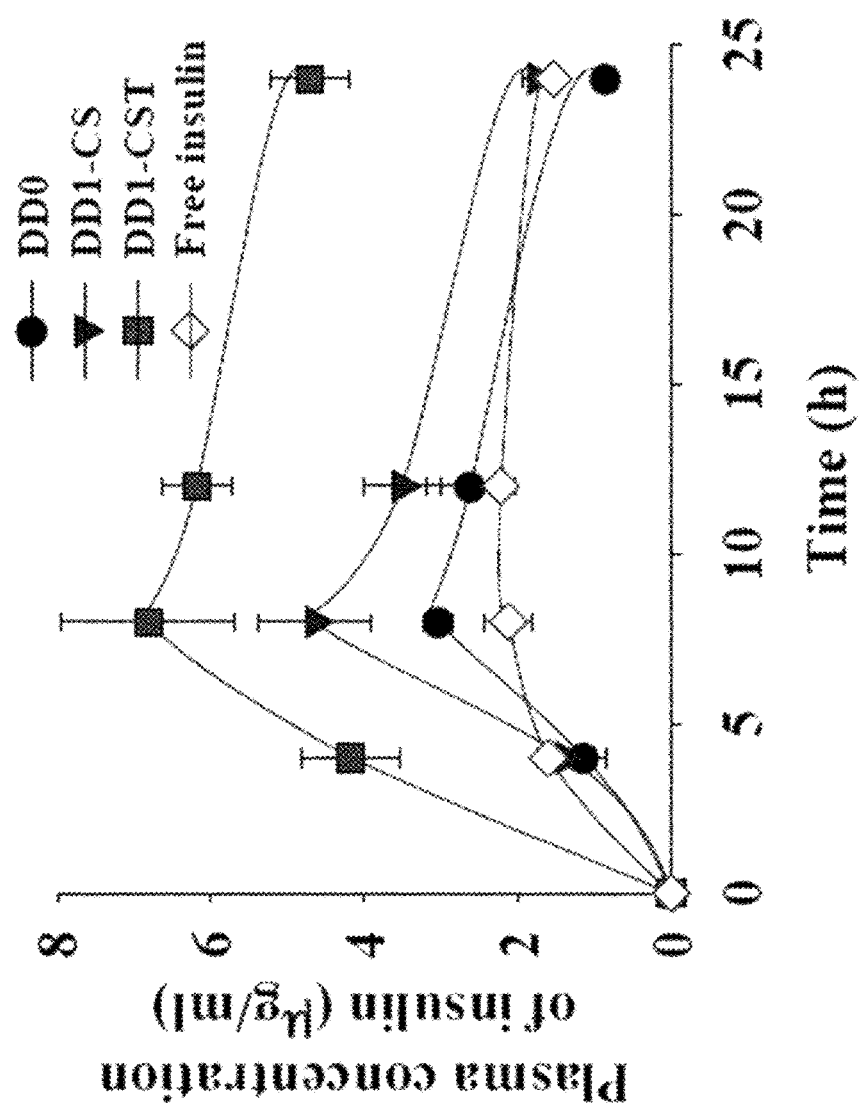
FIG. 35 is a graph of the plasma concentration of insulin over time for animals after oral administration of exemplary liposomal compositions.

The plasma data is shown in FIG. 35. The plasma from the mice treated with the CS-TCA coated liposomes (the top line, square symbols) show the highest insulin levels, peaking at about 8 hours post administration. The data shows that more labeled insulin is present in the mice treated with the CS coated liposomes (the line second from the top, inverted triangle symbols) than either the non-coated liposomes (DD0—the circle symbols, and free insulin—the open symbols).

The pharmacological activity of unmodified liposomal insulin was also studied. Female BALB/c mice (approx. 20-30 gm each) were rendered diabetic by daily intraperitoneal injection of streptozotocin (STZ, dissolved in 10 mm citrate buffer at pH 4.5) at a dose of 75 mg/kg body weight for 3 days. Mice were considered to be diabetic when their fasting blood glucose level was higher than 350 mg/dL, which occurred about 1 week after the STZ treatment. Blood samples were collected from the tail vein of mice prior to administration of the insulin, and at different time intervals after dosing. The blood glucose levels were immediately determined using a glucose meter (ACCU-CHEK active, Roche Diagnostics), n=5.

Figure 36:
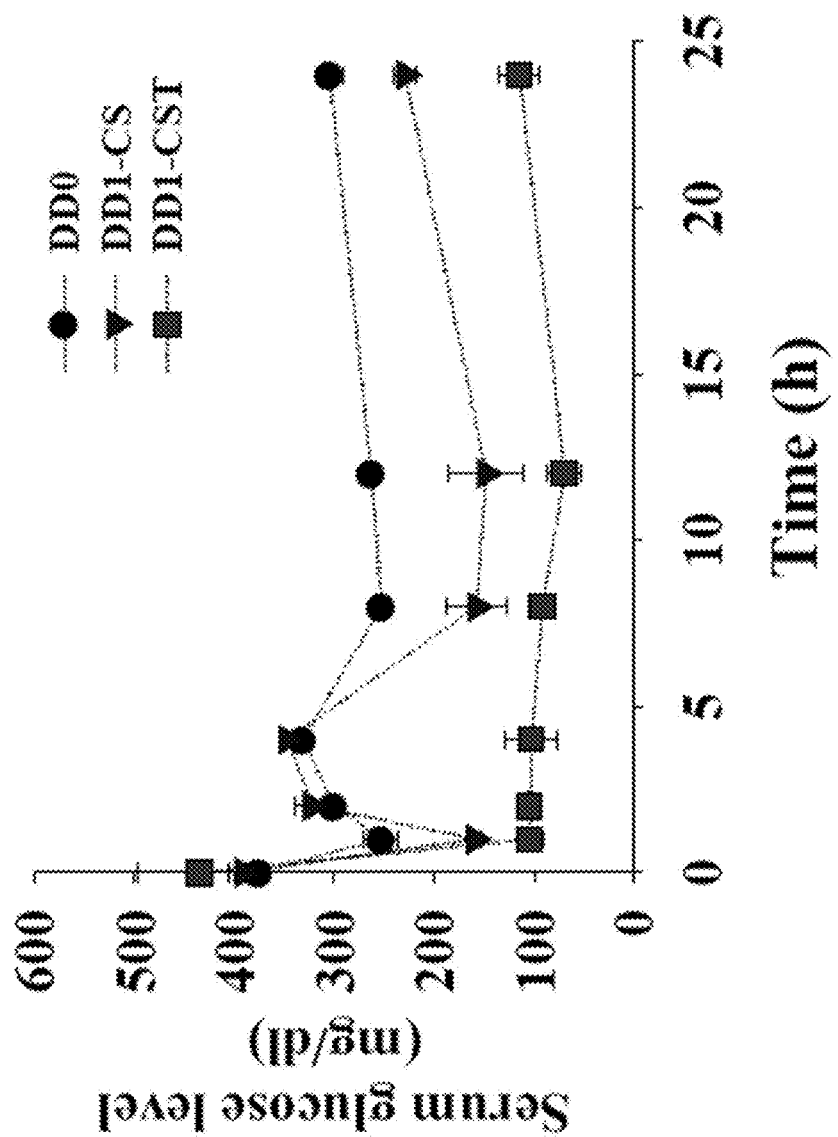
FIG. 36 is a graph of the serum levels over time for animals after oral administration of exemplary liposomal compositions.

The mice were treated with 50 IU/kg of normal insulin, or 1 IU/20 gm of mouse, which was administered orally. The serum glucose levels for the mice over time are shown in FIG. 36. The lowest and most constant levels are shown in the mice which were treated with the CS-TCA coated liposomes (lowest line, square symbols), which fell to about 100 mg/dL within one hour after administration, and which were generally maintained for 24 hours. The mice treated with the CS coated liposomes (middle line, inverted triangle symbols) had serum glucose levels which initially were lowered to about 150 mg/dL in the first hour, but which rose back to near 300 mg/dL for the following 3 hours before lowering again to about 150 mg/dL, with a gradual rise to about 200 mg/dL by 24 hours. The DD0 treated mice (top line, circle symbols) had serum glucose levels which lowered slightly to about 250 mg/dL, vacillated in a similar manner to the CS-coated liposomes, and was maintained between about 250-300 mg/dL.

(II) Liposomal Doxorubicin.

Liposome preparation for the small molecule therapeutic agent studies. Dimethyl dioctadecyl ammonium bromide ("DD") was dissolved in chloroform and the solvent was removed by rotary evaporation to form a thin film on the surface of the flask. The film was rehydrated in 120 mM ammonium sulfate and sonicated for 30 minutes. The free ammonium sulfate was removed by dialysis (MWCO 1000) against pure water.

Figure 40:
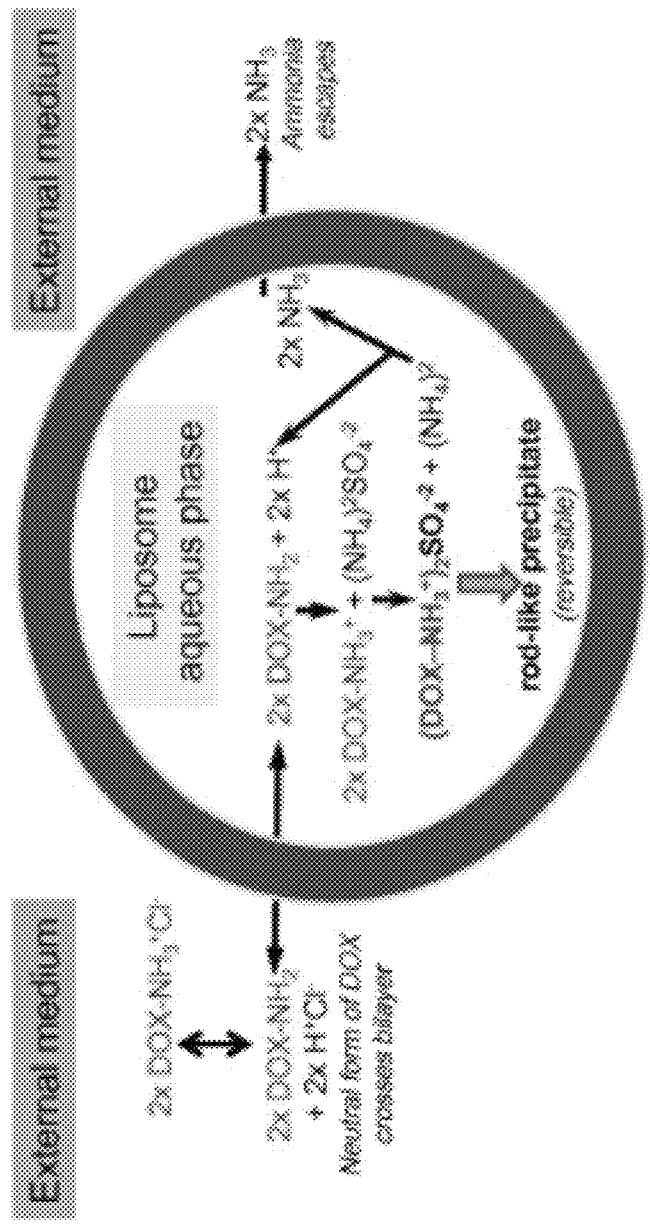
FIG. 40 is a schematic diagram showing the creation of an ammonium sulfide gradient to load the dimethyl dioctadecyl ammonium bromide (DD) liposomes with doxorubicin (DOX).

To load the DD liposomes with doxorubicin (DOX), an ammonium sulfide gradient was created as shown in FIG. 40.

After creation of the gradient, the liposomal solution and a doxorubicin (DOX) solution were mixed and incubated at 60° C. Excess free DOX was removed by dialysis (MWCO 1000) against water. The final DOX-loaded liposomes were lyophilized. The DOX concentration was calculated based on the measurement by UV-Vis at 490 nm and the loading efficiency was calculated using the following equation:

$$\text{Loading efficiency (\%)} = 100 \times \frac{\text{(weight of DOX present in the particles)}}{\text{(weight of DOX used)}}$$

For the oral formulation, the DOX-loaded liposomes were dissolved in polyoxamer (40 mg/mL) containing PBS at 60° C. The extruder was thermostated to 60° C. prior to liposome extrusion through a 100 nm membrane. The samples were extruded ten times through the membrane. After the extrusion, the liposomes were coated with CS-TCA (1:1.5 w/w %) for oral administration.

The liposomal DOX particles were characterized by particle size and zeta potential analysis, as described for the liposomal insulin formulations, both before and after coating with the covalently bound chondroitin sulfate-bile acid moiety. The data is shown below in Table 3.

TABLE 3

Characterization data for liposomal doxorubicin formulations.

| | average particle size (nm) | PDI | average Zeta potential (mV) |
|---|---|---|---|
| DOX-liposome | 377.6 | 0.425 | 17.7 |
| CS-TCA-coated DOX liposome | 220.8 | 0.237 | −39 |

In vivo therapeutic efficacy in a tumor bearing animal model. The in vivo anticancer efficacy of free DOX, the cationic DOX-loaded liposome without a bile acid coating ("DOX-liposome"), and the anionic DOX-loaded liposome with the CS-TCA coating ("DL/CS-TCA") was evaluated in a xenograft mouse model. HT-29 cells ($1 \times 10^7$ cells per mouse) were subcutaneously injected into the back of NOD/SCID mice (n=3). When the tumor size reached approximately 100-150 mm$^3$, each mouse received an oral administration of PBS, 10 mg/kg free DOX, 10 mg/kg DOX in the DOX-liposome composition, or 10 mg/kg DOX in the DL/CS-TCA composition, once every two days. Tumor size and body weight were measured every 2 days. Tumor volumes were measured with a digital caliper and the tumor volume was calculated using the equation shown below.

$$\text{Tumor volume} = (\text{Length} \times \text{width}^2)/2$$

Figure 37:
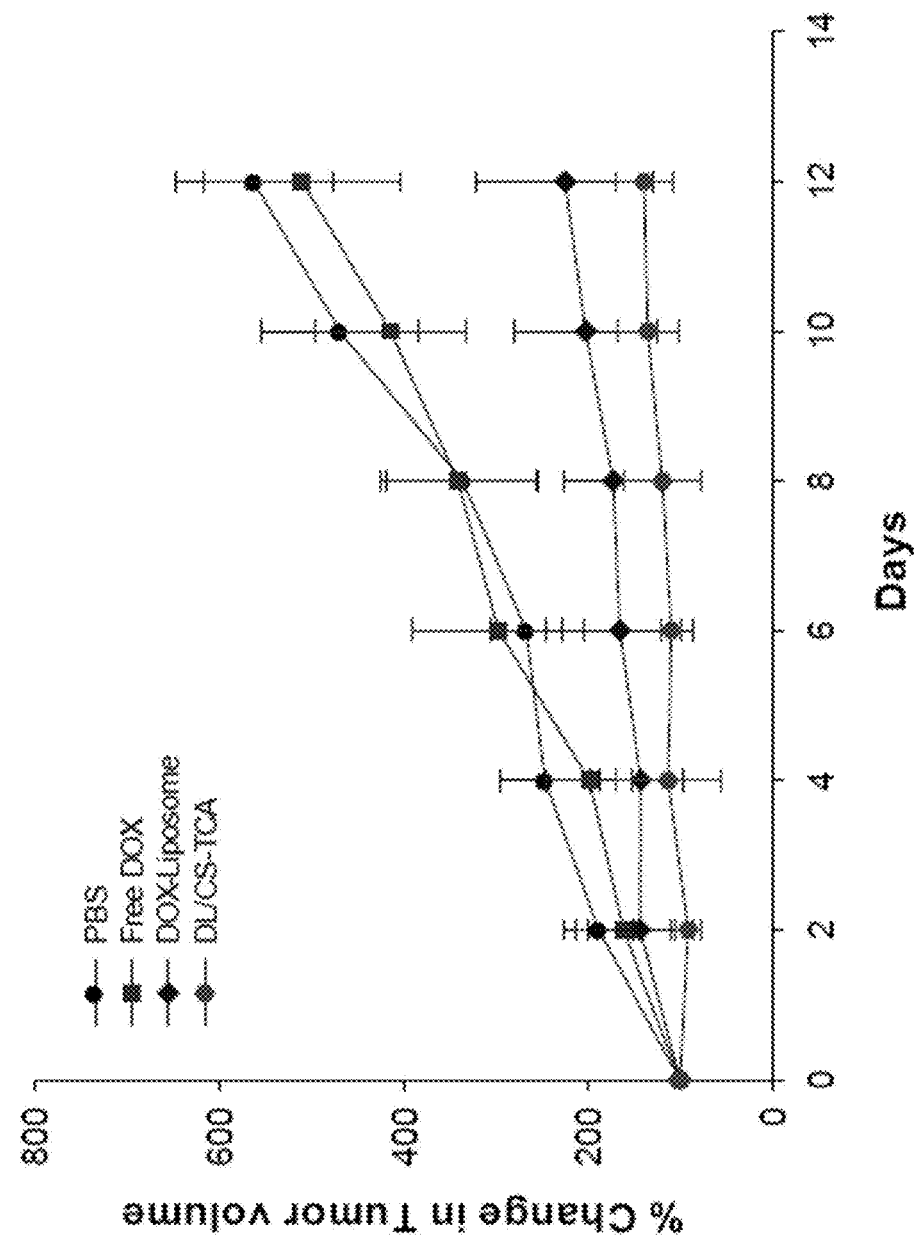
FIG. 37 is a graph showing the change in tumor volume over time in animals treated with exemplary liposomal compositions.

The change in the tumor volume for each of the treatments is shown in FIG. 37. The upper-most line (dark circles) at day 12 is the PBS control. The next line down at day 12 (square symbols) is the free DOX. These results indicate that free oral DOX is not statistically better at reducing tumor volume than the buffer. The bottom line (light circles) is percent change in tumor volume for the animals treated with the anionic DOX-loaded liposomes with the CS-TCA coating ("DL/CS-TCA"), which shows generally no change in tumor volume over the 12 days after a single oral dose. The second from the bottom line (the diamonds) is the percent change in tumor volume for the animals treated with the cationic DOX-loaded liposome without a bile acid coating ("DOX-liposome"), and these tumors increase by about 200% over the 12 days.

Figure 38:
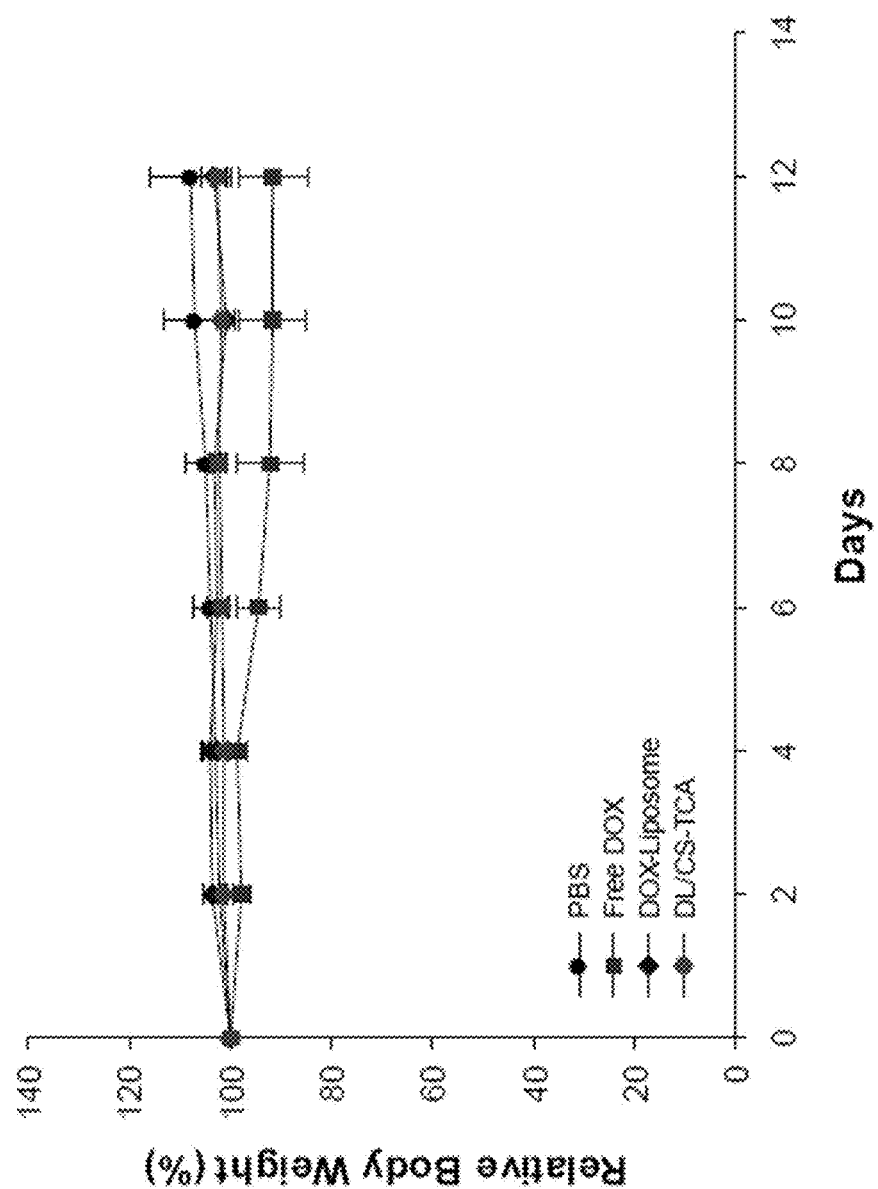
FIG. 38 is a graph showing the relative body weight over time in animals treated with exemplary liposomal compositions.

FIG. 38 shows the change in the relative body weight of the treated animals. The body weight of the free DOX group appears to decrease slightly over the 12 days, but the remaining treatment groups maintain or slightly increase their body weight over that time.

The experiments disclosed herein include the delivery of plasmid DNA encoding enhanced green fluorescence protein (eGFP), Exendin-4 and GLP-1 in mice by oral administration. The plasmid DNA was first complexed with cationic branched polyethyleneimine (bPEI), yielding a cationic complex. The complex was then coated with taurocholic acid (TCA) which was covalently bonded to heparin, providing a particle with a size between about 100 and about 200 nm. Oral administration of the particles containing the DNA was shown to express the produce of the DNA in animals.

In addition to DNA, a cationic particle can be formed from a protein such as insulin, coupled with a cationic polymer such as protamine. The cationic particle can be coated with heparin-TCA, to yield a particle on the order of a few microns in size. Such a particle would be anionic and can be used to reduce blood glucose levels.

The delivery of a small molecule drug, doxorubicin, which is not appreciably bioavailable after oral administration, was achieved by its formulation as bile acid-wrapped particles. The anionic particle formed by complexing doxorubicin with chondroitin sulfate was coated with ε-poly(L-lysine), resulting in a cationic complex. The particle was then coated with heparin-TCA. The orally administered particles showed significant plasma concentrations of doxorubicin in normal mice. The use of liposomes in the bile acid-containing formulations was also validated, with two exemplary therapeutic agents: a small-molecule drug (doxorubicin) and a protein (insulin).

REFERENCES

Thanki K, Gangwal R P, Sangamwar A T, Jain S. Oral delivery of anticancer drugs: challenges and opportunities. J. Control. Release, 2013; 170(1):15-40.

Mei L, Zhang Z, Zhao L, Huang L, Yang X L, Tang J, Feng S S. Pharmaceutical nanotechnology for oral delivery of anticancer drugs. Adv. Drug Deliv. Rev. 2013; 65(6):880-890.

Da Rocha A B, Lopes R M, Schwartsmann G. Natural products in anticancer therapy. Curr. Opin. Pharmacol. 2001; 1(4):364-369.

Mohan P, Rapoport N. Doxorubicin as a molecular nanotheranostic agent: effect of doxorubicin encapsulation in micelles or nanoemulsions on the ultrasound-mediated intracellular delivery and nuclear trafficking. Mol. Pharm. 2010; 7(6):1959-1973.

Swarnakar N K, Thanki K, Jain S. Bicontinuous cubic liquid crystalline nanoparticles for oral delivery of doxorubicin: implications on bioavailability, therapeutic efficacy, and cardiotoxicity. Pharm. Res. 2014; 31(5): 1219-1238.

Wang J, Li L, Du Y, Sun J, Han X, Luo C, Ai X, Zhang Q, Wang Y, Fu Q. Improved oral absorption of doxorubicin by amphiphilic copolymer of lysine-linked di-tocopherol polyethylene glycol 2000 succinate. Mol. Pharm. 2015; 12(2):463-473.

Dayton A, Selvendiran K, Meduru S, Khan M, Kuppusamy M L, Naidu S, Kalai T, Hideg K, Kuppusamy P. Amelioration of doxorubicin-induced cardiotoxicity by an anti-cancer-antioxidant dual-function compound, HO-3867. J. Pharm. Exp. Ther. 2011; 339(2):350-357.

Li Q, Lv S, Tang Z, Liu M, Zhang D, Yang Y, Chen X. A co-delivery system based on paclitaxel grafted mpeg-b-plg loaded with doxorubicin: preparation, in vitro and in vivo evaluation. Int. J. Pharm. 2014; 471(1-2):412-420.

Kim J E, Cho H J, Kim J S, Shim C K, Chung S J, Oak M H, Yoon I S, Kim D D. The limited intestinal absorption via paracellular pathway is responsible for the low oral bioavailability of doxorubicin. Xenobiotica. 2012; 43(7): 579-591.

Thomas C, Pellicciari R, Pruzanski M, Auwerx J, Schoonjans K. Targeting bile-acid signalling for metabolic diseases. Nat. Rev. Drug Discov. 2008; 7(8):678-693.

Alrefai W A, Gill R K. Bile acid transporters: structure, function, regulation and pathophysiological implications. Pharm. Res. 2007; 24(10):1803-1823.

Dawson P A, Lan T, Rao A. Bile acid transporters. J. Lipid Res. 2009; 50(12):2340-2357.

Yin Win K, Feng S S. Effects of particle size and surface coating on cellular uptake of polymeric nanoparticles for oral delivery of anticancer drugs. Biomaterials. 2005; 26(15):2713-2722.

Holm R, Müllertz A, Mu H. Bile salts and their importance for drug absorption. Int. J. Pharm. 2013; 453(1):44-55.

Khatun Z, Nurunnabi M, Reeck G R, Cho K J, Lee Yk. Oral delivery of taurocholic acid linked heparin-docetaxel conjugates for cancer therapy. J. Control. Release. 2013; 170(1):74-82.

Alam F, Al-Hilal T A, Chung S W, Seo D, Mahmud F, Kim H S, Kim S Y, Byun Y. Oral delivery of a potent anti-angiogenic heparin conjugate by chemical conjugation and physical complexation using deoxycholic acid. Biomaterials. 2014; 35(24):6543-6552.

Tran T H, Nguyen C T, Kim D P, Lee Yk, Huh K M. Microfluidic approach for highly efficient synthesis of heparin-based bioconjugates for drug delivery. Lab Chip. 2012; 12(3):589-594.

Oprea A M, Profire L, Lupusoru C E, Ghiciuc C M, Ciolacu D, Vasile C. Synthesis and characterization of some cellulose/chondroitin sulphate hydrogels and their evaluation as carriers for drug delivery. Carbohydr Polym. 2012; 87(1):721-729.

Zhang Y, Chan H F, Leong K W. Advanced materials and processing for drug delivery: the past and the future. Adv. Drug Deliv. Rev. 2013; 65(1):104-120.

He C, Yin L, Tang C, Yin C. Size-dependent absorption mechanism of polymeric nanoparticles for oral delivery of protein drugs. Biomaterials. 2012; 33(33): 8569-8578.

Kang H C, Bae Y H. Co-delivery of small interfering RNA and plasmid DNA using a polymeric vector incorporating endosomolytic oligomeric sulfonamide. Biomaterials. 2011; 32(21):4914-24.

Kang H C, Kang H J, Bae Y H. A reducible polycationic gene vector derived from thiolated low molecular weight branched polyethyleneimine linked by 2-iminothiolane. Biomaterials. 2011; 32(4):1193-1203.

Kang H C, Samsonova O, Kang S W, Bae Y H. The effect of environmental pH on polymeric transfection efficiency. Biomaterials. 2012; 33(5):1651-62.

Hu J, Miura S, Na K, Bae Y H. pH-responsive and charge shielded cationic micelle of poly (1-histidine)-block-short branched PEI for acidic cancer treatment. J. Control. Release. 2013; 172(1):69-76.

Kim D, Gao Z G, Lee E S, Bae Y H. In vivo evaluation of doxorubicin-loaded polymeric micelles targeting folate receptors and early endosomal pH in drug-resistant ovarian cancer. Mol. Pharm. 2009; 6(5):1353-1362.

Jafari V, Allahverdi A, Vafaei M. Ultrasound-assisted synthesis of colloidal nanosilica from silica fume: Effect of sonication time on the properties of product. Adv Power Technol. 2014; 25(5):1571-1577.

Talelli M, Iman M, Varkouhi A K, Rijcken C J, Schiffelers R M, Etrych T, Ulbrich K, van Nostrum C F, Lammers T, Storm G. Core-crosslinked polymeric micelles with controlled release of covalently entrapped doxorubicin. Biomaterials. 2010; 31(30):7797-7804.

C. R. Safinya, K. K. Ewert, Nature 489 (2012) 372-374.

C. Oerlemans, R. Deckers. G. Storm, W. E. Hennink. j. F. Nijsen, J. Control. Release 168 (2013) 327-333.

J. P. Motion, J. Nguyen, F. C. Szoka, Angew. Chem. Int. Ed. 51 (2012) 9047-9051.

Y. Yoshizaki, E. Yuba, N. Sakaguchi. K. Koiwai, A. Harada, K. Kono. Biomaterials 35 (2014) 8186-8196.

A. Napoli. M. Valentini, N. Tirelli, M. Muller, J. A. Hubbell, Nat. Mater. 3 (2004) 183-189.

A. Saitoh, K. Takiguchi, Y. Tanaka, H. Hotani, Proc. Natl. Acad. Sci. U.S.A. 95 (1998) 1026-1031.

M. Przybylo, J. Procek, M. Hof, M. Langner, Chem. Phys. Lipids 178 (2014) 38-44.

U. Y. Lee, N. M. Oh, D. S. Kwag, K. T. Oh, Y. T. Oh, Y. S. Youn, E. S. Lee, Angew. Chem. Int. Ed. 51 (2012) 7287-7291, E. S. Lee, D. Kim, Y. S. Youn, K. T. Oh. Y. H. Bae, Angew. Chem. Int. Ed. 47 (2008) 2418-2421.

W. L Haisler, D. M. Timm, J. A. Cage, H. Tseng, T. C. Killian, C R Souza, Nat. Protoc. 8 (2013) 1940-1949.

U. Y. Lee, Y. T. Oh, D. Kim, E. S. Lee, Int J. Pharm. 471 (2014) 166-172

O. O. Krylova, P. Pohl, Biochemistry 43 (2004) 3696-3703.

A. Taluja, Y. H. Bae, Pharm. Res. 24 (2007) 1517-1526.

D. S. Kwag, K T. Oh. E. S. Lee, J. Control. Release 187 (2014) 83-90.

D. S. Kwag, K. Park, Y. S. Youn, E. S. Lee, Colloids and Surfaces B: Biointerfaces 135 (2015), 143-149.

Kang et al, Mol. Pharmaceutics, 2015, 12 (8), 2845-2857.

Various features and advantages of the invention are set forth in the following claims.

The invention claimed is:

1. A therapeutic composition comprising:
   a core complex comprising a therapeutic agent and having an exterior surface with a net positive charge at a pH of 5; and
   a cholic acid covalently bound to an anionic polymer wherein the anionic polymer comprises hyaluronic acid, chondroitin sulfate, or heparin;
   wherein the anionic polymer has a net negative charge at neutral pH, and
   wherein the anionic polymer is electrostatically coupled to the exterior surface.

2. The composition of claim 1, wherein the therapeutic agent comprises a nucleic acid.

3. The composition of claim 2, wherein the nucleic acid comprises a gene.

4. The composition of claim 3, wherein the gene encodes GLP-1 or Exendin 4.

5. The composition of claim 1, wherein the therapeutic agent comprises a peptide.

6. The composition of claim 5, wherein the peptide is insulin.

7. The composition of claim 1, wherein the therapeutic agent is a small molecule.

8. The composition of claim 6, wherein the small molecule is doxorubicin.

9. The composition of claim 1, wherein the therapeutic agent comprises a vaccine or virus.

10. The composition of claim 1, wherein the core complex comprises a cationic polymer.

11. The composition of claim 10, wherein the cationic polymer is selected from at least one of polyethylenimine, protamine, or poly(lysine).

12. The composition of claim 1, wherein the core complex comprises a cationic liposome.

13. The composition of claim 12, wherein the cationic liposome comprises a cationic lipid.

14. The composition of claim 1, wherein the cholic acid comprises a cholic acid selected from the group consisting of cholic acid, chenocholic acid, deoxycholic acid, lithocholic acid, ursodeoxycholic acid, chenodeoxycholic acid, taurocholic acid, glycocholic acid, taurodeoxycholic acid, glycodeoxycholic acid, taurochenodeoxycholic acid, or glycochenodeoxycholic acid.

15. The composition of claim 14, wherein the cholic acid is taurocholic acid.

16. A method of delivering a therapeutic agent to a cell, the method comprising oral administration of a therapeutic composition of claim 1 to a subject.

17. The method of claim 16, wherein the therapeutic composition is absorbed by the subject through a bile acid transporter in the gastrointestinal tract of the subject, and
   wherein the therapeutic composition enters the enterohepatic circulatory system of the subject.

18. A method of treating cancer, the method comprising orally administering a therapeutic composition of claim 1 to a subject, wherein the therapeutic agent is an anticancer agent.

19. A method of treating a metabolic disorder, the method comprising administering a therapeutic composition of claim 1 to a subject, wherein the therapeutic agent is selected from at least one of GLP-1, Exendin 4, or insulin.

* * * * *

UNITED STATES PATENT AND TRADEMARK OFFICE
CERTIFICATE OF CORRECTION

PATENT NO.         : 10,350,169 B2
APPLICATION NO.    : 15/523634
DATED              : July 16, 2019
INVENTOR(S)        : You Han Bae et al.

Page 1 of 1

It is certified that error appears in the above-identified patent and that said Letters Patent is hereby corrected as shown below:

In the Claims

1. In Claim 8, Column 40, Line 3, please delete "claim 6" and insert -- claim 7 --

Signed and Sealed this
Third Day of December, 2019

Andrei Iancu
*Director of the United States Patent and Trademark Office*